(12) United States Patent
Fisher et al.

(10) Patent No.: US 10,314,870 B2
(45) Date of Patent: Jun. 11, 2019

(54) TROPISM MODIFIED CANCER TERMINATOR VIRUS (AD.5/3 CTV;AD.5/3-CTV-M7)

(71) Applicant: Virginia Commonwealth University, Richmond, VA (US)

(72) Inventors: Paul Fisher, Richmond, VA (US); Devanand Sarkar, Richmond, VA (US); Paul Dent, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 14/650,775

(22) PCT Filed: Dec. 10, 2013

(86) PCT No.: PCT/US2013/073989
§ 371 (c)(1),
(2) Date: Jun. 9, 2015

(87) PCT Pub. No.: WO2014/093270
PCT Pub. Date: Jun. 19, 2014

(65) Prior Publication Data
US 2016/0008413 A1    Jan. 14, 2016

Related U.S. Application Data

(60) Provisional application No. 61/735,177, filed on Dec. 10, 2012.

(51) Int. Cl.
| | | |
|---|---|---|
| *A61K 35/768* | (2015.01) | |
| *A61K 39/00* | (2006.01) | |
| *C12N 15/86* | (2006.01) | |
| *A61K 31/166* | (2006.01) | |
| *A61K 31/404* | (2006.01) | |
| *A61K 45/06* | (2006.01) | |
| *C12N 7/00* | (2006.01) | |

(52) U.S. Cl.
CPC .......... *A61K 35/768* (2013.01); *A61K 31/166* (2013.01); *A61K 31/404* (2013.01); *A61K 39/0011* (2013.01); *A61K 45/06* (2013.01); *C12N 7/00* (2013.01); *C12N 15/86* (2013.01); *A61K 2039/5254* (2013.01); *A61K 2039/55511* (2013.01); *C12N 2710/10032* (2013.01); *C12N 2710/10321* (2013.01); *C12N 2710/10332* (2013.01); *C12N 2710/10343* (2013.01); *C12N 2710/10371* (2013.01)

(58) Field of Classification Search
CPC .................................................. A61K 35/768
See application file for complete search history.

(56) References Cited

U.S. PATENT DOCUMENTS

| | | |
|---|---|---|
| 4,863,457 A | 9/1989 | Lee |
| 5,378,475 A | 1/1995 | Smith et al. |
| 5,443,505 A | 8/1995 | Wong et al. |
| 6,225,289 B1 | 5/2001 | Kovesdi et al. |
| 2003/0153065 A1 | 8/2003 | Kovesdi et al. |

FOREIGN PATENT DOCUMENTS

| | | |
|---|---|---|
| WO | WO-00/34444 | 6/2000 |
| WO | WO-2011/017107 | 2/2011 |

OTHER PUBLICATIONS

Fisher, Intl Conf. & Exhibit. on Virology Sep. 5-7, 2011.*
Park et al. Mole Pharm 2011;79:368-80.*
Mesh database: Obatoclax 2007.*
Lebedeva et al. Cancer Res 2008;68:7439-47.*
Pan et al. Cell Mole Immunol 2010;7:221-6.*
Garcia-Manero et al. Best Practice & Research Clinical Haematology 2012;25:427-35.*
Dash et al. PNAS 2010;10:1290-1305.*
American Cancer Society. "Cancer Facts and Figures 2012." Atlanta, GA: American Cancer Society Inc., 2012.
Anderson, W.F. "Human Gene Therapy." Nature, 1998, vol. 392: 25-30.
Azab, B., et al., "A new serotype chimera Cancer Terminator Virus (Ad.5/3-CTV) expands the efficiency and specificity of prostate cancer gene transfer and therapy", Cancer Res., Apr. 2012, vol. 72, Issue 8.
Bae, G.U., "Hydrogen peroxide activates p70(S6k) signaling pathway." J Biol Chem, 1999, vol. 274: 32596-602.
Bai, J. et al., "Predominant Bcl-XL knockdown disables antiapoptotic mechanisms: tumor necrosis factor-related apoptosis-inducing ligand-based triple chemotherapy overcomes chemoresistance in pancreatic cancer cells in vitro." Cancer Res, 2005, vol. 65: 2344-52.
Bailey, H.H. et al., "Phase II trial of daily oral perillyl alcohol (NSC 641066) in treatment-refractory metastatic breast cancer." Cancer Chemother Pharmacol, 2008, vol. 62: 149-57.

(Continued)

*Primary Examiner* — Scott Long
(74) *Attorney, Agent, or Firm* — W&C IP

(57) ABSTRACT

A tropism modified cancer terminator virus (Ad.5/3-CTV; Ad.5/3-CTV-M7) has been found to have infectivity that is Coxsackie Adenoviral Receptor (CAR) independent. The Ad.5/3-CTV (Ad.5/3-CTV-M7) may be used alone or in combination with other therapeutic agents such as agents that augment reactive oxygen (ROS) production, HDAC inhibitors, MCL-1 inhibitors and Bcl-2 inhibitors to treat a variety of cancers particularly including malignant glioma (GBM), renal cancer, prostate cancer, and colorectal cancer.

14 Claims, 46 Drawing Sheets

Specification includes a Sequence Listing.

(56) References Cited

OTHER PUBLICATIONS

Bardon, S. et al., "Monoterpenes inhibit proliferation of human colon cancer cells by modulating cell cycle-related protein expression." Cancer Lett, 2002, vol. 181: 187-94.
Bell, E.L. et al., "Mitochondrial reactive oxygen species trigger hypoxia-inducible factor-dependent extension of the replicative life span during hypoxia." Mol Cell Biol, 2007, vol. 27: 5737-45.
Bhang et al., "Tumor-specific imaging through progression elevated gene-3 promoter-driven gene expression," Nature Med 17: 123-129 (2011).
Bhutia, S.K. et al. "Autophagy switches to apoptosis in prostate cancer cells infected with melanoma differentiation associated gene-7/interleukin-24 (mda-7/IL-24)." Autophagy, 2011, vol. 7: 1076-1077.
Bhutia, S.K. et al., "Mechanism of autophagy to apoptosis switch triggered in prostate cancer cells by antitumor cytokine melanoma differentiation associated gene 7/interleukin-24." Cancer Res, 2010, vol. 70: 3667-3676.
Boucher, M.J. et al., "MEK/ERK signaling pathway regulates the expression of Bcl-2, Bcl-X(L), and Mcl-I and promotes survival of human pancreatic cancer cells." J Cell Biochem, 2000, vol. 79: 355-69.
Campani, D. et al., "Bcl-2 expression in pancreas development and pancreatic cancer progression." J Pathol, 2001, vol. 194: 444-50.
Carrington, E.M. et al., "Islet beta-cells deficient in Bcl-xL develop but are abnormally sensitive to apoptotic stimuli." Diabetes, 2009, vol. 58: 2316-23.
Chada, S. et al., "Bystander activity of Ad-mda7: human MDA-7 protein kills melanoma cells via an IL-20 receptor-dependent but STAT3-independent mechanism." Mol Ther, 2004, 10: 1085-1095.
Chinnaiyan, P. et al., "Phase I trial of vorinostat combined with bevacizumab and CPT-11 in recurrent glioblastoma." Neuro Oncol, 2012, vol. 14: 93-100.
Chou, T.C. "Theoretical basis, experimental design, and computerized simulation of synergism and antagonism in drug combination studies." Pharmacol Rev, 2006, vol. 58: 621-81.
Chung, B.H. et al., "Perillyl alcohol inhibits the expression and function of the androgen receptor in human prostate cancer cells." Cancer Lett, 2006, vol. 236: 222-8.
Cookson, M.M. "Prostate cancer: screening and early detection." Cancer Control, 2001, vol. 8: 133-140.
Cunningham, C.C. et al., "Clinical and local biological effects of an intratumoral injection of mda-7 (IL24; INGN 241) in patients with advanced carcinoma: a phase I study." Mol Ther, 2005, vol. 11: 149-159.
da Fonseca, C.O. et al. Ras pathway activation in gliomas: a strategic target for intranasal administration of perillyl alcohol. Arch Immunol TherExp (Warsz), 2008, vol. 56: 267-76.
da Fonseca, C.O. et al., "Efficacy of monoterpene perillyl alcohol upon survival rate of patients with recurrent glioblastoma." J Cancer Res Clin Oncol, 2011, vol. 137: 287-93.
Dai, Y. et al., "Blockade of histone deacetylase inhibitor-induced RelA/p65 acetylation and NF-kappaB activation potentiates apoptosis in leukemia cells through a process mediated by oxidative damage, XIAP downregulation, and c-Jun N-terminal kinase 1 activation." Mol Cell Biol., 2005, vol. 25: 5429-5444.
Damber, J.E. "Prostate cancer." Lancet, 2008, vol. 371: 1710-1721.
Das, S.K. et al., "Chapter One: Cancer terminator viruses and approaches for enhancing therapeutic outcomes." Adv Cancer Res, 2012, vol. 115: 1-38.
Dash et al., "Apogossypol derivative Bl-97C1(Sabutoclax) targeting Mcl-1 sensitizes prostate cancer cells to mda-7/IL-24-mediated toxicity." Proc. Natl. Acad. Sci. USA 108: 8785-8790 (2011).
Dash et al., "Developing an effective gene therapy for prostate cancer: new technologies with potential to translate from the laboratory into the clinic," Discov Med 11: 46-56 (2011).
Dash, R. et al., "Enhanced delivery of mda-7/IL-24 using a serotype chimeric adenovirus (Ad.5/3) improves therapeutic efficacy in low CAR prostate cancer cells." Cancer Gene Ther, 2010, vol. 17: 447-456.
Dash, R. et al., "mda-7 /IL-24: a unique member of the IL-10 gene family promoting cancer-specific toxicity." Cytokine & Growth Factor Rev, 2010, 21: 381-391.
Dash, R. et al., "Mechanism by which Mcl-1 regulates cancer-specific apoptosis triggered by mda-7 /IL-24, an IL-10-related cytokine." Cancer Res, 2010, vol. 70: 5034-5045.
Dent, P. et al., "MDA-7/IL-24 as a cancer therapeutic: from bench to bedside." Anticancer Drugs, 2010, vol. 21: 725-731.
Dent, P. et al., "The development of MDA-7/IL-24 as a cancer therapeutic." Pharmacol Ther., 2010, vol. 128: 375-384.
Dhar, D. et al., "Syrian hamster tumor model to study oncolytic Ad5-based vectors." Methods Mol Biol., 2012, vol. 797: 53-63.
Di Lorenzo, G. et al., "Hormone refractory prostate cancer (HRPC): present and future approaches of therapy." Int J Immunopathol Pharmacol, 2006, vol. 19: 11-34.
Eager, R. et al., "Ad-MDA-7; INGN 241: a review of preclinical and clinical experience." Expert Opin Biol Ther, 2008, vol. 8: 1633-1643.
Ekmekcioglu, S. et al., "Down-regulated melanoma differentiation associated gene (mda-7) expression in human melanomas." Int J Cancer, 2001, vol. 94: 54-59.
Ellerhorst, J.A. et al., "Loss of MDA-7 expression with progression of melanoma." J Clin Oncol, 2002, vol. 20: 1069-1074.
Ellis, L. et al. "Histone Deacetylase Inhibitors: Advancing Therapeutic Strategies in Hematological and Solid Malignancies." Pharmaceuticals (Basel), 2010, vol. 3: 2411-69.
Ellwood-Yen, K. et al., "Myc-driven murine prostate cancer shares molecular features with human prostate tumors." Cancer Cell, 2003, 4: 223-238.
Emanuele, S. et al. "SAHA induces apoptosis in hepatoma cells and synergistically interacts with the proteasome inhibitor Bortezomib." Apoptosis, 2007, vol. 12: 1327-1338.
Emdad, L. et al., "Historical perspective and recent insights into our understanding of the molecular and biochemical basis of the anti tumor properties of mda-7/IL-24." Cancer Biol & Ther, 2009, 8: 391-400.
Emdad, L. et al., "Ionizing radiation enhances adenoviral vector expressing mda-7/IL-24-mediated apoptosis in human ovarian cancer." J Cell Physiol, 2006, vol. 208: 298-306.
Eulitt, P.J., et al., "Enhancing mda-7 /IL-24 therapy in renal carcinoma cells by inhibiting multiple protective signaling pathways using sorafenib and by Ad.5/3 gene delivery." Cancer Biol Ther, 2011, 10: 1290-1305.
Evans, J.D. "Detailed tissue expression of bcl-2, bax, bak and bcl-x in the normal human pancreas and inchronic pancreatitis, ampullary and pancreatic ductal adenocarcinomas." Pancreatology, 2001, vol. 1: 254-62.
Fisher, P.B. et al., "mda-7/IL-24: A novel cancer selective apoptosis inducing cytokine gene: From the laboratory into the clinic." Cancer Biol Therapy, 2003, vol. 2: S23-S37.
Fisher, P.B. et al., "Melanoma differentiation associated gene-7/interleukin-24 (mda-7 /IL-24): novel gene therapeutic for metastatic melanoma." Toxicol & Applied Pharmacol 224: 300-307 (2007).
Fisher. "Is mda-7/IL-24 a 'magic bullet' for cancer" Cancer Res 65: 10128-10138 (2005).
Friday, B.B. et al. "Phase II trial of vorinostat in combination with bortezomib in recurrent glioblastoma: a north central cancer treatment group study." Neuro Oncol., 2012, vol. 14: 215-221.
Friess, H. et al., "Moderate activation of the apoptosis inhibitor bcl-xL worsens the prognosis in pancreatic cancer." Ann Surg, 1998, vol. 228: 780-7.
Galanis, E. et al., "Phase II trial of vorinostat in recurrent glioblastoma multiforme: a north central cancer treatment group study." J Clin Oncol., 2009, 27: 2052-2058.
Gao, P. et al. "Secretable chaperone Grp 170 enhances therapeutic activity of a novel tumor suppressor, mda-7 /IL-24." Cancer Res, 2008, 68: 3890-3898.
Garber, K. China approves world's first oncolytic virus therapy for cancer treatment. J Natl Cancer Inst, 2006, vol. 98: 298-300.

(56) References Cited

OTHER PUBLICATIONS

Gerasimovskaya, E.V. et al., "Activation of phosphatidylinositol 3-kinase, Akt, and mammalian target of rapamycin is necessary for hypoxia-induced pulmonary artery adventitial fibroblast proliferation." J Appl, 2005, vol. 98: 722-31.

Gopalkrishnan, R.V., et al., "Molecular markers and determinants of prostate cancer metastasis." J Cell Physiol, 2001, vol. 189: 245-256.

Greco et al., "Eradication of Therapy-resistant Human Prostate Tumors Using an Ultrasound-guided Site-specific Cancer Terminator Virus Delivery Approach," Mol Ther 18: 295-306 (2010).

Greten, F.R. et al., "Stat3 and NF-kappaB activation prevents apoptosis in pancreatic carcinogenesis." Gastroenterology, 2002, vol. 123: 2052-63.

Gupta, P. et al., "BiP/GRP78 is an intracellular target for MDA-7/IL-24 induction of cancer-specific apoptosis." Cancer Res, 2006, vol. 66: 8182-91.

Gupta, P. et al., "mda-7/IL-24: multifunctional cancer-specific apoptosis-inducing cytokine." Pharmacol Ther, 2006, vol. 111: 596-628.

Hamacher, R. et al., "Apoptotic pathways in pancreatic ductal adenocarcinoma." Mol Cancer, 2008, vol. 7: 64.

Hamed, H.A. et al., "Inhibition of multiple protective signaling pathways and Ad.5/3 delivery enhances mda-7/IL-24 therapy of malignant glioma." Mol Ther, 2010, 18: 1130-1142.

Hamed, H.A. et al., "OSU-03012 enhances Ad.mda-7-induced GBM cell killing via ER stress and autophagy and by decreasing expression of mitochondrial protective proteins." Cancer Biol & Ther, 2010, 9: 526-536.

Hamid, O. et al., "Phase II trial of intravenous Cl-1042 in patients with metastatic colorectal cancer." J Clin Oncol, 2003, vol. 21: 1498-504.

Hinz, S. et al., "Bcl-XL protects pancreatic adenocarcinoma cells against CD95- and TRAIL-receptor-mediated apoptosis." Oncogene, 2000, vol. 19: 5477-86.

Howard, C.M. et al., "Ultrasound guided site specific gene delivery system using adenoviral vectors and commercial ultrasound contrast agents." J Cell Physiol, 2006, 209: 413-421.

Huang, C. et al., "Ultraviolet-induced phosphorylation of p70(S6K) at Thr(389) and Thr(421)/Ser(424) involves hydrogen peroxide and mammalian target of rapamycin but not Akt and atypical protein kinase C." Cancer Res, 2002, vol. 62: 5689-97.

Huang, E.Y. et al., "Genomic structure, chromosomal localization and expression profile of a novel melanoma differentiation associated (mda-7) gene with cancer specific growth suppressing and apoptosis inducing properties." Oncogene, 2001, 20: 7051-7063.

Hudes, G.R. "Phase I pharmacokinetic trial of perillyl alcohol (NSC 641066) in patients with refractory solid malignancies." Clin Cancer Res, 2000, vol. 6: 3071-80.

International Preliminary Report on Patentability for PCT/US2013/073989, dated Jun. 16, 2015.

International Search Report and Written Opinion for PCT/US2013/073989, dated Mar. 31, 2014.

Jiang, H. et al., "Recombinant adenovirus vectors activate the alternative complement pathway, leading to the binding of human complement protein C3 independent of anti-ad antibodies." Mol Ther, 2004, vol. 10: 1140-1142.

Jiang, H. et al., "Subtraction hybridization identifies a novel melanoma differentiation associated gene, mda-7, modulated during human melanoma differentiation, growth and progression." Oncogene, 1995, vol. 11: 2477-2486.

Jiang, H. et al., "The melanoma differentiation associated gene mda-7 suppresses cancer cell growth." Proc. Natl. Acad. Sci. USA 93(17): 9160-9165 (1996).

Jiang, H. et al., "Use of a sensitive and efficient subtraction hybridization protocol for the identification of genes differentially regulated during the induction of differentiation in human melanoma cells." Mol Cell Different 1: 285-299 (1993).

Kahali, S. et al., "Activation of the unfolded protein response contributes toward the antitumor activity of vorinostat." Neoplasia, 2010, vol. 12: 80-86.

Koizumi, N. "Fiber-modified adenovirus vectors decrease liver toxicity through reduced IL-6 production." J Immunol, 2007, vol. 178: 1767-1773.

Lebedeva, I.V. et al., "Bcl-2 and Bcl-x(L) differentially protect human prostate cancer cells from induction of apoptosis by melanoma differentiation associated gene-7, mda-7/IL-24." Oncogene, 2003, vol. 22: 8758-8773.

Lebedeva, I.V. et al., "Chemoprevention by perillyl alcohol coupled with viral gene therapy reduces pancreatic cancer pathogenesis." Mol Cancer Ther, 2008, vol. 7: 2042-50.

Lebedeva, I.V. et al., Induction of reactive oxygen species renders mutant and wild-type K-ras pancreatic carcinoma cells susceptible to Ad.mda-7-induced apoptosis. Oncogene, 2005, 24: 585-96.

Lebedeva, I.V. et al., "mda-7/IL-24, novel anticancer cytokine: focus on bystander antitumor, radiosensitization and antiangiogenic properties and overview of the phase I clinical experience (Review)." Int J Oncol, 2007, vol. 31: 985-1007.

Lebedeva, I.V. et al., "mda-7/IL-24: Exploiting cancer's Achilles' heel." Mol Therapy, 2005, 11: 4-18.

Lee, E.Q., et al., "Phase I study of vorinostat in combination with temozolomide in patients with high-grade gliomas: North American Brain Tumor Consortium Study 04-03." Clin Cancer Res., 2012, vol. 18: 6032-6039.

Liu, G. et al., "Phase II trial of perillyl alcohol (NSC 641066) administered daily in patients with metastatic androgen independent prostate cancer." Invest New Drugs, 2003, vol. 21: 367-72.

Lu, Q.L. et al., "Microbubble ultrasound improves the efficiency of gene transduction in skeletal muscle in vivo with reduced tissue damage." Gene Ther, 2003, vol. 10: 396-405.

McGuire, K.A. et al., "Adenovirus type 5 rupture of lysosomes leads to cathepsin B-dependent mitochondrial stress and production of reactive oxygen species." J Virol, 2011, vol. 85: 10806-13.

McKenzie, T. et al., "Combination therapy of Ad-mda7 and trastuzumab increases cell death in Her-2/neu-overexpressing breast cancer cells." Surgery, 2004, vol. 136: 437-42.

Meadows, S.M. et al., "Phase II trial of perillyl alcohol in patients with metastatic colorectal cancer." Int J Gastrointest Cancer, 2002, vol. 32: 125-8.

Morishima, N. et al., "Translocation of Bim to the endoplasmic reticulum (ER) mediates ER stress signaling for activation of caspase-12 during ER stress-induced apoptosis." J Biol Chem, 2004, vol. 279: 50375-81.

Muruve, D.A. "The innate immune response to adenovirus vectors." Hum Gene Ther, 2004, 15: 1157-1166.

Okegawa, T. et al., "The dual impact of coxsackie and adenovirus receptor expression on human prostate cancer gene therapy." Cancer Research, 2000, vol. 60: 5031-5036.

Pandha, H.S. et al., "Coxsackie Band adenovirus receptor, integrin and major histocompatibility complex class I expression in human prostate cancer cell lines: implications for gene therapy strategies." Prostate Cancer Prostatic Dis, 2003, vol. 6: 6-11.

Park, M.A. et al., "MDA-7/IL-24-induced cell killing in malignant renal carcinoma cells occurs by a ceramide/CD95/PERK-dependent mechanism." Mol Cancer Ther., 2009, vol. 8: 1280-1291.

Pataer, A. et al., Adenoviral endoplasmic reticulum-targeted mda-7/interleukin-24 vector enhances human cancer cell killing. Mol Cancer Ther, 2008, vol. 7: 2528-35.

Paul, C.P. et al., "Characterization of infectivity of knob-modified adenoviral vectors in glioma." Cancer Biol Ther., 2008, vol. 7: 786-793.

Pearson, A.S. et al., "Factors limiting adenovirus-mediated gene transfer into human lung and pancreatic cancer cell lines." Clin Cancer Res, 1999, vol. 5: 4208-13.

Rajesh, D. et al., "Perillyl alcohol as a radio-/chemosensitizer in malignant glioma." J Biol Chem, 2003, vol. 278: 35968-78.

Ripple, G.H. et al., "Phase I clinical trial of perillyl alcohol administered daily." Clin Cancer Res, 1998, vol. 4: 1159-64.

Robins, H.I., et al., "Therapeutic advances for glioblastoma multiforme: current status and future prospects." Curr Oncol Rep, 2007, vol. 9: 66-70.

Rosato, R.R. et al., "Histone deacetylase inhibitors in clinical development." Expert Opin Investig Drugs, 2004, vol. 13: 21-38.

(56) References Cited

OTHER PUBLICATIONS

Ruefli, A.A. et al., "The histone deacetylase inhibitor and chemotherapeutic agent suberoylanilide hydroxamic acid (SAHA) induces a cell-death pathway characterized by cleavage of Bid and production of reactive oxygen species." Proc Natl Acad Sci USA, 2001, vol. 98: 10833-10838.

Sarkar et al., "Chemoprevention gene therapy (CGT): novel combinatorial approach for preventing and treating pancreatic cancer." Curr Mol Med 13(7): 1140-1149 (2012).

Sarkar et al., "Eradication of therapy-resistant human prostate tumors using a cancer terminator virus," Cancer Res 67: 5434-5442 (2007).

Sarkar et al., "Targeted virus replication plus immunotherapy eradicates primary and distant pancreatic tumors in nude mice." Cancer Research 65: 9056-9063 (2005).

Sarkar, D. et al. "A cancer terminator virus eradicates both primary and distant human melanomas." Cancer Gene Therapy, 2008, vol. 15: 293-302.

Sarkar, D. et al. "Dual cancer-specific targeting strategy cures primary and distant breast carcinomas in nude mice." Proc. Natl. Acad. Sci. USA 102: 14034-14039 (2005).

Sarkar, D. et al., "mda-7 (IL-24) Mediates selective apoptosis in human melanoma cells by inducing the coordinated overexpression of the GADD family of genes by means of p38 MAPK." Proc Natl Acad Sci USA, 2002, vol. 99: 10054-10059.

Sarkar, D. et al., "Mda-7 (IL-24): Signaling and functional roles." BioTechniques—Oct. Suppl., 2002, 30-39.

Sarkar, D. et al., "Unique conditionally replication competent bipartite adenoviruses-cancer terminator viruses (CTV): efficacious reagents for cancer gene therapy." Cell Cycle, 2006, vol. 5: 1531-1536.

Sarkar, D., et al., "A cancer terminator virus eradicates both primary and distant human melanomas", Cancer Gene Therapy, 2008, vol. 15, pp. 293-302.

Sarkar, D., et al., "Eradication of therapy-resistant human prostate tumors using a cancer terminator virus", Cancer Res., 2007, vol. 67, No. 11, pp. 5434 and 5442.

Sauane, M. et al., "Autocrine regulation of mda-7 /IL-24 mediates cancer-specific apoptosis." Proc Natl Acad Sci USA, 2008, 105: 9763-9768.

Sauane, M. et al., "Ceramide plays a prominent role in MDA-7/IL-24-induced cancer-specific apoptosis." J Cell Physiol., 2010, vol. 222: 546-555.

Sauane, M. et al., "Mda-7 /IL-24: novel cancer growth suppressing and apoptosis inducing cytokine." Cytokine and Growth Factor Reviews, 2003, vol. 14: 35-51.

Shi, X. et al., "Acquired resistance of pancreatic cancer cells towards 5-Fluorouracil and gemcitabine is associated with altered expression of apoptosis-regulating genes." Oncology, 2002, vol. 62: 354-62.

Siegel et al., "Cancer treatment and survivorship statistics," CA Cancer J Clin, 2012, vol. 62: 220-241.

Spiegel, S. et al., "Endogenous modulators and pharmacological inhibitors of histone deacetylases in cancer therapy." Oncogene, 2012, vol. 31: 537-551.

Stark, M.J. et al., "Chemotherapy of pancreatic cancer with the monoterpene perillyl alcohol." Cancer Lett, 1995,; vol. 96: 15-21.

Sternberg. "Highlights of contemporary issues in the medical management of prostate cancer." Crit Rev Oncol Hematol, 2002, vol. 43: 105-121.

Su, Z. "Targeting gene expression selectively in cancer cells by using the progression-elevated gene-3 promoter," Proc. Natl. Acad. Sci. USA 102: 1059-1064 (2005).

Su, Z. et al. "Progression elevated gene-3, PEG-3, induces genomic instability in rodent and human tumor cells." J Cell Physiol, 2002, vol. 192: 34-44.

Su, Z. et al., "A combinatorial approach for selectively inducing programmed cell death in human pancreatic cancer cells." Proc Natl Acad Sci USA, 2001, vol. 98: 10332-10337.

Su, Z. et al., "PEA3 sites within the progression elevated gene-3 (PEG-3) promoter and mitogen-activated protein kinase contribute to differential PEG-3 expression in Ha-ras and v-raf oncogene transformed rat embryo cells." Nucleic Acids Res, 2001, vol. 29: 1661-1671.

Su, Z. et al., "Subtraction hybridization identifies a transformation progression-associated gene PEG-3 with sequence homology to a growth arrest and DNA damage-inducible gene." Proc Natl Acad Sci USA, 1997, vol. 94: 9125-30.

Su, Z. et al., "The cancer growth suppressor gene mda-7 selectively induces apoptosis in human breast cancer cells and inhibits tumor growth in nude mice." Proc Natl Acad Sci USA 95: 14400-14405.

Su, Z. et al., "Unique aspects of mda-7/IL-24 anti tumor bystander activity: establishing a role for secretion of MDA-7 /IL-24 protein by normal cells." Oncogene 24: 7552-7566 (2005).

Szegezdi, E. et al., "Mediators of endoplasmic reticulum stress-induced apoptosis." EMBO Rep, 2006, vol. 7: 880-5.

Tang, Y. et al., "Sorafenib and HDAC inhibitors synergize to kill CNS tumor cells." Cancer Biol Ther., 2012, vol. 13: 567-574.

Tong, A.W. et al., "Intratumoral injection of INGN 241, a nonreplicating adenovector expressing the melanoma-differentiation associated gene-7 (mda-7/IL24): biologic outcome in advanced cancer patients." Mol Ther 11: 160-172 (2005).

Ungerstedt, J.S. et al., "Role of thioredoxin in the response of normal and transformed cells to histone deacetylase inhibitors." Proc Natl Acad Sci USA, 2005, vol. 102: 673-678.

Wang, H. et al., "Multimerization of adenovirus serotype 3 fiber knob domains is required for efficient binding of virus to desmoglein 2 and subsequent opening of epithelial junctions." J Virol, 2011, vol. 85: 6390-6402.

Webb, J.L. "Effect of more than one inhibitor." Enzyme and Metabolic Inhibitors, 66-79. New York: Academic Press, 1963.

Wei, J. "Bl-97Cl, an optically pure Apogossypol derivative as pan-active inhibitor of antiapoptotic B-cell lymphoma/leukemia-2 (Bcl-2) family proteins." J Med Chem, 2010, vol. 53: 4166-4176.

Wei, J. et al., "Apogossypol derivatives as pan-active inhibitors of antiapoptotic B-cell lymphoma/leukemia-2 (Bcl-2) family proteins." J Med Chem, 2009, 52: 4511-4523.

Westphal, S. et al., "Apoptosis: targets in pancreatic cancer." Mol Cancer, 2003, vol. 2: 6.

Wolk, K. et al., "Cutting edge: immune cells as sources and targets of the IL-10 family members?" J Immunol, 2002, vol. 168: 5397-5402.

Wu, J. et al., "From acute ER stress to physiological roles of the Unfolded Protein Response." Cell Death Differ, 2006, vol. 13: 374-84.

Yacoub, A. et al., "Caspase, cathepsin-, and PERK-dependent regulation of MDA-7 /IL-24-induced cell killing in primary human glioma cells." Mol Cancer Ther., 2008, vol. 7: 297-313.

Yacoub, A. et al., "Cisplatin enhances protein kinase R-like endoplasmic reticulum kinase- and CD95-dependent melanoma differentiation-associated gene-7 /interleukin-24-induced killing in ovarian carcinoma cells." Mol Pharmacol, 2010, vol. 77: 298-310.

Yacoub, A. et al., "MDA-7/IL-24 plus radiation enhance survival in animals with intracranial primary human GBM tumors." Cancer Biol Ther, 2008, vol. 7: 917-933.

Yacoub, A. et al., "PERK-dependent regulation of ceramide synthase 6 and thioredoxin play a key role in mda-7 /IL-24-induced killing of primary human glioblastoma multiforme cells." Cancer Res., 2010, vol. 70: 1120-1129.

Yacoub, A. et al., "Regulation of GST-MDA-7 toxicity in human glioblastoma cells by ERBBI, ERKI/2, PI3K, and JNKI-3 pathway signaling." Mol Cancer Ther., 2008, vol. 7: 314-329.

Zhou, Y.P. "Overexpression of Bcl-x(L) in beta-cells prevents cell death but impairs mitochondrial signal for insulin secretion." Am J Physiol Endocrinol Metab, 2000, vol. 278: E340-51.

* cited by examiner $IC_{50} > 88.26 \pm 3.55$ (Ad.5-CTV-M7)
$IC_{50} > 53.19 \pm 2.18$ (Ad.5/3-CTV-M7)

$IC_{50} > 198.00 \pm 7.12$ (Ad.5-CTV-M7)
$IC_{50} > 43.28 \pm 3.15$ (Ad.5/3-CTV-M7)

Hamster
Neck lymph nodes

DNA Sequences in Ad5/3-CTV
SEQ ID NO.1; PEG3-E1

```
TTTGGATTGAAGCCAATATGATAATGAGGGGGTGGAGTTTGTGACGTGGCGCGGGCGTG   Ad5 left ITR
GGAACGGGGCGGGTGACGTAGTAGTGTGGGCGGAAGTGTGATGTTGCAAGTGTGGCGGAAC  and
ACATGTAAGCGACGGATGTGGCAAAAGTGACGTTTTTGGTGTGCGCCGGTGTACACAGGA   packaging signal
AGTGACAATTTCGCGCGGTTTTAGCCGGAATTGTGTAGTAAATCTGAATAATTTGT
AGATTGGCCATTTCGGGAAAATCTGAATGTGAATCTGAATAATTTGT
GTTACTCATAGCGCGTAATATTTGTCTAGGGATCTGAGCAGCAGAAGAGAACATA        PEG promoter
GAGAATGGGACAGCATGTCACGTCCCTGATGAATGAAGTTGGGCTGCTCAAAGTCTGCG
AGATTCACGCCTCTCGATTTGCAGGAGAATTAGCAGGACGTGTTCAGTGTCTTCCTCAC
AAGGCCCCGAAGATTCCGGAGAATTCAGTGTTCCCTCTCCACCCTTCTCAGGG
ACTTCCGAAACTCCCCGCGCCCCGCATAGCGCCACGAGCCCTTACC                CACGAGT
GGCCATCGATTCGACGTGTATTTATACCGAGTTCCTCAAGAGGCCACTCTTGAGTG     start of E1a cds
CCAGCGAGTAGAGTTTTTCTCCGAGACCGCCTCCGACACCGGGAAATCACACAATA
TTATCTGCCACGGAGGTGTATATCGGAGCCGAAGAATCGGCCGAAGTCTTTGACCAGCTGA
ACGAAGTACTGGCTATATCTGCCATAAATCTTCCACCCTCCTACCCTACCCTCC
ACGAACTGTATGATCTTAGAGCTGACGTGACGGCCCACACCCACAACGAGGAGGGGGTTTCGC
AGATTTTCCCGACTCTGTAATGTTGGGGTGCAGGAAG
```

*Figure 26A*

DNA Sequences in Ad5/3-CTV
SEQ ID NO.2: CMVpromoter-mda7-bGH pA

Ad5 -CCACATGGTGGCAGATGCTGCATTCGAAAACGTTTGAATTGATAATT
ATTATCATTTGCGGGTCCTTTCCGGCGATCCGCCTTGTTACGGGGCGGCG
ACCTCGCGGGTTTTCGCTATTTATGAAAATTTTCCGGTTTAAGGCGTTTC
CGTTCTTCTTCGTCATAACTTAATGTTTTTATTTAAAATACCCTCTGAAA
AGAAAGGAAACGACAGGATCTTCTAGACCCGGGAGCGGCCGCTGTCGACA
TTGATTATTGACTAGTTATTAATAGTAATCAATTACGGGGTCATTAGTTC
ATAGCCCATATATGGAGTTCCGCGTTACATAACTTACGGTAAATGGCCCG
CCTGGCTGACCGCCCAACGACCCCCGCCCATTGACGTCAATAATGACGTA
TGTTCCCATAGTAACGCCAATAGGGACTTTCCATTGACGTCAATGGGTGG
AGTATTTACGGTAAACTGCCCACTTGGCAGTACATCAAGTGTATCATATG CMV promoter
CCAAGTACGCCCCCTATTGACGTCAATGACGGTAAATGGCCCGCCTGGCA
TTATGCCCAGTACATGACCTTATGGGACTTTCCTACTTGGCAGTACATCT
ACGTATTAGTCATCGCTATTACCATGGTGATGCGGTTTTGGCAGTACATC
AATGGGCGTGGATAGCGGTTTGACTCACGGGGATTTCCAAGTCTCCACCC
CATTGACGTCAATGGGAGTTTGTTTTGGCACCAAAATCAACGGGACTTTC
CAAAATGTCGTAACAACTCCGCCCCATTGACGCAAATGGGCGGTAGGCGT
GTACGGTGGGAGGTCTATATAAGCAGAGCTCTCTGGCTAACTAGAGAACC
CACTGCTTACTGGCTTATCCAAATTAATACGACTCACTATAGGGAGACCC
AAGCTGGCTAGCGTTTAAACTTAAGCTTGGTACCGAGCTCGGATCCACTA
GTAACGGCCGCCAGTGTGCTGGAACTCGGCTTACAAGACATGACTGTGAT
GAGGAGCTGCTTTCGCCAATTTAACACCAAGAAGAATTGAGGCTGCTTGG
GAGGAAGGCCAGGAGGAACACGAGACTGAGAGATGAATTTTCAACAGAGG
CTGCAAAGCCTGTGGACTTTAGCCAGACCCTTCTGCCCTCCTTTGCTGGG
GACAGCCTCTCAAATGCAGATGGTTGTGCTCCCTTGCCTGGGTTTTACCC
TGCTTCTCTGGAGCCAGGTATCAGGGGCCCAGGGCCAAGAATTCCACTTT
GGGCCCTGCCAAGTGAAGGGGGTTGTTCCCCAGAAACTGTGGGAAGCCTT
CTGGGCTGTGAAAGACACTATGCAAGGTCAGGATAAGATCACGAGTGCCC mda7 cds
GGCTGCTGCAGCAGGAGGTTCTGCAGAACGTCTCGGATGCTGAGAGCTGT
TACCTTGTCCACACCCTGCTGGAGTTCTACTTGAAAACTGTTTTCAAAAA
CTACCACAATAGAACAGTTGAAGTCAGGACTCTGAAGTCATTCTCTACTC
TGGCCAACAACTTTGTTCTCATCGTGTCACAACTGCAACCCAGTCAAGAA
AATGAGATGTTTTCCATCAGAGACAGTGCACACAGGCGGTTCCTGCTATT
CCGGAGAGCATTTAAACAGTTGGACGTAGAAGCAGCTCTGACCAAAGCCC
TTGGGGAAGTGGACATTCTTCTGACCTGGATGCAGAAACTCTACAAGCTC
TGAATGTCTAGACCAGGACCTCCCTCCCCCTGGCACTGGTTTGTTCCCTG
TGTCATTTCAAACAGTCTAAGCCGAATTCTGCAGATATCCATCACACTGG
CGGCCGCTCGAGTCTAGAGGGCCCGTTTAAACCCGCTGATCAGCCTCGAC
TGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAG bGH pA
GAAATTGCATCGCATTGTCTGAGTAGGTGTCATTCTATTCTGGGGGGTGG
GGTGGGGCAGGACAGCAAGGGGGAGGATTGGGAAGACAATAGCAGGCATG
CTGGGGATGCGGTGGGCTCTATGGCTTCGCGGCCGCAATCACTAGTGAAT
TCGCGGCCGCCTGCAGGTCGGATCCGAATTCGATATCACTAGTGGTACCC
ACCCAGTGG- Ad5

*Figure 26B*

DNA Sequences in Ad5/3-CTV
SEQ ID NO.3; Ad5/3 fiber

```
tggaatgtcagtttcctcctgttcctgtccatccgcacccactatcttcatgttgttgca
         10        20        30        40        50        60
----:----|----:----|----:----|----:----|----:----|----:----|
Ad5 Fiber start codon
gatgaagcgcgcaagaccgtctgaagataccttcaaccccgtgtatccatatgacacgga
         70        80        90       100       110       120
----:----|----:----|----:----|----:----|----:----|----:----|
   M  K  R  A  R  P  S  E  D  T  F  N  P  V  Y  P  Y  D  T  E
aaccggtcctccaactgtgccttttcttactcctccctttgtatcccccaatgggtttca
        130       140       150       160       170       180
----:----|----:----|----:----|----:----|----:----|----:----|
   T  G  P  P  T  V  P  F  L  T  P  P  F  V  S  P  N  G  F  Q
agagagtcccccctggggtactctctttgcgcctatccgaacctctagttacctccaatgg
        190       200       210       220       230       240
----:----|----:----|----:----|----:----|----:----|----:----|
   E  S  P  P  G  V  L  S  L  R  L  S  E  P  L  V  T  S  N  G
catgcttgcgctcaaaatgggcaacggcctctctctggacgaggccggcaaccttacctc
        250       260       270       280       290       300
----:----|----:----|----:----|----:----|----:----|----:----|
   M  L  A  L  K  X  G  N  G  L  S  L  D  E  A  G  N  L  T  S
ccaaaatgtaaccactgtgagcccacctctcaaaaaaaccaagtcaaacataaacctgga
        310       320       330       340       350       360
----:----|----:----|----:----|----:----|----:----|----:----|
   Q  N  V  T  T  V  S  P  P  L  K  K  T  K  S  N  I  N  L  E
aatatctgcacccctcacagttacctcagaagccctaactgtggctgccgccgcacctct
        370       380       390       400       410       420
----:----|----:----|----:----|----:----|----:----|----:----|
   I  S  A  P  L  T  V  T  S  E  A  L  T  V  A  A  A  A  P  L
aatggtcgcgggcaacacactcaccatgcaatcacaggccccgctaaccgtgcacgactc
        430       440       450       460       470       480
----:----|----:----|----:----|----:----|----:----|----:----|
   M  V  A  G  N  T  L  T  M  Q  S  Q  A  P  L  T  V  H  D  S
```

Figure 26C

DNA Sequences in Ad5/3-CTV
SEQ ID NO.3; Ad5/3 fiber (continued)

```
caaacttagcattgccacccaaggacccctcacagtgtcagaaggaaagctagccctgca
        490       500       510       520       530       540
----:----|----:----|----:----|----:----|----:----|----:----|
   K  L  S  I  A  T  Q  G  P  L  T  V  S  E  G  K  L  A  L  Q
aacatcaggccccctcaccaccaccgatagcagtacccttactatcactgcctcacccc
        550       560       570       580       590       600
----:----|----:----|----:----|----:----|----:----|----:----|
   T  S  G  P  L  T  T  T  D  S  S  T  L  T  I  T  A  S  P  R
tctaactactgccactggtagcttgggcattgacttgaaagagcccatttatacacaaaa
        610       620       630       640       650       660
----:----|----:----|----:----|----:----|----:----|----:----|
   L  T  T  A  T  G  S  L  G  I  D  L  K  E  P  I  Y  T  Q  N
tggaaaactaggactaaagtacggggctcctttgcatgtaacagacgacctaaacacttt
        670       680       690       700       710       720
----:----|----:----|----:----|----:----|----:----|----:----|
   G  K  L  G  L  K  Y  G  A  P  L  H  V  T  D  D  L  N  T  L
gaccgtagcaactggtccaggtgtgactattaataatacttccttgcaaactaaagttac
        730       740       750       760       770       780
----:----|----:----|----:----|----:----|----:----|----:----|
   T  V  A  T  G  P  G  V  T  I  N  N  T  S  L  Q  T  K  V  T
tggagccttgggctttgattcacaaggcaatatgcaacttaatgtagcaggaggactaag
        790       800       810       820       830       840
----:----|----:----|----:----|----:----|----:----|----:----|
   G  A  L  G  F  D  S  Q  G  N  M  Q  L  N  V  A  G  G  L  R
gattgattctcaaaacagacgccttatacttgatgttagttatccgtttgatgctcaaaa
        850       860       870       880       890       900
----:----|----:----|----:----|----:----|----:----|----:----|
   I  D  S  Q  N  R  R  L  I  L  D  V  S  Y  P  F  D  A  Q  N
ccaactaaatctaagactaggacagggccctctttttataaactcagcccacaacttgga
        910       920       930       940       950       960
----:----|----:----|----:----|----:----|----:----|----:----|
   Q  L  N  L  R  L  G  Q  G  P  L  F  I  N  S  A  H  N  L  D
tattaactacaacaaggcctttacttgtttacagcttcaaacaattccaaaaagcttga
        970       980       990      1000      1010      1020
----:----|----:----|----:----|----:----|----:----|----:----|
   I  N  Y  N  K  G  L  Y  L  F  T  A  S  N  N  S  K  K  L  E
```

Figure 26D

DNA Sequences in Ad5/3-CTV
SEQ ID NO. 3; Ad5/3 fiber (continued)

```
ggttaacctaagcactgccaaggggttgatgtttgacgctacagccatagccattaatgc
         1030       1040       1050       1060       1070       1080
----:----|----:----|----:----|----:----|----:----|----:----|
 V  N  L  S  T  A  K  G  L  M  F  D  A  T  A  I  A  I  N  A aggagatgggcttgaatttggttcacctaatgcaccaaacacaaatcccctcaaaacaaa
         1090       1100       1110       1120       1130       1140
----:----|----:----|----:----|----:----|----:----|----:----|
 G  D  G  L  E  F  G  S  P  N  A  P  N  T  N  P  L  K  T  K aattggccatggcctagaatttgattcaaacaaggctatggttcctaaactaggaactgg
         1150       1160       1180       1170       1190       1200
----:----|----:----|----:----|----:----|----:----|----:----|
 I  G  H  G  L  R  F  D  S  N  K  A  M  V  P  K  L  G  T  G ccttagttttgacagcacaggtgccattacagtaggaaacaaaaataatgataagctaac
         1210       1220       1230       1240       1250       1260
----:----|----:----|----:----|----:----|----:----|----:----|
 L  S  F  D  S  T  G  A  I  T  V  G  N  K  N  N  D  K  L  T cctatggacagctccaaaaccagaagccaactgcataattgaatacgggaaacaaaaccc
         1270       1280       1290       1300       1310       1320
----:----|----:----|----:----|----:----|----:----|----:----|
 L  W  T  G  P  K  P  E  A  N  C  I  I  E  Y  G  K  Q  N  P agatagcaaactaacttttaatcttgtaaaaaatggaggaattgttaatggatatgtaac
         1330       1340       1350       1360       1370       1380
----:----|----:----|----:----|----:----|----:----|----:----|
 D  S  K  L  T  L  I  L  V  K  N  G  G  I  V  N  G  Y  V  T gctaatgggagcctcagactacgttaacactttatttaaaaacaaaaatgtctccattaa
         1390       1400       1410       1420       1430       1440
----:----|----:----|----:----|----:----|----:----|----:----|
 L  M  G  A  S  D  Y  V  N  T  L  F  K  N  K  N  V  S  I  N tgtagaactatacttgatgccactggtcatatattaccagactcatcttctcttaaaac
         1450       1460       1470       1480       1490       1500
----:----|----:----|----:----|----:----|----:----|----:----|
 V  E  L  Y  F  D  A  T  G  H  I  L  P  D  S  S  S  L  K  T agatctagaactaaaatacaagcaaacggctgactttagtgcaagaggttttatgccaag
         1510       1520       1530       1540       1550       1560
----:----|----:----|----:----|----:----|----:----|----:----|
 D  L  E  L  K  Y  K  Q  T  A  D  F  S  A  R  G  F  M  P  S
```

*Figure 26E*

DNA Sequences in Ad5/3-CTV
SEQ ID NO. 3; Ad5/3 fiber (continued)

```
tactacagcgtatccattgtccttcctaatgcgggaacacataatgaaaattatatttt
         1570      1580      1590      1600      1610      1620
    ----:----|----:----|----:----|----:----|----:----|----:----|
     T  T  A  Y  P  F  V  L  P  N  A  G  T  H  N  E  N  Y  I  F ggtcaatgctactacaaagcaagcgatggtgccctttttccgttggaagttactgttat
         1630      1640      1650      1660      1670      1680
    ----:----|----:----|----:----|----:----|----:----|----:----|
     G  Q  C  Y  Y  K  A  S  D  G  A  L  F  P  L  E  V  T  V  M gcttaataaacgcctgccagatagtcgcacatcctatgttatgacttttttattggtcctt
         1690      1700      1710      1720      1730      1740
    ----:----|----:----|----:----|----:----|----:----|----:----|
     L  N  K  R  L  P  D  S  R  T  S  Y  V  M  T  F  L  W  S  L gaatgctggtctagctccagaaactactcaggcaaccctcataacctccccatttaccctt
         1750      1760      1770      1780      1790      1800
    ----:----|----:----|----:----|----:----|----:----|----:----|
     N  A  G  L  A  P  E  T  T  Q  A  T  L  I  T  S  P  F  T  F ttcctatattagagaagatgactaataaactctaaagaatcgtttgtgttatgtttcaac
         1810      1820      1830      1840      1850      1860
    ----:----|----:----|----:----|----:----|----:----|----:----|
     S  Y  I  R  E  D  D    *  *  -  -  -  -  -  -  -  -  -  - gtgtttattttcaattgcagaaaatttcaagtcattttttcattcagtagtatagcccca
         1870      1880      1890      1900      1910      1920
    ----:----|----:----|----:----|----:----|----:----|----:----|
     -  -  -  -  -  -  -  -  -  -  -  -  -  -  -  -  *  -  - ccaccacatagcttatacagatcaccgtaccttaatcaaactcacagaaccctagtattc
         1930      1940      1950      1960      1970      1980
    ----:----|----:----|----:----|----:----|----:----|----:----|
     -  -  -  -  -  -  -  -  -  -  -  -  -  -  -  -  *  -  - aacctgccacctccctcccaacacacagagtacacagtcctttctccccggctggcctta
         1990      2000      2010      2020      2030      2040
    ----:----|----:----|----:----|----:----|----:----|----:----|
     -  -  -  -  -  -  -  -  -  -  -  -  -  -  -  -  -  -  * aaaagcatcatatcatgggtaacagacatattcttaggtgttatattccacacggtttcc
         2050      2060      2070      2080      2090      2100
    ----:----|----:----|----:----|----:----|----:----|----:----|
     -  -  -  -  -  *  -  -  -  -  -  *  -  -  -  -  -  -  -
```

*Figure 26F*

DNA Sequences in Ad5/3-CTV
SEQ ID NO.3; Ad5/3 fiber (continued)

```
tgtcgagccaaacgctcatcagtgatattaataaactccccgggcagctcacttaagttc
         2110      2120      2130      2140      2150      2160
----:----|----:----|----:----|----:----|----:----|----:----|
  -   -   -   -   -   -   *   -   *   *   -   -   -   -   -   - atgtcgctgtccagctgctgagccacaggctgctgtccaacttgcggttgcttaacgggc
         2170      2180      2190      2200      2210      2220
----:----|----:----|----:----|----:----|----:----|----:----|
  -   -   -   -   -   -   -   -   -   -   -   -   -   *   -   - ggcgaaggagaagtccacgcctacatgggggtagagtcataatcgtgcatcaggataggg
         2230      2240      2250      2260      2270      2280
----:----|----:----|----:----|----:----|----:----|----:----|
  -   -   -   -   -   -   -   -   *   -   -   -   -   -   *   - gtggtgctgcagcagcgcgcgaataaactgcttgcggccgcggctccgtcctgcagga
         2290      2300      2310      2320      2330      2340
----:----|----:----|----:----|----:----|----:----|----:----|
  -   -   -   -   -   -   -   *   -   -   -   -   -   -   - atacaacatggcagtgg
         2350      2360      2370      2380      2390      2400
----:----|----:----|----:----|----:----|----:----|----:----|
  -   -   -   -   -   -    (SEQ ID NO: 6)
```

TROPISM MODIFIED CANCER TERMINATOR VIRUS (AD.5/3 CTV;AD.5/3-CTV-M7)

CROSS REFERENCE TO RELATED APPLICATIONS

This application is the U.S. National Stage of International Application PCT/US2013/073989, filed Dec. 10, 2013, which claims priority to U.S. Provisional Application 61/735,177, filed Dec. 10, 2012, which are incorporated herein by reference in their entireties.

GOVERNMENT FUNDING

This invention was made with government support under the contract P01 CA194166 and R01 CA097318 awarded by the National Institute of Health/NCI. The government has certain rights in the invention.

SEQUENCE LISTING

The instant application contains a Sequence Listing which has been submitted electronically in ASCII format and is hereby incorporated by reference in its entirety. Said ASCII copy, created on Aug. 31, 2015, is named $110551\text{-}0125_{13}$ SL.txt and is 13,767 bytes in size.

BACKGROUND OF THE INVENTION

Field of the Invention

The invention generally relates to improved methods of adenoviral cancer therapy. In particular, the invention provides adenoviral vectors that are Coxsackie Adenoviral Receptor (CAR) independent, cancer-specific in their replication and produce a systemically active anti-cancer cytokine.

Background

Adenoviral vectors have shown great promise with respect to the delivery and expression of therapeutic agents to cells. However, to date, the level of infectivity, and hence the efficacy, of adenoviral vectors is determined by the presence, in the targeted cells, of Coxsackie Adenoviral Receptors (CARs), which mediate viral entry into the cell. In this regard, it is particularly unfortunate that many types of cancer cells express low or no appreciable levels of CARs. This feature of cancer cells severely curtails the otherwise promising use of adenoviral vectors as anticancer agents. Additionally, an ability to selectively replicate in cancer cells and also produce a therapeutically active and safe secreted cytokine will limit non-specific toxicity and allow for treatment of both primary infected tumors and distant infected or non-infected metastases.

SUMMARY

The invention provides a novel chimeric tropism modified adenoviral vector, Ad.5/3-CTV (Ad.5/3-CTV-M7) that displays profound anti-cancer activity in human cancer cells. Significantly, this chimera infects cancer cells in a CAR-independent manner, i.e., the anticancer agents encoded by this adenoviral construct are expressed in both high and low CAR cancer cells. As demonstrated herein, Ad.5/3-CTV (Ad.5/3-CTV-M7) displays enhanced anti-tumor activity in vitro and in vivo in xenograft tumors in nude mice in low CAR prostate cancer, glioma (GBM), renal cancer and colorectal cancer.

Ad.5/3-CTV (Ad.5/3-CTV-M7) is a new cancer terminator virus, which may be used to treat a wide variety of cancers. Ad.5/3-CTV (Ad.5/3-CTV-M7) exhibits enhanced infectivity compared with other cancer terminator viruses, e.g., viruses where adenoviral replication is controlled by the cancer-selective Progression Elevated Gene-3 (PEG-3) promoter and which simultaneously express an anticancer cytokine, such as melanoma differentiation associated gene-7/Interleukin-24 (mda-7/IL-24) from the E3 region of the adenovirus. Ad.5/3-CTV (Ad.5/3-CTV-M7) may be administered by a variety of routes particularly including systemic administration, alone or in combination with one more therapeutic agents (e.g., additional anticancer agents), together with a carrier (e.g., aqueous fluid). Very good in vivo delivery results are achieved when delivering Ad.5/3-CTV (Ad.5/3-CTV-M7) associated with perfluorocarbon microbubbles as a carrier, where, after arrival at or near the cancer tissue and its associated tumor vasculature, the microbubbles are burst by exposure to ultrasound (This approach is called ultrasound-targeted microbubble-destruction (UTMD)). Particularly good results may be achieved in specific cancers when the mda-7/IL-24 therapeutic gene product from the Ad.5/3-CTV (Ad.5/3-CTV-M7) is combined with agents that augment reactive oxygen species (ROS) production, such as limonene and perillyl alcohol. For example, these agents which augment ROS production enhance the therapeutic index of mda-7/IL-24 in pancreatic cancer cells. Combining mda-7/IL-24 produced from Ad.5/3-CTV (Ad.5/3-CTV-M7) with HDAC inhibitors such as SAHA or sodium valproate represent another way of enhancing therapeutic activity of mda-7/IL-24. The use of sabutoclax (an exemplary MCL-1 inhibitor) with the Ad.5/3-CTV (Ad.5/3-CTV-M7) enhances its activity against prostate and other cancers. Obatoclax (an exemplary Bcl-2 and Bcl-xL inhibitor) should confer increased lethality to GBM cells when combined with Ad.5/3-CTV (Ad.5/3-CTV-M7). In addition, enhanced survival is achieved when Ad.5/3-CTV (Ad.5/3-CTV-M7) is used in combination with vorinostat (Zolinda) compared to either Ad.5/3-CTV (Ad.5/3-CTV-M7) or vorinostat alone.

Changes in BiP/GRP78, GRP94 and activation of PARP were detected by Western blot analysis after 2 days of treatment of PC-3 cells with the indicated Ads. b+c) Cell proliferation and viability using the MTT assay was quantified after 6 days with the indicated doses of vp/cell of Ad.5-CTV (Ad.5-CTV-M7), Ad.5/3-CTV (Ad.5/3-CTV-M7) and their respective controls. Results are the mean±S.D. (n=3). *, P<0.05 with the Ad.5-vec 10000 vp/cell infected group.

FIG. 4A-E. Ad.5/3-CTV (Ad.5/3-CTV-M7) eradicates primary and inhibits distant PC-3-Bcl-2 xenografts in nude mice. Tumor xenografts with PC-3-Bcl-2 cells were established in athymic nude mice in both right and left flanks; and only tumors on the left side were injected with the indicated Ads over a 4-week period (total of nine injections). Measurements of PC-3-Bcl-2 xenograft tumor volumes on A) left and B) right flanks; points, average (with a minimum of five mice in each group); bars, ±S.D. Inset contains a photograph of the animals of each representative group. C) Photograph of the PC-3-Bcl-2 xenograft tumor at the end of the study. D) Measurement of tumor weight at the end of the study; columns, mean (with at least five mice in each group); bars, ±S.D. E) Western blot analysis of protein extracts from representative PC-3-Bcl-2 tumor samples treated with Ad.5-vec, Ad.5/3-vec, Ad.5-PEG-E1A, Ad.5/3-PEG-E1A, Ad.5-CTV (Ad.5-CTV-M7), Ad.5/3-CTV (Ad.5/3-CTV-M7). The immunoblot was reacted with anti-MDA-7/IL-24.

Figure 5A:
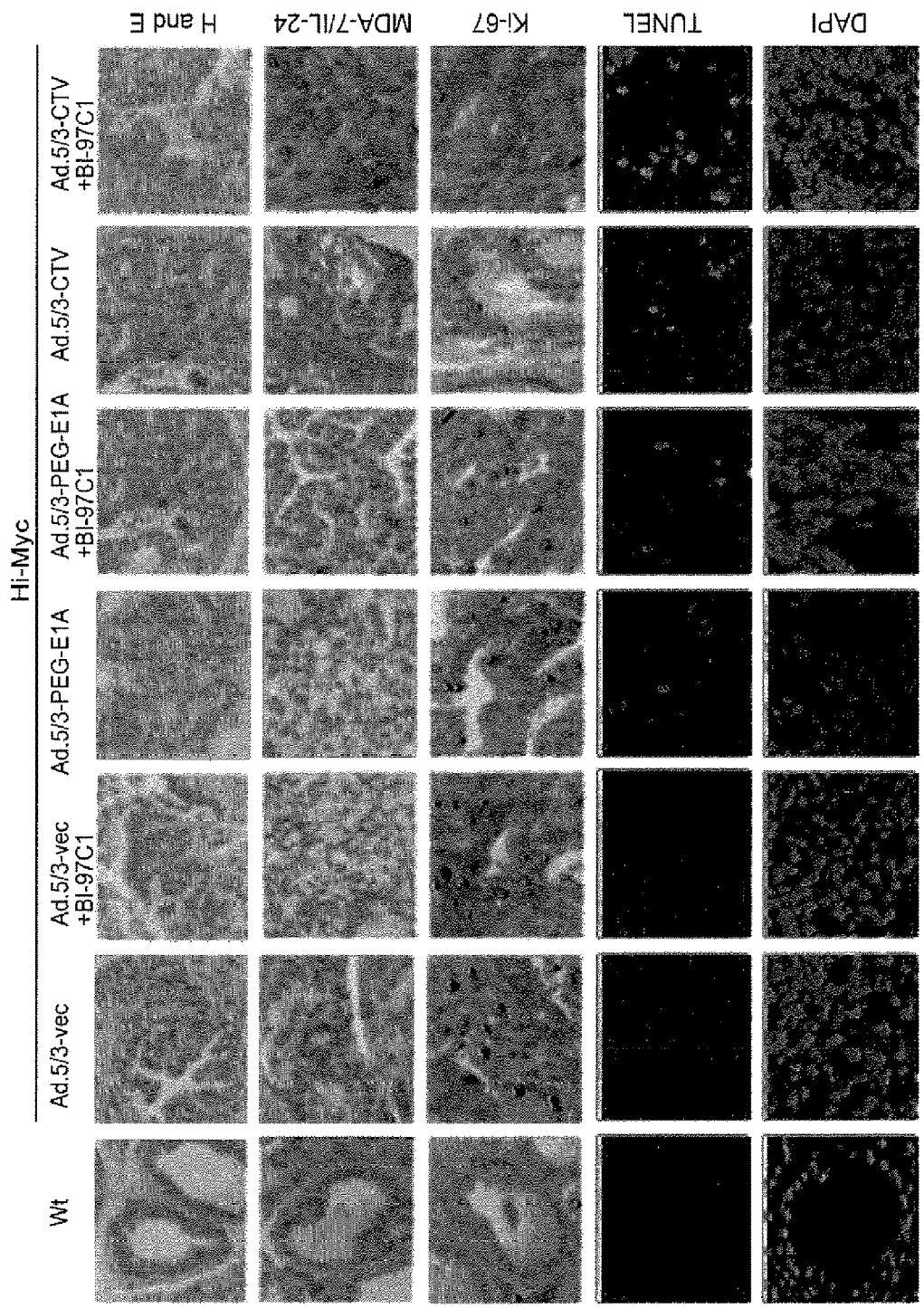
Figure 5B:
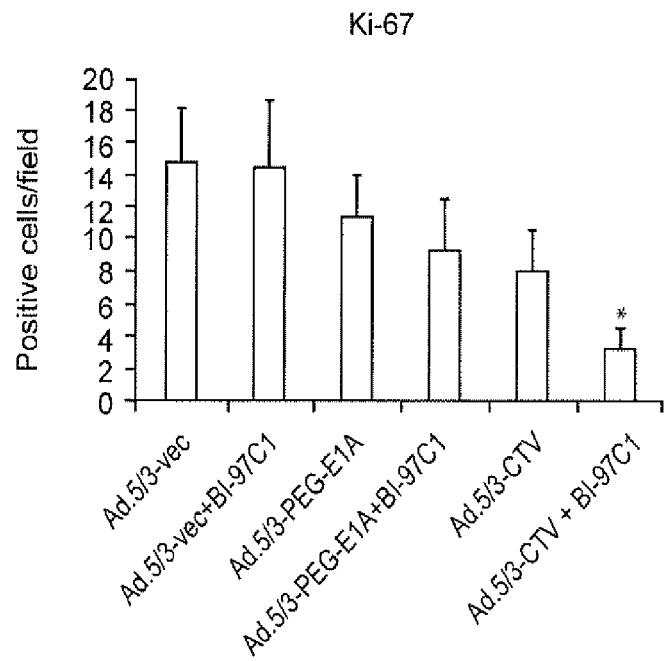
Figure 5C:
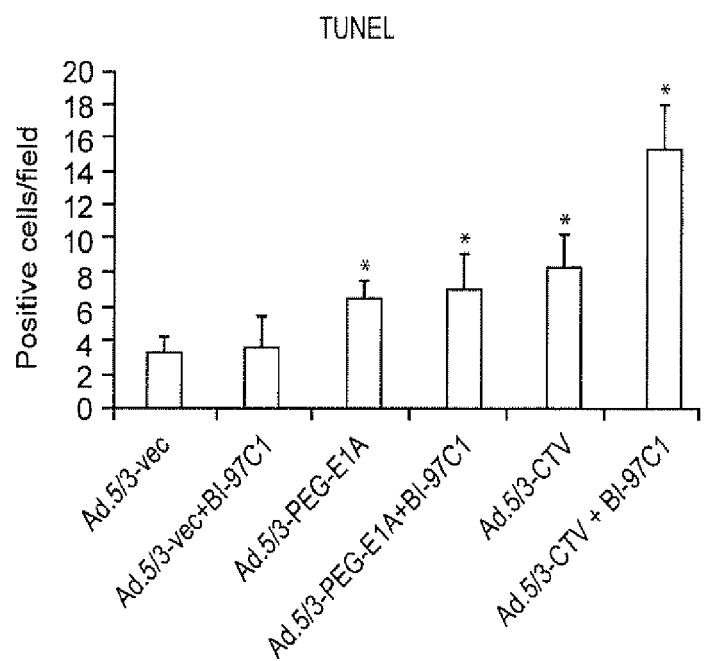

FIG. 5A-C: Combination treatment of Ad.5/3-CTV (Ad.5/3-CTV-M7) and BI-97C1 (Sabutoclax) potentiates inhibition of prostate tumor growth in vivo in immune competent animals. A): The prostatic region of 22 week-old male Hi-Myc mice were sonoporated for 10 min following tail-vein injection of the indicated complement-treated microbubble/Ad complexes and treated as described in the materials and methods section for 4 weeks (total 8 injections of indicated viruses). BI-97C1 (Sabutoclax) was administered intraperitoneally (i.p.) in each group at 3 mg/kg 3× a week throughout the study. At the end of the experiment the mice were sacrificed and the prostates were collected. The paraffin-embedded sections were obtained from the prostate and immunohistochemistry was performed to measure systemic transgene delivery by staining with anti-MDA-7/IL-24. TUNEL assay and Ki-67 staining detected apoptosis and cell proliferation in the prostate sections. Nuclei were visualized with DAPI. Wild type mice of the same strain that do not develop prostate cancer served as a control for these experiments. B) Quantification of microvessel density in prostate section per field followed by Ki-67 staining and C) Quantification of TUNEL positive signals in the prostate section (*P<0.05 between the indicated groups). Data represent mean±S.D. (n=3).

FIG. 6A-D. PEG-Prom is selectively more active in pancreatic cancer cells than normal LT-2 cell lines. A) Pancreatic cells were treated with Ad.PEG-GFP at 5000 vp/cell and then incubated for additional 48 h for its expression. (A) Images were taken with a 20× magnification lens under a fluorescent microscope. (B) Cells treated with Ad.vec (solid filled black line) or Ad.PEG-GFP (solid red line) were collected and GFP-expression was measured using a flow-cytometer. (C) The relative expressed GFP or fluorescence values (RFU; Ad.5.PEG-GFP/Ad.5.CMV-GFP) were quantified using FacsDIVA software. (D) Relative Luminescence units (RLU) of pGL3.PEG-luc/pGL3.CMV-luc after transfecting the cells with pGL3.PEG-luc and pGL3.CMV-luc. ***, p<0.001 versus RFU of infected or RLU of transfected LT-2. The data represents mean±S.E of three different experiments.

Figures 7A, 7B:
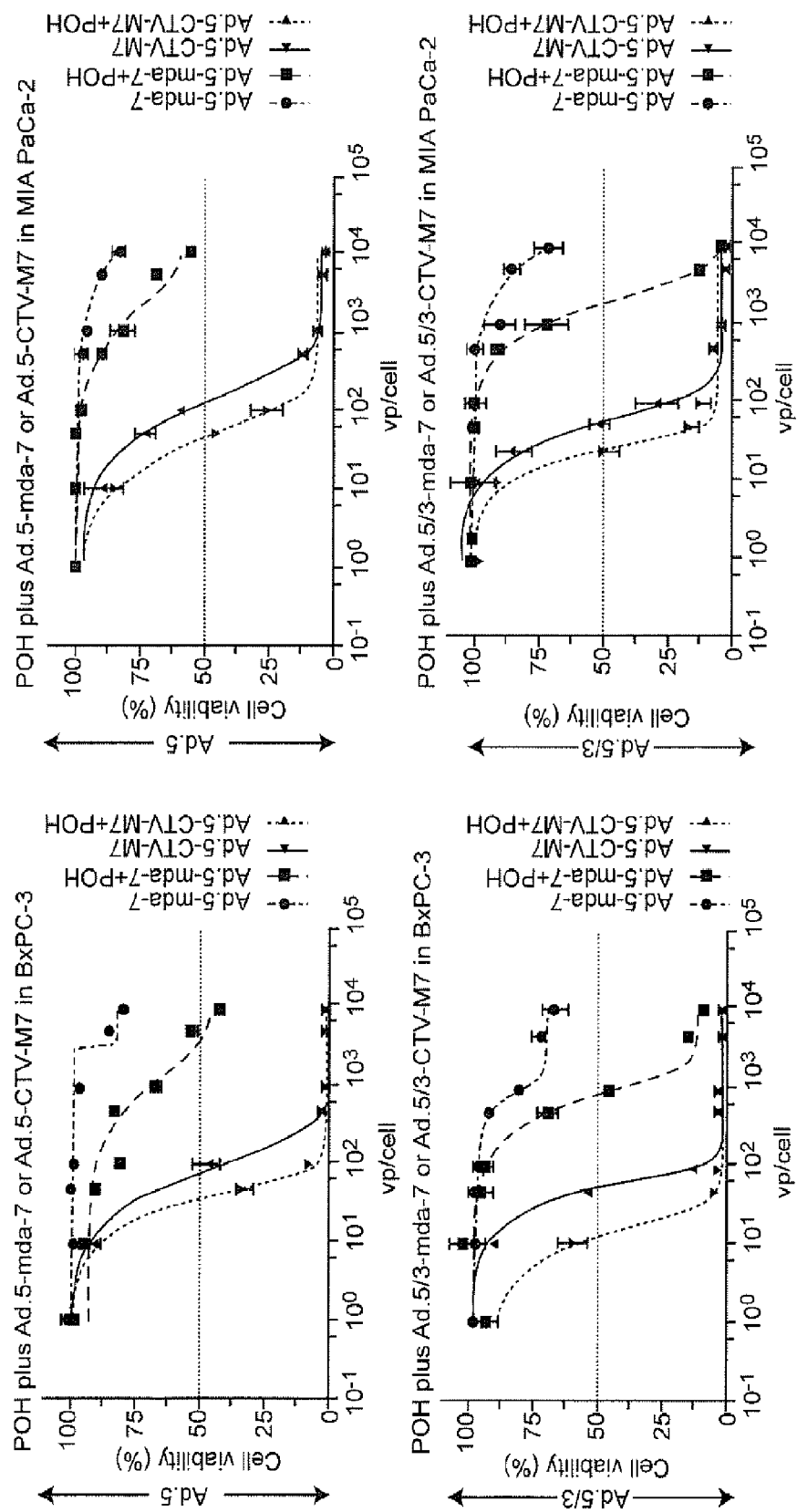

FIGS. 7A and B. Ad.5-PEG-E1A-mda-7 (Ad.5-CTV-M7) or Ad.5/3-PEG-E1A-mda-7 (Ad.5/3-CTV-M7) and POH synergistically inhibit in vitro growth of pancreatic cancers. Both wild type and mutant K-Ras pancreatic cancer cells, i.e., BxPC-3 (A) and MIA PaCa-2 (B), respectively, were infected with Ad.5-mda-7, Ad.5/3-mda-7, Ad.5-CTV-M7 or Ad.5/3-CTV-M7 followed by treatment with or without POH and MTT assays were performed after 3 days. Points; mean±S.E of three different experiments each performed in quadruplicate.

Figure 8:
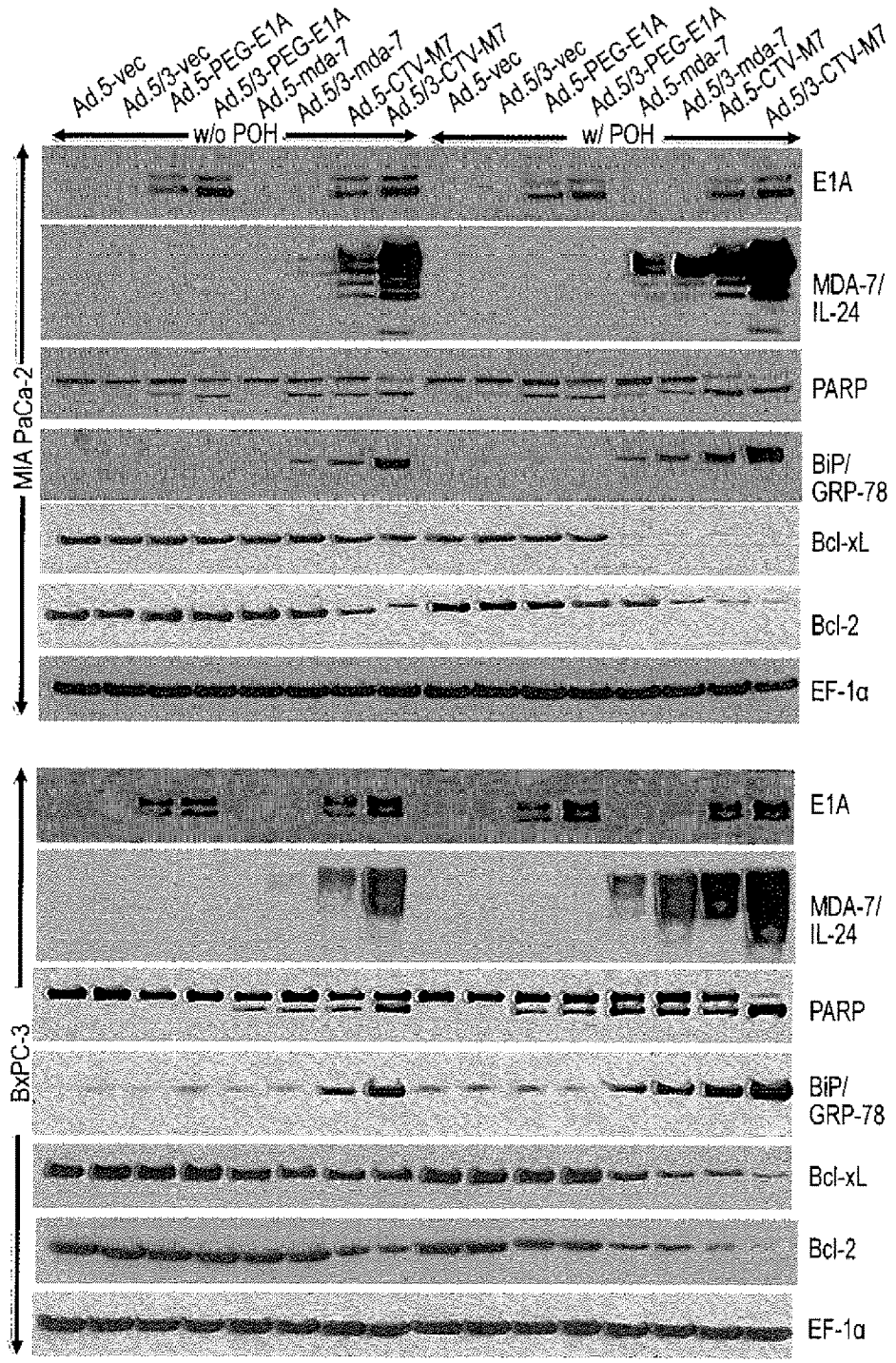

FIG. 8. Enhanced mda-7/IL-24-induced apoptosis in pancreatic cell lines by Ad.5/3-PEG-E1A-mda-7 (Ad.5/3-CTV-M7) in combination with POH. MIA PaCa-2 and BxPC-3 cells were treated as indicated for 48 h. Cells were collected, lysed, and proteins were separated by SDS-PAGE and analyzed by Western blotting. EF-la was used as loading control.

FIG. 9A-F. ROS generated by POH induces increased expression of MDA-7/IL-24 in pancreatic cancer cell lines culminating in enhanced apoptosis. (A) MIA PaCa-2 and (B) BxPC-3 cell lines were infected with the indicated Ads and/or POH, and secreted MDA-7/IL-24 was quantified using human MDA-7/IL-24 ELISA kit, and mda-7/IL-24 mRNA from (C) MIA PaCa-2 and (D) BxPC-3 was quantified using qRT-PCR 48 h post infection. Apoptosis in (E) MIA PaCa-2 and (F) BxPC-3 cells was measured by flow-cytometer after staining the cells with AnnexinV/PI. * (p<0.05),  (p<0.01), and * (p<0.001) indicates the increasing level of significance after performing un-paired t-test between Ads treated group vs. Ads treated group plus POH as indicated in A, B, E and F. * (p<0.05),  (p<0.01), and * (p<0.001) indicates the increasing level of significance after performing an un-paired t-test of different Ads treated group with respect to Ad.5-mda-7 treated group as shown in C and D.

FIG. 10A-G. Ad.5/3-CTV-M7 sensitizes therapy-resistant pancreatic cells to cell killing by inducing ER-stress. MIA PaCa-2 clones stably expressing (A) Bcl-2 and (B) Bcl-xL were developed and quantification was done by qPCR. * (p<0.05),  (p<0.01), and * (p<0.001) indicates the increasing level of significance after performing un-paired t-test between control vs. different stable clones. MIA PaCa-2 clones stably expressing (C) Bcl-2 and (D) Bcl-xL stable were treated with Ad.5/3-mda-7, Ad.5/3-mda-7+POH, Ad.5/3-CTV-M7, Ad.5/3-CTV-M7+POH or untreated Ad.5/3-vec (control). *, p<0.05 versus Ads treated cl-1 (control clone for Bcl-2 overexpression) (C) or cl-6 (control clone for Bcl-xL overexpression) (D) cells. (E) Overexpression of Bcl-xL inhibits Thapsigargin (Thap)-induced ER stress-mediated apoptosis as compared to control pcDNA 3.1 MIA PaCa-2 cell cl (con). (F) MIA PaCa-2/Bcl-xL cl-3 (stable clone expressing the maximum level of Bcl-xL) cells were treated with BiP/GRP-78 shRNA (sh-BiP) followed by treatment with Ad and/or POH. Apoptosis was measured 48 h post-infection by flow-cytometer after staining the cells with AnnexinV/PI and (G) Western blotting of MIA PaCa-2/Bcl-xL (cl-3) cells untreated or treated with POH and infected with the indicated Ads was performed after probing with the indicated antibodies.

FIG. 11A-E. Ad.5/3-CTV-M7 in combination with POH completely eradicates primary and distant tumors in nude mice bearing human pancreatic tumor xenografts. Tumor xenografts generated from MIA-PaCa-2 cells stably expressing a luciferase gene (MIA PaCa-2-luc) were established in both the left and right flanks of nude mice. Tumors on the left flank were sonoporated for 10 min following tail-vein injection of the indicated complement treated Ad/MB complex, and treated as described in Materials and Methods section for 3 weeks starting from day 14 (1 injection/week). POH was administered i.p. daily for 4 weeks from day 1 of implantation of cells in nude mice. (A) Bioluminescence imaging (BLI) was performed using Xenogen In Vivo Imaging System (IVIS). BLI was performed every week and luminescence was quantified and tumor growth response curve of the left flank (B) and right flank or distant tumor (C) was plotted. (D) Secreted MDA-7/IL-24 in blood serum was measured using an MDA-7/IL-24 ELISA kit. (E) There was significant increase in 'bystander' effect of MDA-7/IL-24 in inhibiting in vivo tumor growth as measured by BLI. Statistical analyses were performed using un-paired t-test between different groups. *, , and * indicates the level of significance with $p<0.05$, $p<0.01$ and $p<0.001$ respectively.

FIG. 12A-E. In vivo antitumor effect of Ad.5/3-CTV-M7 plus POH in nude mice bearing therapy resistant MIA PaCa-2/Bcl-xL xenografts. Tumor xenografts with MIA-PaCa-2 cells stably expressing a Bcl-xL gene (MIA PaCa-2/Bcl-xL) were established in both the left and right flanks. Tumors on the left flank were sonoporated for 10 min following tail-vein injection of indicated complement treated Ad/microbubble complex, and treated as described in Materials and Methods section for 3 wks starting from day 14 (1 injection/week). POH was administered i.p. injection daily for 4 weeks from day 1 of implantation of cells in nude mice. Tumor volume of the left flank (A) and right flank (B) was measured using digital calipers, and the graph was plotted over time. Tumor mass and weight were measured for both left (C) and right flank (D) tumors after the mice were sacrificed at the end of experiment. (E) Apoptosis was measured by TUNEL staining of fixed cells. Statistical analyses were performed using un-paired t-test between different groups. * ($p>0.05$),  ($p>0.01$), and * ($p>0.001$) versus Ad.5/3-treated group.

FIGS. 13A-D. Cancer-specific oncolytic effects of CTV-M7 in pancreatic cancer cells. Pancreatic cancer cells were treated with non-replicating Ad.5-mda-7 or Ad.5/3-mda-7 as well as conditional replication-competent Ads (CRCA) i.e., Ad.5-CTV-M7 and Ad.5/3-CTV-M7 and MTT assays were performed after 3 days. $IC_{50}$ was calculated using GraphPad Prism 5.0. Points; mean±S.E. of three different experiments each performed in quadruplicate.

Figure 14:
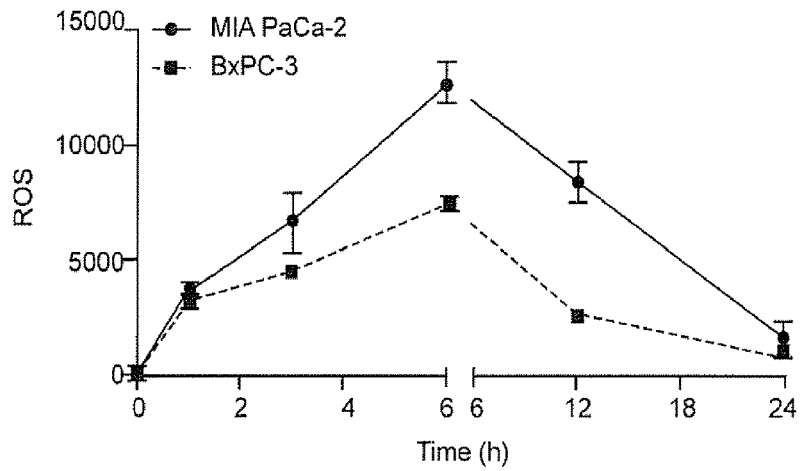
Figure 15A:
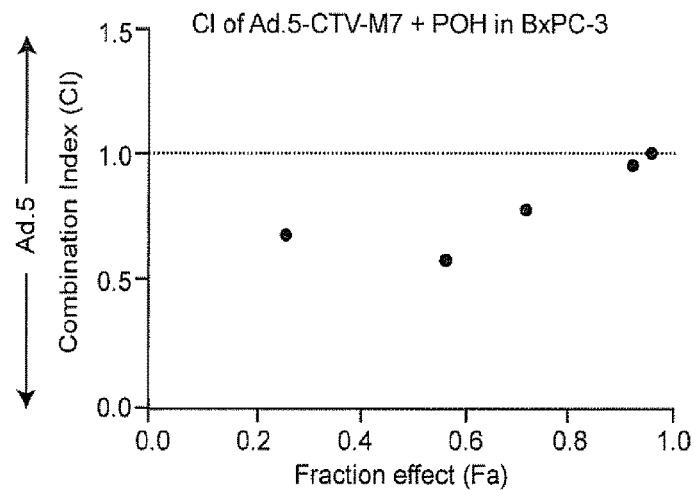
Figure 15B:
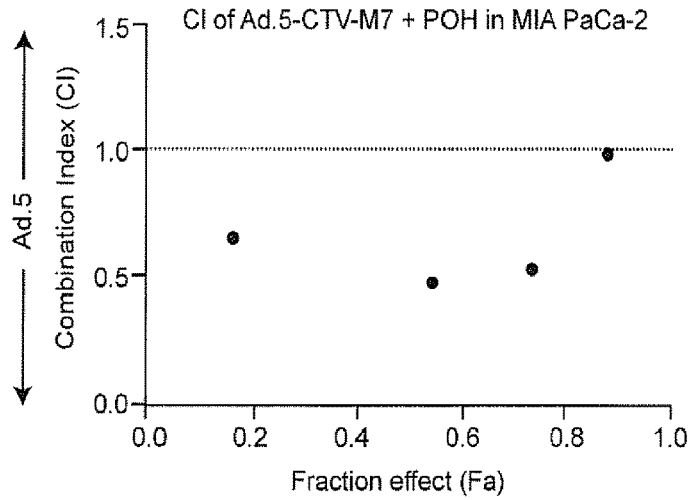
Figure 15C:
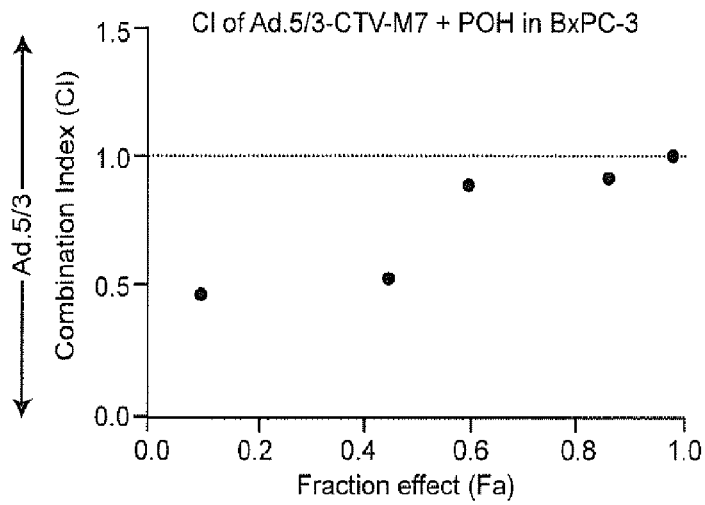
Figure 15D:
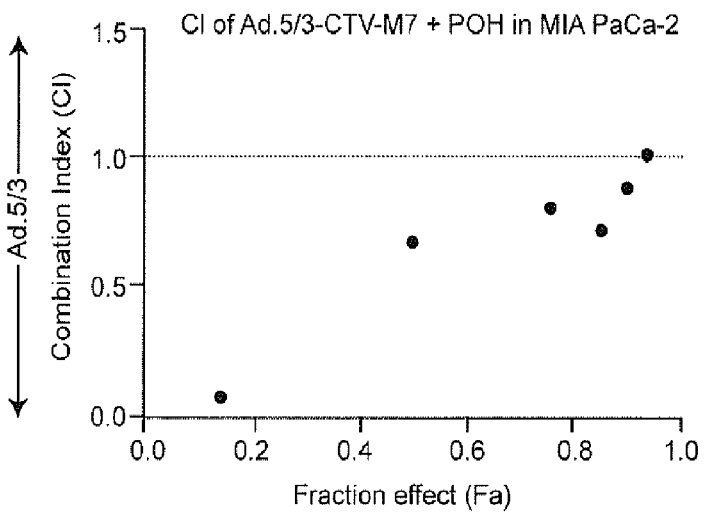

FIG. 14. Temporal kinetics of reactive oxygen species (ROS) formation induced by POH. MIA PaCa-2 and BxPC-3 cells were stained with carboxy-H2DCF-DA in PBS for 30 min followed by treatment of POH, and fluorescence was measured using a Flurometer with a green filter at the indicated time points. The readings noted were the difference between POH-treated group compared to untreated control.

FIGS. 15A-D. Combination index or Interaction index of pancreatic cancer cells treated with CTV-M7 plus POH. BxPC-3 and MIA PaCa-2 cells were treated with increasing doses (vp/cell) of Ad.5-CTV-M7 or Ad.5/3-CTV-M7 (10-1000) in combination with increasing doses of POH (10-1000 μM) and MTT results were plotted to calculate the combination index (CI).

Figure 16:
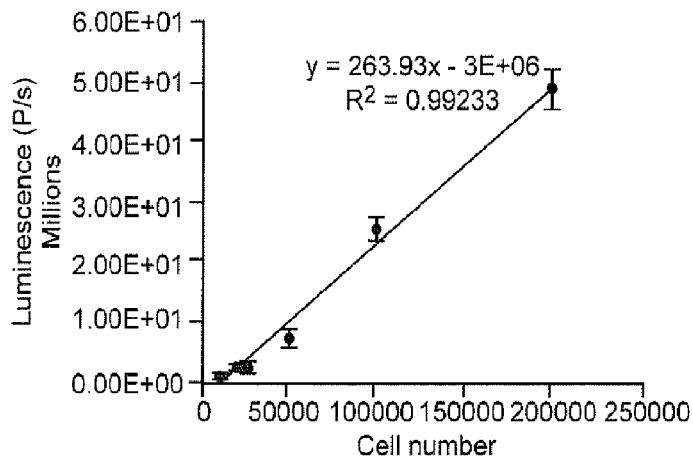

FIG. 16. Bioluminescence imaging (BLI) indicates a positive correlation between bioluminescence and cell number. MIA PaCa-2-luc cells were seeded in 24-well plate, and luminescence was measured after 12 h after adding D-luciferin. Image acquisition was performed using a Xenogen In Vivo Imaging System (IVIS) and the images were quantified using Living Image 4.3.1 software.

Figure 17:
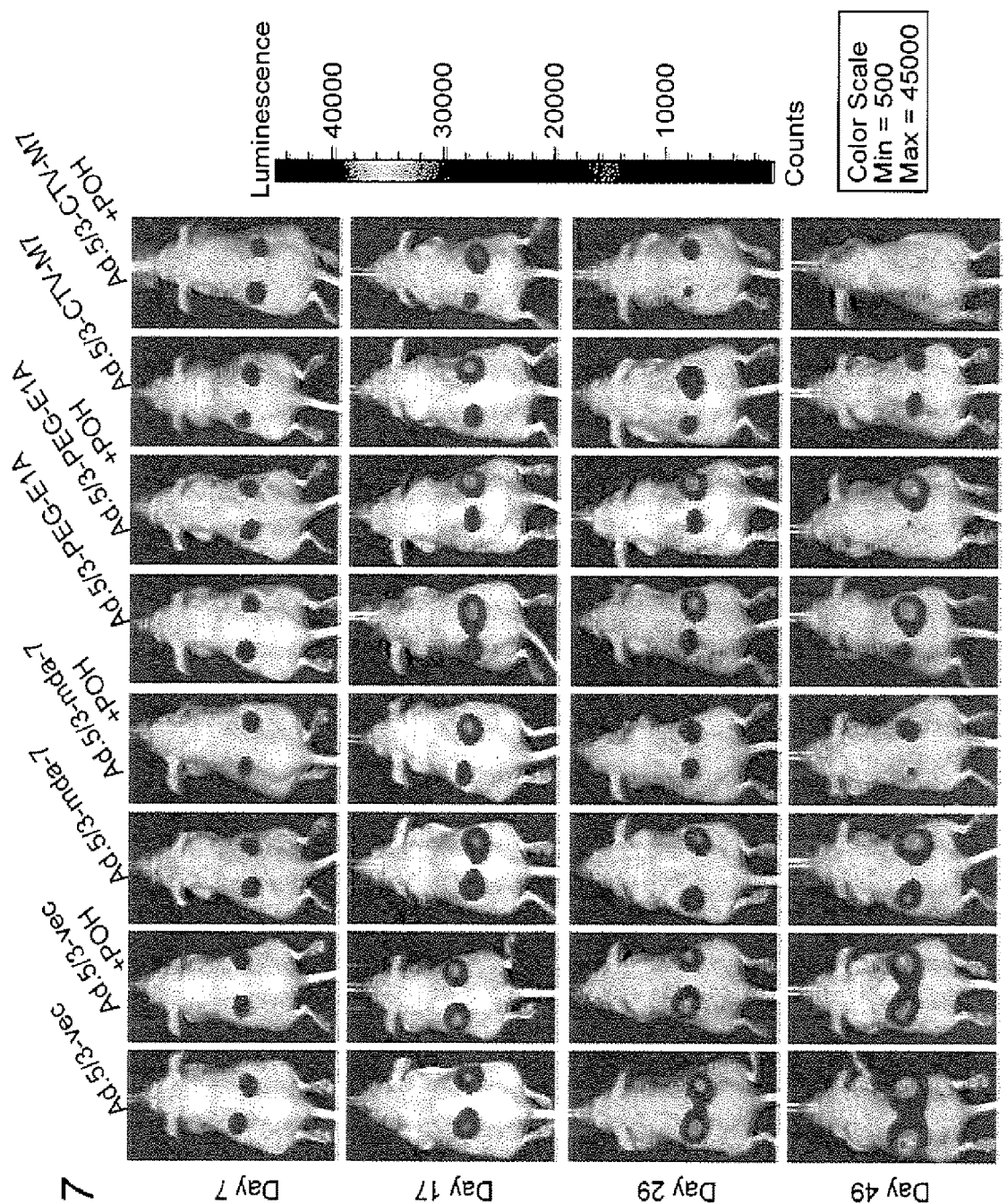

FIG. 17. Ad.5/3-CTV-M7 eradicates primary and secondary tumors in vivo in a human pancreatic cancer xenograft model. Tumor xenografts of MIA PaCa-2 cells stably expressing a luciferase gene (MIA PaCa-2-luc) were established in both the left and right flanks of athymic nude mice. Tumors on the left flank were sonoporated for 10 min following tail-vein injection of the indicated complement treated Ad/MB complexes, and treated as described in Materials and Methods section for 3 weeks starting from day 14 (1 injection/week). POH was administered i.p. daily for 4 weeks from day 1 of impanation of cells in nude mice. Bioluminescence imaging (BLI) was performed using a Xenogen In Vivo Imaging System (IVIS) after i.p. administration of D-luciferin. BLI was performed at the indicated days.

Figures for Example 3

Figure 18A:
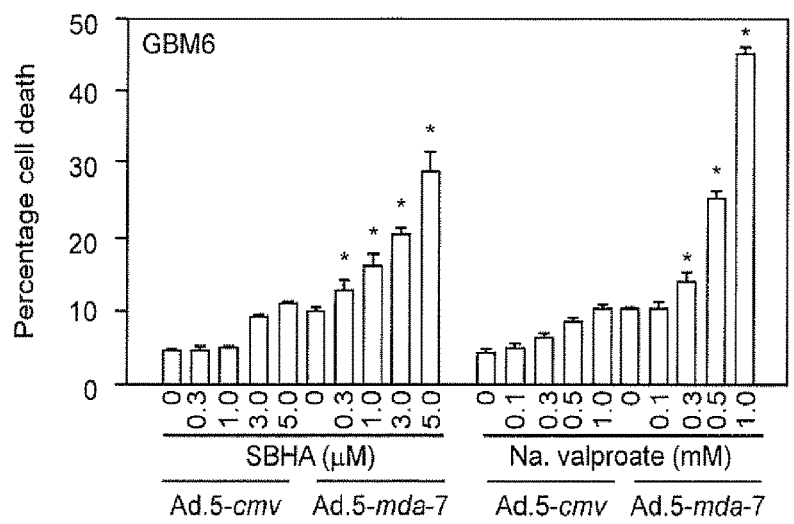
Figure 18B:
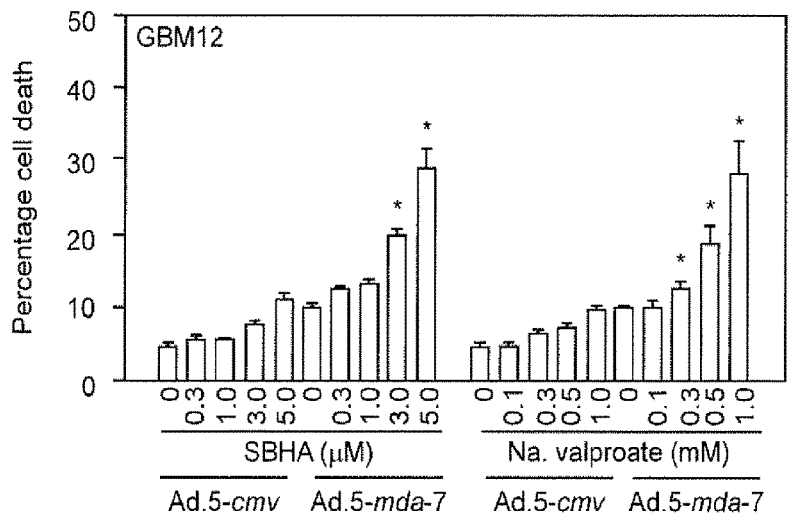
Figure 18C:
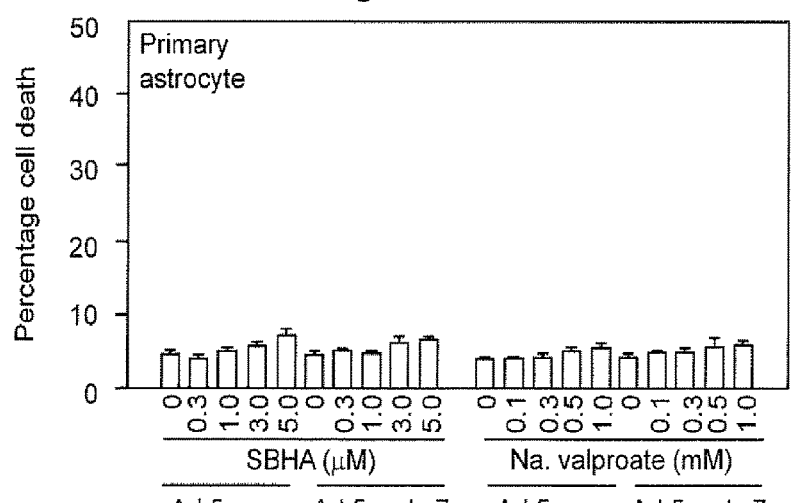

FIG. 18A-C. SBHA and Na Valproate enhance Ad.5-mda-7 toxicity in multiple primary human GBM isolates but not in primary human astrocytes. (A) GBM6 cells, (B) GBM12 cells and (C) primary human astrocytes were infected with empty vector or recombinant serotype 5 adenovirus to express MDA-7/IL-24; at a multiplicity of infection (moi) of 10. After infection (24 h) cells were treated with vehicle control or with pharmacologically achievable concentrations of HDACIs, Na Valproate (0, 0.3, 0.5, 1.0 mM) or the vorinostat analogue SBHA (0, 0.3, 1.0, 3.0, 5.0 □M). Cells were isolated 48 h later and viability determined by trypan blue exclusion (n=3, +/−SEM) (*$p<0.05$ greater than corresponding value in Ad.5-cmv infected cells).

FIG. 19A-D. Induction of ER stress and autophagy plays a role in the interaction between MDA-7/IL-24 and HDACIs. Panel A. GBM6 cells were transfected in quadruplicate with a plasmid to express an LC3 (ATG8)-GFP fusion protein and in parallel transfected with scrambled siRNA (siSCR) or an siRNA to knock down Beclin/expression. Twenty-four h after transfection cells were treated with GST or GST-MDA-7 (20 nM) and/or SBHA (3 μM). Cells (a representative of 40 per well per time point) were examined 6 h, 12 h and 24 h after treatment using an Axiovert microscope (x40) for the formation of punctate vesicles containing LC3-GFP. Data are plotted as the number of LC3-GFP vesicles per cell (n=-2, +/− SEM) (*$p<0.05$ greater than GST+VEH; **$p<0.05$ greater than GST-MDA-7+VEH). Panel B. GBM6 cells were transfected with scrambled siRNA (siSCR) or an siRNA to knock down Beclinl expression. Twenty-four h after transfection cells were treated with GST or GST-MDA-7 (20 nM) and/or SBHA (3 μM). Cells were isolated 48 h later and viability determined by trypan blue exclusion (n=3, +/− SEM) (#$p<0.05$ less than corresponding value in siSCR cells). Panel C. GBM6 cells were transfected with an empty vector control plasmid or a plasmid to express dominant negative PERK. Twenty-four h after transfection cells were treated with GST-MDA-7 (20 nM), SBHA (3 M) or the agents combined. Cells were isolated 6 h after exposure and the phosphorylation of PERK and eIF2α determined (representative n=2). Panel D. GBM6 cells were transfected in quadruplicate with an LC3 (ATG8)-GFP fusion protein and in parallel transfected with an empty vector control plasmid or a plasmid to express dominant negative PERK. Twenty-four h after transfection cells were treated with GST or GST-MDA-7 (20 nM) and/or SBHA (3 μM). Cells (a representative of 40 per well per time point) were examined 24 h after treatment using an Axiovert microscope (λ40) for the formation of punctate vesicles containing LC3-GFP. Data are plotted as the number of LC3-GFP vesicles per cell (n=3, +/− SEM) (#p<0.05 less than corresponding value in CMV cells).

Figure 20:
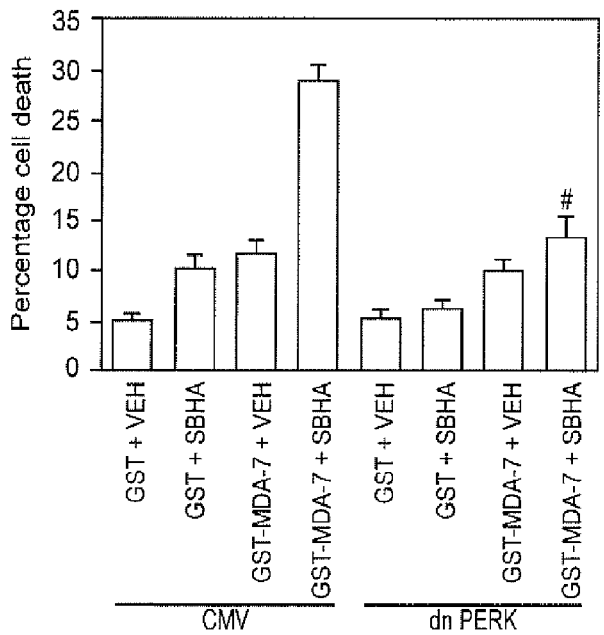

FIG. 20. GBM6 cells were transfected with an empty vector control plasmid or a plasmid to express dominant negative PERK. Twenty-four h after transfection cells were treated with GST-MDA-7 (20 nM), SBHA (3 µM) or the agents combined. Cells were isolated 48 h later and viability determined by trypan blue exclusion (n=3, +/− SEM) (#p<0.05 less than corresponding value in CMV cells).

Figure 21A:
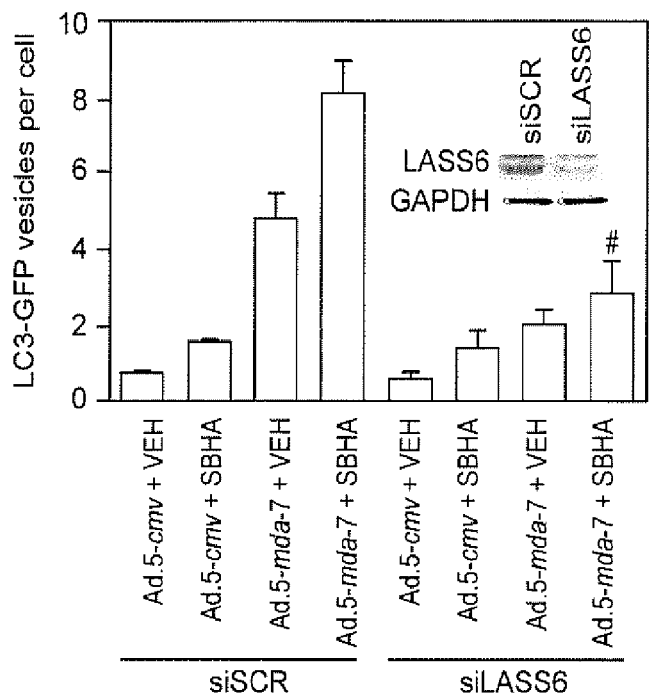
Figure 21B:
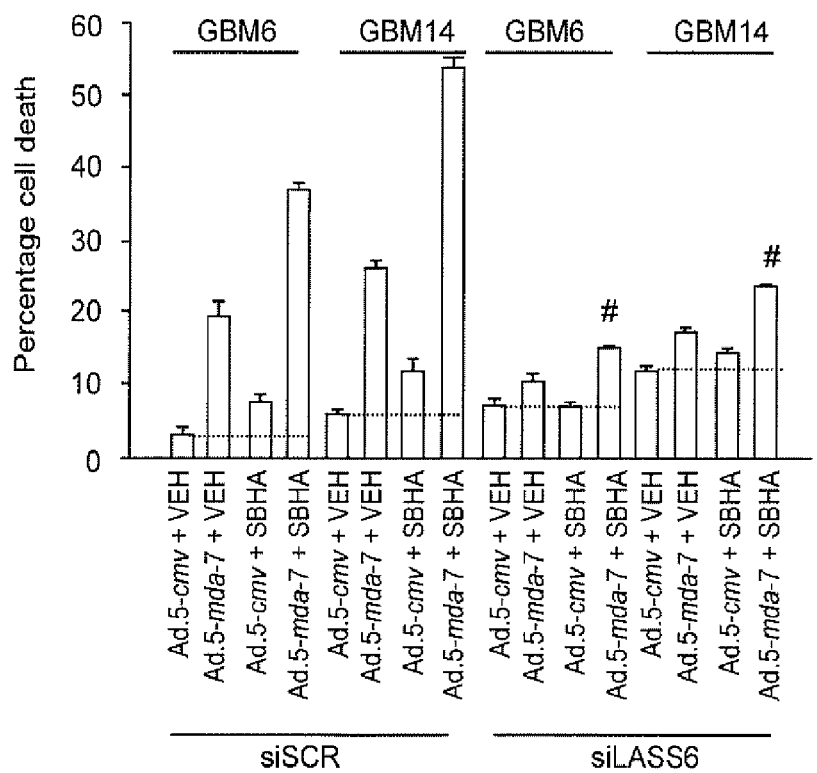

FIGS. 21A-B. De novo ceramide generation plays an essential role in the interaction between MDA-7/IL-24 and HDACIs. Panel A. GBM6 cells were transfected in quadruplicate with a plasmid to express an LC3 (ATG8)-GFP fusion protein and in parallel transfected with scrambled siRNA(siSCR) or an siRNA to knock down ceramide synthase 6 (LASS6) expression. Cells were infected with empty vector or recombinant serotype 5 adenovirus to express MDA-7/IL-24; at a multiplicity of infection (moi) of 10. After infection (24 h) cells were treated with vehicle control or with the vorinostat analogue SBHA (3.0 µM). Cells (a representative of 40 per well per time point) were examined 24 h after treatment using an Axiovert microscope (x40) for the formation of punctate vesicles containing LC3-GFP. Data are plotted as the number of LC3-GFP) vesicles per cell (n=3, +/− SEM) (#p<0.05 less than corresponding value in siSCR cells). Panel B. GBM6 and GBM14 cells were transfected with scrambled siRNA (siSCR) or an siRNA to knock down ceramide synthase 6 (LASS6) expression. Twenty-four h later cells were infected with empty vector or recombinant serotype 5 adenovirus to express MDA-7/IL-24; at a multiplicity of infection (moi) of 10. After infection (24 h) cells were treated with vehicle control or with the vorinostat analogue SBHA (3.0 µM). Cells were isolated 48 h later and viability determined by trypan blue exclusion (n=3, +/− SEM) (#p<0.05 less than corresponding value in siSCR cells).

Figure 22A:
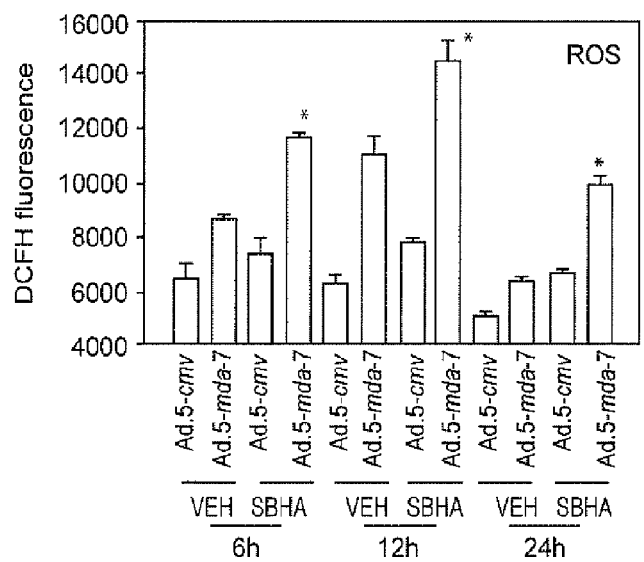
Figure 22B:
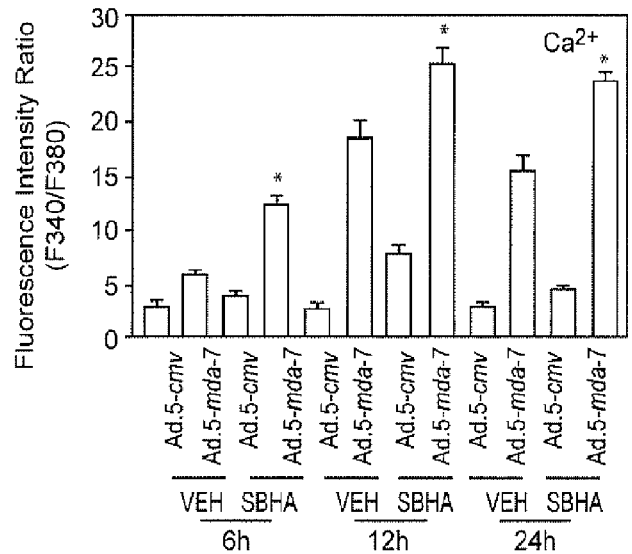
Figure 22C:
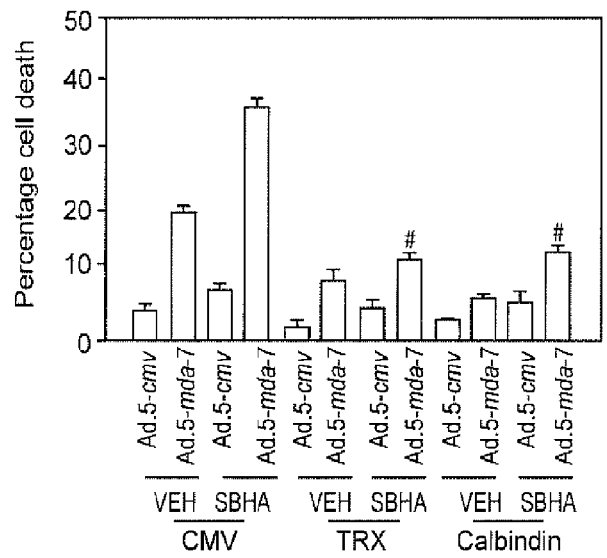

FIG. 22A-C. SBHA intensifies and prolongs ROS and $Ca^{2+}$ generation caused by MDA-7/IL-24. Panel A. GBM6 cells were infected with empty vector or recombinant serotype 5 adenovirus to express MDA-7/IL-24; at a multiplicity of infection (moi) of 10. Twenty-four h after infection cells were treated with vehicle (DMSO) or SBHA (3 µM). Cells were loaded with DCFH and the levels of ROS under each condition determined 6 h, 12 h and 24 h after SBHA treatment (n=3, +/−SEM) (*p<0.05 greater than Ad.5-mda-7+VEH). Panel B. GBM6 cells were infected with empty vector or recombinant serotype 5 adenovirus to express MDA-7/IL-24; at a multiplicity of infection (moi) of 10. Twenty-four h after infection cells were treated with vehicle (DMSO) or SBHA (3 µM). Cells were loaded with Fura-2 and the levels of free $Ca^{2+}$ under each condition determined 6 h, 12 h and 24 h after SBHA treatment (n=3, +/−SEM) (*p<0.05 greater than Ad.5-mda-7+VEH). Panel C. GBM6 cells were transfected with an empty vector plasmid, a plasmid to express thioredoxin (TRX) or a plasmid to express calbindin and in parallel infected with empty vector or recombinant serotype 5 adenovirus to express MDA-7/IL-24; at a multiplicity of infection (moi) of 10. Twenty-four h after infection cells were treated with vehicle (DMSO) or SBHA (3 µM). Cells were isolated 48 h later and viability determined by trypan blue exclusion (n=3, +/−SEM). (#p<0.05 less than corresponding value in CMV transfected cells).

Figure 23A:
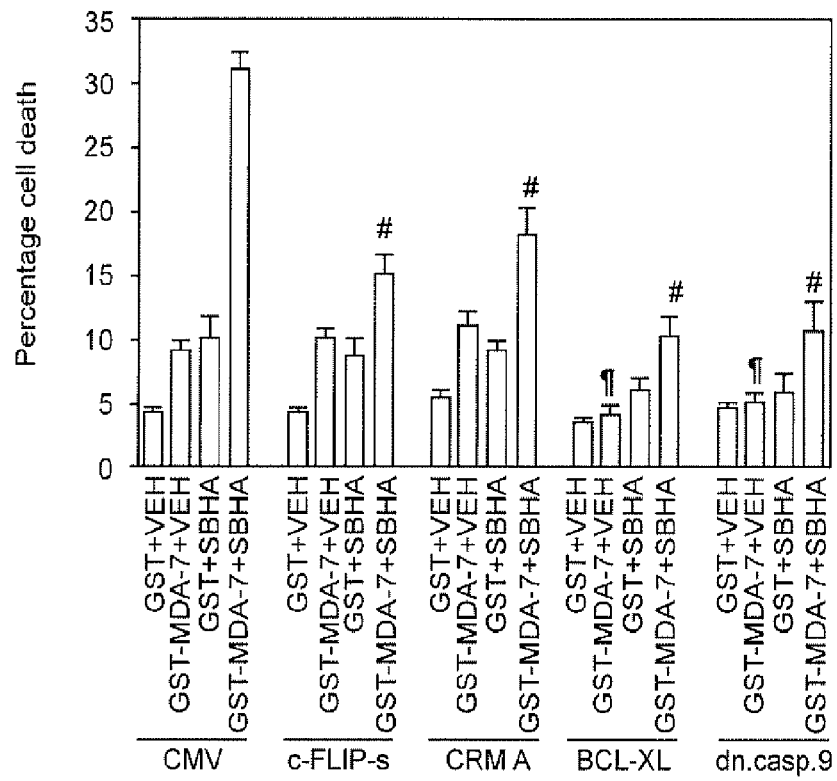

FIGS. 23A and B. SBHA enhances MDA-7/IL-24 toxicity through the extrinsic pathway. Panel A. GBM6 cells were infected with empty vector or recombinant serotype 5 adenovirus to express c-FLIP-s; CRM A; BCL-XL; or dominant negative caspase 9. Twenty-four h after infection cells were treated with GST or GST-MDA-7 (20 nM) and/or SBHA (3 µM). Cells were isolated 48 h later and viability determined by trypan blue exclusion (n=3, +/−SEM). (#p<0.05 less than corresponding value in CMV infected cells; ¶p<0.05 less than corresponding values in CMV, c-FLIP-s and CRM A infected cells). Panel B. GBM6 cells were infected with empty vector or recombinant serotype 5 adenovirus to express MDA-7/IL-24; at a multiplicity of infection (moi) of 10. Twenty-four h after infection cells were treated with increasing concentrations of obatoclax (GX15-070, 0-200 nM) or HA14-1 (0-10 µM). Cells were isolated 24 h later and viability determined by trypan blue exclusion (n=3, +/−SEM) (*p<0.05 greater than corresponding Ad.5-cmv values).

Figure 24:
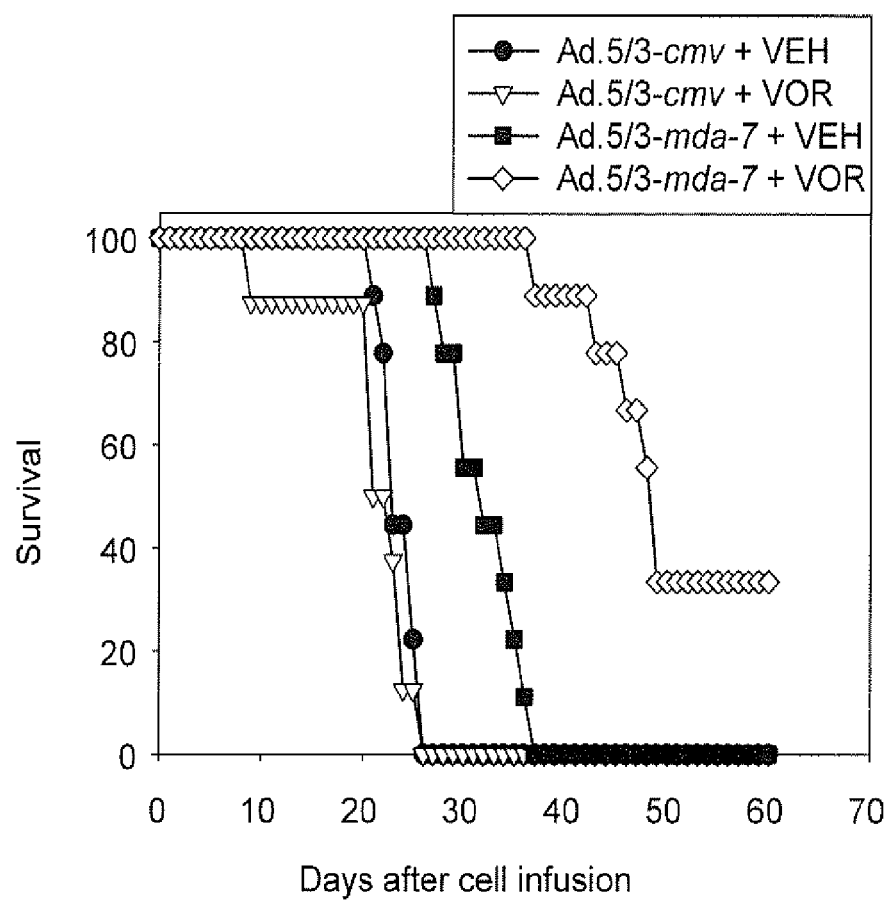

FIG. 24. SAHA enhances MDA-7/IL-24 toxicity in vivo. GBM6 cells ($0.5 \times 10^6$) were implanted into the brains of athymic mice. Seven days later tumors were infused with $1 \times 10^8$ pfu of either Ad.5/3-cmv or Ad.5/3-mda-7. Twenty-four h after virus infusion animals were treated with vehicle diluent (cremophore, PO) or vorinostat (SAHA, 25 mg/kg QD, PO) for 5 days. Animal survival was monitored on a daily basis (n=2, 8 animals total).

FIG. 25A-E. Ad.5/3-PEG-E1A-mda-7 (Ad.5/3-CTV; Ad.5/3-CTV-M7) prolongs animal survival in a dose-dependent fashion and does so to a greater extent than Ad.5/3-mda-7. Panel A. GBM6-luciferase cells ($0.5 \times 10^6$) were implanted into the brains of athymic mice. Seven days later tumors were infused with $1 \times 10^8$ pfu of either: Ad.5/3-cmv: Ad.5/3-mda-7; Ad.5/3-PEG-E1A; or Ad.5/3-PEG-E1A-mda-7 (Ad.5/3-CTV; Ad.5/3-CTV-M7). On the days indicated in the graph animals were injected with luciferin (150 mg/kg) and were imaged 15 min later following placement into an IVIS Xenogen imager. The fold-increase in luciferase intensity for the mean of each animal group was plotted (n=2, 6 animals total +/− SEM) (#p<0.05 less than Ad.5/3-cmv; Ad.5/3-mda-7; or Ad.5/3-PEG-E1A (Ad.5/3-CTV, Ad.5/3-CTV-M7). The-Fold change in luciferase activity at day 12 is shown numerically. Panel B. Brains from animals at day 12 (Panel A) were removed, were fixed in OCT compound (Tissue Tek); cryostat sectioned (Leica) as 12 m sections. Sections from tumor tissue and normal brain were stained for apoptosis (TUNEL) and for expression of the viral E1A protein. Panel C. GBM6 cells ($0.5 \times 10^6$) were implanted into the brains of athymic mice. Seven days later tumors were infused with: Ad.5/3-cmv ($1 \times 10^9$ pfu); Ad.5/3-mda-7 ($1 \times 10^9$ pfu); Ad.5/3-PEG-E1A ($1 \times 10^8$; $3 \times 10^8$, $1 \times 10^9$ pfu): and Ad.5/3-PEG-E1A-mda-7 (Ad.5/3-CTV; Ad.5/3-CTV-M7) ($1 \times 10^8$; $3 \times 10^8$; $1 \times 10^9$ pfu). Animal survival was monitored on a daily basis (n=2, 6 animals total) ((a) p<0.04 greater survival than Ad.5/3-cmv; (b) p<0.0008 greater survival than Ad.5/3-cmv; (c) p<0.04 greater survival than Ad.5/3-mda-7; (d) p<0.004 greater survival than Ad.5/3-mda-7; (e) p<0.0008 greater survival than Ad.5/3-PEG-E1A-mda-7 (Ad.5/3-CTV; Ad.5/3-CTV-M7) at a dose of $3 \times 10^8$ pfu). Panel D. Syrian hamster brains were infused with PBS; Ad.5/3-cmv-E1A ($2 \times 10^9$ pfu); or Ad.5/3-PEG-E1A-mda-7 (Ad.5/3-CTV; Ad.5/3-CTV-M7) ($2 \times 10^9$ pfu). Seventy-two h after infusion animal brains, livers and kidneys were isolated and fixed. Sections (12 m) were taken and stained for apoptosis (TUNEL), the levels of viral E1A protein, and the levels of MDA-7/IL-24 protein. Panel E. Syrian hamster brains were infused with PBS; Ad.5/3-cmv-E1A ($2 \times 10^9$ pfu): or Ad.5/3-PEG-E1A-mda-7

(Ad.5/3-CTV; Ad.5/3-CTV-M7) (2×10$^9$ pfu). Seventy-two h and 1 week after infusion animals were sacrificed and their neck lymph nodes dissected.

FIGS. 26A-G Full Length Sequences for (1) PEG-3-E1, (2) CMVp-mda-7 and (3) Ad.5/3 fiber.

DETAILED DESCRIPTION

The invention provides a novel chimeric tropism modified adenoviral vector, Ad.5/3-CTV (also referred to as Ad.5/3-CTV-M7, a tropism modified CTV (containing mda-7) in the Ad.5/3 background) with profound anti-cancer activity in both low and high CAR expression human cancer cells.

Ad.5/3-CTV (Ad.5/3-CTV-M7) is based in part on a previously constructed conditionally replication competent adenovirus (CRACA), "Cancer Terminator Virus" (CTV). In CTV, adenoviral replication is controlled by the cancer-selective Progression Elevated Gene-3 (PEG-3) promoter and this construct simultaneously expresses the anticancer agent melanoma differentiation associated gene-7 also called interleukin-24 (mda-7/IL-24) from the E3 region of the adenovirus (Ad.5/3-CTV-M7). However, CTV was generated on a serotype 5-background (Ad.5-CTV) so that infectivity depends on the presence of Coxsackie-Adenovirus Receptors (CARs) in targeted cells. CARs are frequently reduced in many tumor types, including malignant gliomas (GBM), renal cancers, prostate cancer, colorectal cancer and many others, thereby limiting effective therapy.

To develop methods for improving infectivity of human cancers, engineered variant adenoviruses (Ads) from different species were constructed and evaluated. These studies produced the unanticipated finding that serotype chimerism created by replacing the Ad.5 fiber knob with the Ad.3 fiber knob resulted in viruses with superior infectivity of diverse human cancer cell types. Based on this observation, a novel adenoviral construct has now been created using the Ad.5/3 chimerism in combination with CTV (Ad.5/3-CTV; Ad.5/3-CTV-M7). This chimera advantageously infects cancer cells in a CAR-independent manner. As demonstrated herein, Ad.5/3-CTV (Ad.5/3-CTV-M7) displays enhanced anti-tumor activity in vitro and in vivo in xenograft tumors in nude mice, even in low CAR prostate, GBM, renal and colorectal cancers. Additionally, Ad.5/3-CTV (Ad.5/3-CTV-M7) shows significant anti-tumor activity in immune competent Hi-Myc transgenic mice, which develop prostate cancer, e.g., when delivered by ultrasound-targeted microbubble destruction (UTMD) approach.

The invention thus provides the genetically engineered adenoviral vector Ad.5/3-CTV (Ad.5/3-CTV-M7) as well as compositions containing the vector and methods of using the same to kill cancer cells and treat cancer, especially cancers which express little or no CARs. Ad.5/3-CTV (Ad.5/3-CTV-M7) thus has utility in addressing a wide array of different types of cancers, and it may be used alone or in combination with other therapeutic agents.

Specific examples of cancers that may be treated with Ad.5/3-CTV (Ad.5/3-CTV-M7) alone or in combination with other therapeutic agents include but are not limited to solid tumors, blood born tumors such as leukemia, acute or chronic lymphoblastic leukemia, breast cancer, chordoma, craniopharyngioma, endometrial cancer, ependymoma, Ewing's tumor, gastric cancer, germinoma, glioma, glioblastoma, hemangioblastoma, hemangiopercytioma, Hodgkins lymphoma, medulloblastoma, leukaemia, mesothelioma, neuroblastoma, non-Hodgkins lymphoma, pinealoma, retinoblastoma, sarcoma (including angiosarcoma, osteosarcoma and chondrosarcoma), bladder carcinoma, brain tumor, breast carcinoma, bronchogenic carcinoma, carcinoma of the kidney, cervical carcinoma, choriocarcinoma, cystadenocarcinome, embryonal carcinoma, epithelial carcinoma, esophageal carcinoma, cervical carcinoma, colon carcinoma, colorectal carcinoma, endometrial carcinoma, gallbladder carcinoma, gastric carcinoma, head and neck carcinoma, liver carcinoma, lung carcinoma, medullary carcinoma, non-small cell bronchogenic/lung carcinoma, lung cancer, ovarian carcinoma, pancreas carcinoma, papillary carcinoma, papillary adenocarcinoma, prostate carcinoma, small intestine carcinoma, rectal carcinoma, renal cell carcinoma, skin carcinoma, squamous cell carcinoma, sebaceous gland carcinoma, testicular carcinoma, osteosarcoma, ovary cancer, uterine carcinoma, CAR prostate cancer, glioma (GBM), renal cancer, and colorectal cancer.

Specific examples of therapeutic agents, which may be used in combination with Ad.5/3-CTV (Ad.5/3-CTV-M7) include but are not limited to agents that augment reactive oxygen (ROS) production (ROS inducers, natural products and other agents) (e.g., limonene, perillyl alcohol, arsenic trioxide, resveratrol, cyaniding-3-rutinoside, diallyl disulfide (DADS), and methyl jasmonate), HDAC inhibitors (e.g., SAHA, Vorinostat, Rocllinostat (ACY-1215) Panobinostat (LBH589), Entinostat (MS-275), Romidepsin (FK228, Depsipeptide), Trichostatin A (TSA), Mocetinostat 9MGCD0103) RGFP966, Bellinostat (PXD101), Scriptald, PCL-24781 (Abexinostat), LAQ824 (Dacinostat), JNJ26481585, valproic acid sodium salt (sodium valproate), CUDC-101, Drosinostate, MC1568, Pracinostate (SB939), Givinostat (ITF2357) AR-42, Tubostatin A HCl, PCI-34051, CUDC-907, M344, CI994 (Tacedinaline), Tubostatin A, sodium phenylbutyrate, and Resminostat), MCL-1 inhibitors (e.g., sabutoclax, BI-97D6, Gambogic acid, 4-((E)-((Z)-2-(cyclohexylimino)-4-methylthiazol-3(2H)-ylimino)methyl) benzene-1,2,3-triol), and Bcl-2/BCL-xL inhibitors (e.g., ABT-737 (BCL-xL inhibitor), oblimersen sodium, AT-101, ABT-263, GX15-070, HA14-1, and Obatoclax).

Figure 1:
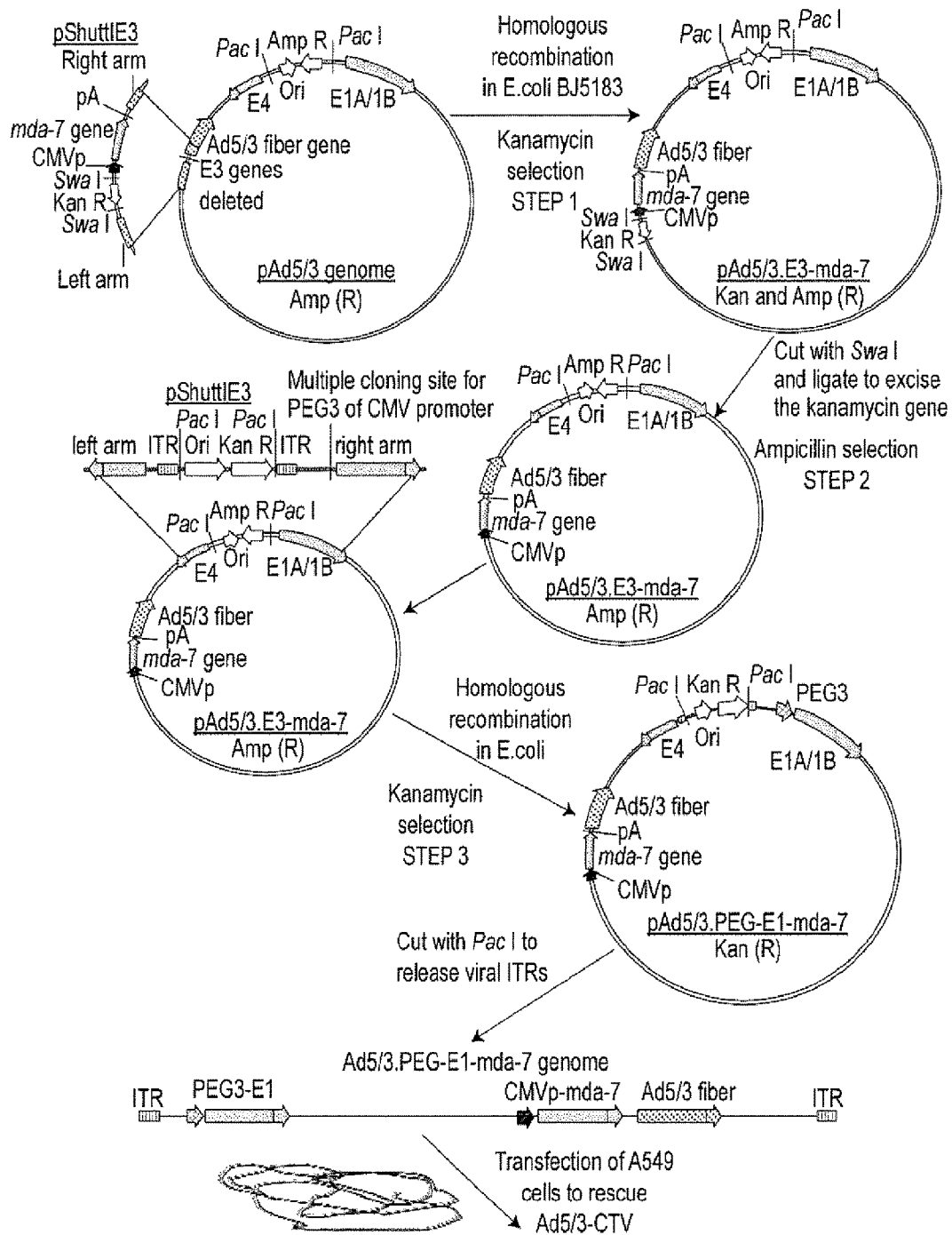
FIG. 1. Generation of a tropism-modified cancer terminator virus (Ad.5/3-CTV; Ad.5/3-CTV-M7). Schematic representation outlining the construction of a tropism modified cancer terminator virus for delivery of mda-7/IL-24. The detailed procedures are described in Material and Methods of Example 1.

As discussed in the Examples, and particularly with reference to Example 1 and FIG. 1, Ad.5/3-CTV (Ad.5/3-CTV-M7) may be constructed by 1) Homologous recombination of pAd.5/3 genomic plasmid with pShuttlE3 plasmid containing the mda-7/IL-24 expression cassette and kanamycin selection results in the pAd.5/3-E3-mda-7 genome. 2) pAd.5/3-E3-mda-7 was cut with Swa I to excise the kanamycin resistance gene. 3) The resultant pAd.5/3-E3-mda-7 plasmid was recombined with pShuttlE1 plasmid containing E1A and E1B genes under control of the PEG-3 promoter resulting in Ad.5/3-PEG-E1-mda-7 (Ad.5/3-CTV; Ad.5/3-CTV-M7) genomic plasmid. This plasmid was digested with Pac I to release viral ITRs and transfected in A549 cells to rescue the CRCA, Ad.5/3-CTV.

The nucleic acid sequences of (1) PEG-3-E1, (2) CMVp-mda-7 and (3) the Ad.5/3 fiber of Ad.5/3-CTV are presented in FIG. 26 and are set forth as SEQ ID NO: 1 (PEG-3-E1), SEQ ID NO: 2 (CMVp-mda-7) and SEQ ID NO: 3 (Ad.5/3 fiber).

The invention also provides methods of treating cancer by delivering to a patient in need thereof, a therapeutically effective amount of the Ad.5/3-CTV (Ad.5/3-CTV-M7) vector, alone or in combination with one or more therapeutic agent(s), to the patient. The subject to whom the adenoviral vector is administered is usually a mammal, and is generally a human, although this need not always be the case as veterinary applications of this technology are also contemplated. If the Ad.5/3-CTV (Ad.5/3-CTV-M7) is combined with one or more additional therapeutic agents for provisioning to a subject in need thereof, these additional therapeutic agents can be provided simultaneously with the Ad.5/3-CTV (Ad.5/3-CTV-M7) or before or after the provisioning of the Ad.5/3-CTV (Ad.5/3-CTV-M7). Further, the one or more additional therapeutic agents may be provided by the same route of administration as the Ad.5/3-CTV (Ad.5/3-CTV-M7) or by one or more different routes.

Any route of administration can be used to deliver the adenoviral vector to the mammal. Indeed, although more than one route can be used to administer the adenoviral vector, a particular route can provide a more immediate and more effective reaction than another route. The adenoviral vector may be administered intravenously or via intratumoral injection. A dose of adenoviral vector also can be applied or instilled into body cavities, absorbed through the skin (e.g., via a transdermal patch), inhaled, ingested, topically applied to tissue, or administered parenterally via, for instance, intravenous, peritoneal, intramuscular, or intraarterial administration. In one aspect, the adenoviral vector is administered via ultrasound microbubble technology, as described in US patent application 2012/0195935 (Fisher et al), which is herein incorporated by reference.

The adenoviral vector can be administered in or on a device that allows controlled or sustained release, such as a sponge, biocompatible meshwork, mechanical reservoir, or mechanical implant. Implants (see, e.g., U.S. Pat. No. 5,443, 505), devices (see, e.g., U.S. Pat. No. 4,863,457), such as an implantable device, e.g., a mechanical reservoir, an implant, or a device comprised of a polymeric composition, are particularly useful for administration of the adenoviral vector. The adenoviral vector also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of adenoviral vector administered to the mammal will depend on a number of factors, including the size and location of a tumor, the extent of any side-effects, the particular route of administration, and the like. The dose ideally comprises a "therapeutically effective amount" of adenoviral vector, i.e., a dose of adenoviral vector which kills cancer cells in the subject, usually to an extent that causes shrinkage or disappearance of a tumor, and which lessens or eradicates cancer symptoms. The treatment may be completely effective (i.e., the cancer is eliminated, the subject may go into remission) or partially effective (tumor development may be slowed so that the life expectancy is increased and/or the quality of life of the subject is improved). The desired response can entail the death of cancer cells, tumor shrinkage, tumor eradication, prevention or elimination of metastases, and the like.

The adenoviral vector may be provided as a single dose or in multiple doses ranging from $1\times10^8$ to $1\times10^{12}$ vp or $1\times10^{10}$ to $1\times10^{14}$ vp per application. As will be recognized, viral particles (vp) total infectious and non-infectious Ad (which can be 25-100 fold more than plaque forming units (pfu). For example, for direct injection, e.g., intravenous, intracardiac, intraperitoneal, etc. ($1\times10^8$ to $1\times10^{13}$ viral particles); when in a microbubble, the maximum viral load in the bubbles can be used which will result in a more focused deliver to the tumor and its surrounding vasculature. The does will vary depending on a number of factors including the type of tumor and the administration route. Since the invention utilizes cancer-specific conditionally replication competent viruses (Ad.5/3-CTV; Ad.5/3CTV-M7), higher pfu and viral particles may be used. In the GBM model, $1\times10^9$ pfu have been used, but this could be higher in humans with toxicity being the limiting factor (if it occurs). Higher doses may be tolerated in vivo, and with higher doses, more effective therapy is anticipated with fewer administrations. In some applications, a single dose of adenoviral vector comprises at least about $1\times10^6$ plaque forming units (pfu) or an equivalent higher amount of viral particles (which is referred to as viral particle units; vp; which are greater than infectious pfu) of the adenoviral vector. The dose typically is at least about $1\times10^8$ pfu (e.g., about $1\times10^9$-$1\times10^{12}$ particles), more typically at least about $1\times10^7$ pfu, more typically at least about $1\times10^8$ pfu (e.g., about $1\times10^9$-$1\times10^{11}$ particles), and most typically at least about $1\times10^9$ pfu (e.g., about $1\times10^{10}$-$1\times10^{12}$ particles) of the adenoviral vector. The dose, in some applications, may desirably comprises no more than about $1\times10^{12}$ pfu ($1\times10^{14}$ particles, or no more than about $1\times10^{13}$ particles, or no more than about $1\times10^{12}$ particles, or no more than about $1\times10^{11}$ particles, and or no more than about $1\times10^{10}$ particles).

The adenoviral vector desirably is administered in a composition, preferably a pharmaceutically acceptable (e.g., physiologically acceptable or compatible) composition, which comprises a carrier, preferably a pharmaceutically (e.g., physiologically acceptable) carrier and the adenoviral vector. Any suitable carrier can be used within the context of the invention, and such carriers are well known in the art. The choice of carrier will be determined, in part, by the particular site to which the composition is to be administered and the particular method used to administer the composition. The composition can optionally be sterile or sterile with the exception of the inventive adenoviral vector.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the adenoviral vector for use in the inventive method is administered in a composition formulated to protect the expression vector from damage prior to administration. For example, the composition can be formulated to reduce loss of the adenoviral vector on devices used to prepare, store, or administer the expression vector, such as glassware, syringes, or needles. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for adenoviral vector-containing compositions are further described in, for example, U.S. Pat. No. 6,225,289, U.S. Pat. No. 6,514,943, U.S. Patent Application Publication 2003/0153065 A1, and International Patent Application Publication WO 00/34444. A composition also can be formulated to enhance transduction efficiency. In addition, one of ordinary skill in the art will appreciate that the adenoviral vector can be present in a composition with other therapeutic or biologically-active agents. For example, factors that control inflammation, immune system stimulators, other anticancer agents, and the like.

As indicated above, the present invention inter alia provides the specified agent for use in a method of treating cancer and/or killing cancer cells in a subject in need thereof. For the avoidance of doubt, in this aspect the present invention may provide the specified agent for use as a medicament in the specified method. Further, the present invention may provide the specified agent as an active therapeutic ingredient in the specified method. Further, the present invention may provide the specified agent for use in a method of treatment of the human or animal body by therapy, the method comprising the specified method.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

EXAMPLES

Example 1

Enhanced Prostate Cancer Gene Transfer and Therapy Using a Novel Serotype Chimera Cancer Terminator Virus (Ad.5/3-CTV; Ad.5/3-CTV-M7)

Abstract

Few options are available for treating patients with advanced prostate cancer (PC). As PC is a slow growing disease and accessible by ultrasound, gene therapy could provide a viable option for this neoplasm. Conditionally replication-competent adenoviruses (CRCAs) represent potentially useful reagents for treating prostate cancer (PC). We previously constructed a CRCA, Cancer Terminator Virus (CTV), which showed efficacy both in vitro and in vivo for PC. The CTV was generated on a serotype 5-background (Ad.5-CTV; Ad.5-CTV-M7) with infectivity depending on Coxsackie-Adenovirus Receptors (CARs). CARs are frequently reduced in many tumor types, including PCs thereby limiting effective Ad-mediated therapy. Using serotype chimerism, a novel CTV (Ad.5/3-CTV; Ad.5/3-CTV-M7) was created by replacing the Ad.5 fiber knob with the Ad.3 fiber knob thereby facilitating infection in a CAR-independent manner. We evaluated Ad.5/3-CTV (Ad.5/3-CTV-M7) in comparison with Ad.5-CTV (Ad.5-CTV-M7) in low CAR human PC cells, demonstrating higher efficiency in inhibiting cell viability in vitro. Moreover, Ad.5/3-CTV (Ad.5/3-CTV-M7) potently suppressed in vivo tumor growth in a nude mouse xenograft model and in a spontaneously induced PC that develops in Hi-myc transgenic mice. Considering the significant responses in a Phase I clinical trial of a non-replicating Ad.5-mda-7 in advanced cancers, Ad.5/3-CTV (Ad.5/3-CTV-M7) will exert improved therapeutic benefit in a clinical setting.

Introduction

Prostate Cancer (PC) is the most frequently diagnosed cancer and is the second leading cause of cancer death among men in the US (Damber and Aus, 2008; Siegel et al., 2012). It is estimated that 238,590 new PC cases will be diagnosed in 2013 and 29,720 men will die of PC. Patients with localized disease may be treated with surgery or radiation, whereas the treatment options for patients with metastatic disease is purely palliative. Current therapies include hormonal therapy, radiotherapy and cytotoxic chemotherapeutic agents (Siegel et al., 2012; Sternberg, 2002). Although existing approaches are beneficial in men with various stages of PC, the complications frequently associated with these conventional treatment options diminish positive clinical outcomes. Consequently, more efficient and innovative treatments are mandatory, and genetic therapies represent promising approaches for the treatment of this neoplasm.

Using subtraction hybridization combined with induction of cancer cell terminal differentiation, our laboratory cloned melanoma differentiation-associated gene-7/interleukin-24 (mda-7/IL-24) (Jiang et al., 1995; Jiang et al., 1996), a novel member of the IL-10-related cytokine gene family (Dash et al., 2010a; Sarkar et al., 2002a; Sauane et al., 2003; Wolk et al., 2002). Subsequent studies documented that mda-7/IL-24 displays almost ubiquitous antitumor properties in vitro and in vivo, leading to its rapid entry into the clinic, where its safety and clinical efficacy, when administered by adenovirus (Ad.mda-7; INGN 241), was observed in a phase I clinical trial in humans with advanced carcinomas and melanomas (Cunningham et al., 2005; Fisher et al., 2003; Fisher et al., 2007; Jiang et al., 1996; Lebedeva et al., 2007c; Tong et al., 2005; Lebedeva et al., 2007a). mda-7/IL-24 preferentially induces apoptosis in cancer cells while exerting no discernible toxic effects toward normal cells (Dash et al., 2011a; Dash et al., 2010a; Sarkar et al., 2002b; Sauane et al., 2008) and it also elicits potent "antitumor bystander activity" in distant cancer cells as a consequence of autocrine and paracrine secretion of MDA-7/IL-24 (Dash et al., 2010b; Fisher, 2005; Lebedeva et al., 2007b; Sauane et al., 2008; Su et al., 2001a; Su et al., 2005a; Lebedeva et al., 2007a).

Since PC is generally a relatively slow-growing disease, it may require repeated gene therapy treatments, with single or multiple genes, over the lifespan of the patient. Conditionally replication-competent adenoviruses (CRCAs) provide a potentially valuable reagent for gene therapy (Curiel and Fisher, 2012). Using subtraction hybridization we cloned a novel rodent gene, progression elevated gene-3 (PEG-3), in the context of tumor progression in transformed rat embryo cells (Su et al., 1997). PEG-3: (i) displays elevated expression as a function of oncogenic transformation (by diverse oncogenes) (Su et al., 2000; Su et al., 1997) (ii) induces an aggressive cancer phenotype without promoting transformation when expressed in normal cells (Su et al., 1999; Su et al., 2002) and (iii) the gene promoter (PEG-Prom) has been isolated and shown to display elevated expression in both rodent and human tumors (including PC), with negligible expression in normal cells (including human prostate epithelium) (Bhang et al., 2011; Das et al., 2012; Sarkar et al., 2007b; Sarkar et al., 2006; Sarkar et al., 2008; Sarkar et al., 2005a; Sarkar et al., 2005b; Su et al., 2001b; Su et al., 2005b). Considering the cancer-specific expression aspects of the PEG-Prom, we constructed a bipartite serotype 5 CRCA (called a Cancer Terminator Virus, Ad.5-CTV; Ad.5-CTV-M7) in which the expression of E1A and E1B genes of Ad, necessary for replication, is controlled by the PEG-Prom (Sarkar et al., 2007b; Sarkar et al., 2006; Sarkar et al., 2008; Sarkar et al., 2005a). This novel Ad.5-CTV (Ad.5-CTV-M7) also expressed mda-7/IL-24 from the E3 region (Ad.PEG-E1A-mda-7). The ability of Ad.5-CTV (Ad.5-CTV-M7) to infect and express MDA-7/IL-24 in PC cells depends on the presence of Coxsackie-Adenovirus Receptors (CAR) on their surface. Ad.5-CTV (Ad.5-CTV-M7) is capable of efficiently infecting high CAR receptor cells (such as DU-145) and expressing robust levels of mda-7/IL-24, whereas infection is restricted and expression of MDA-7/IL-24 is minimal in low CAR receptor cells, such as PC-3 (Dash et al., 2011b; Dash et al., 2010b).

An approach to circumvent the low efficiency of Ad.5 infection of tumor cells involves 'tropism modification' in which virus capsid proteins that normally associate with CAR are modified, permitting both CAR-dependent and CAR-independent infectivity of tumor cells. Studies using various tumor cell types have shown that inclusion of the infective type 3 Ad sequence within the Ad type 5 virus knob (Ad.5/3 recombinant virus) promotes viral infectivity in tumor cells displaying reduced or no CAR expression (Azab et al., 2012; Dash et al., 2010b; Eulitt et al., 2011; Hamed et al., 2010; Park et al., 2011). It is worth noting that Ad.5/3 also retains high infectivity in CAR-expressing tumor cells showing equal efficacy when compared with Ad.5, thereby providing an expanded range of utility for Ad.5/3, in both low and high CAR-expressing tumor cells.

In this Example 1, we constructed and evaluated the in vitro and in vivo efficacy in low and high CAR PCs of a novel tropism-modified CTV in which the virus capsid proteins that normally associate with CAR were modified, Ad.5/3-CTV (Ad.5/3-CTV-M7), permitting CAR-independent infectivity of tumor cells. In low CAR PC-3 cells Ad.5/3-CTV (Ad.5/3-CTV-M7) is more efficient than Ad.5-CTV (Ad.5-CTV-M7) in infecting tumor cells, delivering a transgene (mda-7/IL-24), expressing MDA-7/IL-24 protein and inducing cancer-specific apoptosis. In an in vivo context, Ad.5/3-CTV (Ad.5/3-CTV-M7) is superior to the Ad.5-CTV (Ad.5-CTV-M7) in inhibiting in vivo tumor growth and exerting an antitumor 'bystander' effect in nude mouse human PC xenografts and Ad.5/3-CTV (Ad.5/3-CTV-M7) potently suppresses PC development in an immunocompetent Hi-Myc transgenic mouse model of PC.

Materials and Methods

Cell lines, culture conditions, and viability assays. DU-145 and PC-3 PC cells were obtained from the American Type Culture Collection and cultured as described (Lebedeva et al., 2003). Construction and characterization of PC-3 overexpressing Bcl-2, PC-3-Bcl-2, and control clones containing the neomycin vector, PC-3-Neo, were described previously (Lebedeva et al., 2003). Cell viability was determined by standard 3-(4,5-dimethylthiazol-2-yl)-2,5-diphenyltetrazolium bromide (MTT) assays (Lebedeva et al., 2003). Cell cultures were routinely tested for mycoplasma using a kit from Sigma (MP-0025) and only mycoplasma free cells were used for these studies.

Construction of Ad.5/3-CTV (Ad.5/3-CTV-M7). The genome of Ad.5/3-PEG-E1-mda-7 was generated in three consecutive steps (FIG. 1). 1) Homologous recombination of pAd.5/3 genomic plasmid with pShuttlE3 plasmid containing the mda-7/IL-24 expression cassette and kanamycin selection results in the pAd.5/3-E3-mda-7 genome. 2) pAd.5/3-E3-mda-7 was cut with Swa I to excise the kanamycin resistance gene. 3) The resultant pAd.5/3-E3-mda-7 plasmid was recombined with pShuttlE1 plasmid containing E1A and E1B genes under control of the PEG-3 promoter resulting in Ad.5/3-PEG-E1-mda-7 (Ad.5/3-CTV; Ad.5/3-CTV-M7) genomic plasmid. This plasmid was digested with Pac I to release viral ITRs and transfected in A549 cells to rescue the CRCA, Ad.5/3-CTV (Ad.5/3-CTV-M7).

Preparation of Whole-Cell Lysates and Western blot analyses. Preparation of whole-cell lysates and Western blot analyses were performed as previously described (Sarkar et al., 2005b). The primary antibodies used were anti-MDA-7/IL-24 (Gen Hunter Corporation), anti-EF1á (1:1,000; mouse monoclonal; Millipore), anti-Mcl-1 (1:500; mouse monoclonal; Santa Cruz), anti-BiP/GRP78 (1:500; rabbit monoclonal; Santa Cruz), anti-GRP94 (1:1000; rabbit monoclonal; Sigma), and anti-PARP (1:1000; rabbit monoclonal; Cell Signaling).

Human Prostate Cancer Xenografts in Athymic Nude Mice. PC-3-Bcl-2 cells ($2 \times 10^6$) were injected s.c. in 100 µL of 1:1 PBS and Matrigel in the left and right flanks of male athymic nude mice (NCRnu/nu, 6-8 weeks old, ~20 gm body weight) (Sarkar et al., 2005a). After establishing palpable tumors of ~100-mm$^3$, requiring ~7-10 days, intratumoral injections of different Ads were given only to the tumors on the left flank at a dose of $1 \times 10^{10}$ viral particles in 100 µl. The injections were given twice a week for four weeks. A minimum of five animals was used per experimental point. Tumor volume was calculated using the formula: δ/6×larger diameter×(smaller diameter)². At the end of the experiment, the animals were sacrificed, and the tumors were removed and weighed.

Hi-Myc mice and animal husbandry protocols. The VCU Institutional Animal Care and Use Committee approved the experimental protocol used in this study and the animals were cared for in accordance with institutional guidelines. This study used Hi-Myc transgenic mice in which prostate-specific expression of human c-Myc is driven by the rat probasin promoter with two androgen response elements (ARR2/probasin promoter) (Ellwood-Yen et al., 2003). Mice were obtained from the Mouse Repository of the National Cancer Institute Mouse Models of Human Cancer Consortium at NCI Frederick, Md., USA. Mouse-tail DNA was isolated using the DNeasy Blood & Tissue Kit from QIAGEN (Valencia, Calif.) and subjected to a PCR-based screening assay for genotyping. For genotyping Hi-MYC mice, the upstream primer (located within the ARR2-PB promoter), 5'-AAACATGATGACTACCAAGCTTGGC-3' (SEQ ID NO: 4) and the downstream primer (within the MYC cDNA sequence) 5'-ATGATAGCATCTTGTTCT-TAGTCTTTTTCTTAATAGGG-3' (SEQ ID NO: 5) were used to generate a PCR product of 177 base pairs.

Preparation Of microbubbles (MBs), ultrasound (US) platform, ultrasound-targeted microbubble destruction (UTMD) and BI-97C1 (Sabutoclax). Preparation of MBs followed by UTMD for delivery of mda-7/IL-24 expressing Ads has been described previously (Dash et al., 2011a). Targeson (Targeson) custom synthesis US contrast agent (perfluorocarbon MBs, encapsulated by a lipid monolayer and poly(ethyleneglycol) stabilizer) were obtained. MBs were reconstituted in the presence or absence of 1 ml of $1\times10^{11}$ viral particles of indicated Ads and unenclosed surface-associated Ads were treated with complement as previously described (Cianfriglia et al., 1999; Howard et al., 2006). For in vivo experiments, US exposure was achieved with a Micro-Maxx SonoSite (SonoSite) US machine equipped with the transducer L25 set at 0.7 Mechanical Index, 1.8 MPa for 10 minutes. Mice were sedated in an IMPAQ6 anesthesia apparatus (VetEquip, Pleasanton, Calif.) that was saturated with 3-5% isofluorane and 10-15% oxygen with the aid of a precision vaporizer to deliver the appropriate amount of anesthetic and to induce anesthesia. For microbubble/Ad injection a 27-gauge needle with a heparin lock was placed within a lateral tail vein for administration of contrast material. The mice received injections of 100 μl of MBs with Ads through the tail vein 8 times in the span of 4 weeks. Ultrasound (sonoporation) was performed with a SonoSite scanner (SonoSite) equipped with the transducer L25 set at 0.7 Mechanical Index, 1.8 MPa for 10 min in the ventral side of mice in the prostatic area. BI-97C1 (Sabutoclax) was administered intraperitoneally at a dose level of 3 mg/kg 3× a week for the duration of the study (total 12 injections). Compounds dissolved in 500 μL of solvent (ethanol/Cremophor EL/saline=10:10:80) were injected intraperitoneally. At the end of the experiment, the Hi-Myc mice were sacrificed and the prostate was dissected. The harvested prostate was preserved in neutral buffered formalin at 4° C. before embedding in paraffin for immunohistochemical analysis.

Immunohistochemical staining. For immunohistochemical (IHC) analysis, formalin-fixed and paraffin-embedded specimens were sectioned 3-4-im thick. Sections were deparaffinized, re-hydrated and then quenched in 3% $H_2O_2$ for 20 min. Sections were washed with PBS and blocked in PBS containing 1% BSA for 20 min at 37° C. Monoclonal anti-MDA-7/IL-24 (1:200) was incubated for 3 hr at room temperature and then washed 3× in PBS. Sections were incubated with an avidin-biotin-peroxidase complex (Vectastain Elite ABC kit, Vector Laboratories) and then washed 2× in PBS. The immunoreactivity was determined using diaminobenzidine (DAB) as the final chromogen. Finally, sections were counterstained with Meyer's Hematoxylin, dehydrated through a sequence of increasing concentrations of alcohol, cleared in xylene and mounted with epoxydic medium. Sections were also processed for hematoxylin and eosin (H&E) staining.

Determination of apoptotic cells by TUNEL assay. For TUNEL assays, we used the DeadEnd Colorimetric TUNEL Assay kit (Promega, Madison, Wis.) performed according to the manufacturer's instructions. Briefly, paraffin-embedded slides were deparaffinized and rehydrated. Pre-equilibrated slides were labeled with a labeling DNA-strand break solution containing a biotinylated nucleotide mix (60 min at 37° C.). After several washes in 2×SSC and PBS, slides were blocked with hydrogen peroxide (3-5 min at room temperature). After several washes in PBS, the slides were mounted with mounting solution with DAPI. Apoptotic cells on the slides were observed under an Olympus epifluorescence microscope (×10 magnification; Olympus, Center Valley, Pa.) in randomly chosen fields. For detection of apoptosis in a time-dependent manner in vitro, PC-3 cells were grown in microscopic slide culture chambers (BD Bioscience) and cells were treated with Ad.5/3-CTV (Ad.5/3-CTV-M7) and BI-97C1 (Sabutoclax) after which the cells were fixed with 4% formaldehyde at the indicated time and TUNEL assays were performed as per the manufacturer's instruction using an Olympus epifluorescence microscope (×10 magnification; Olympus, Center Valley, Pa.) (Dash et al., 2011a).

Statistical analysis. Statistical analysis was done using student t test, followed by Fisher's protected least significant difference analysis. P<0.05 was considered significant.

Figure 2A:
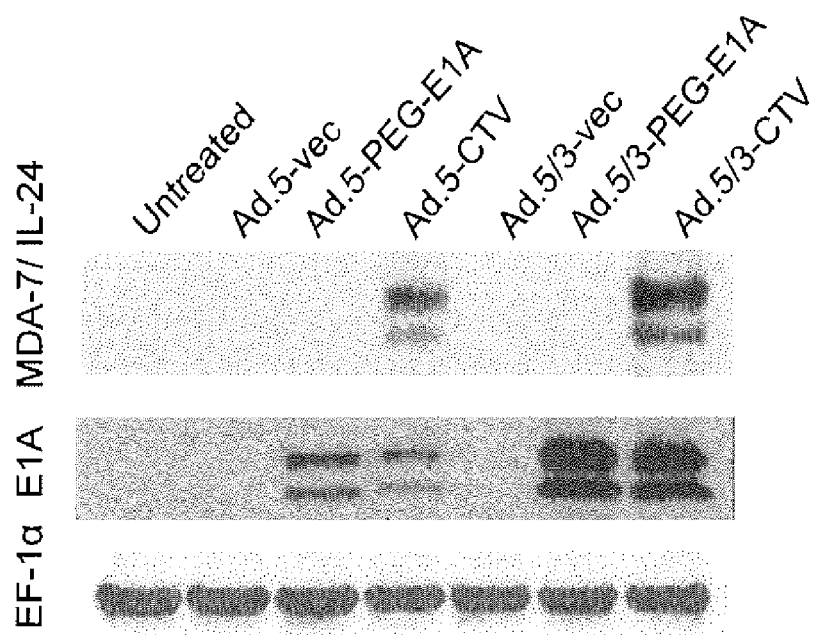
FIG. 2A-D. Ad.513-CTV (Ad.5/3-CTV-M7) enhances mda-7/IL-24 expression and inhibition of cell viability in low CAR prostate cancer cells. A and C) DU-145 and PC-3 cells were infected with the indicated vp/cell of Ad.5-vec, Ad.5-PEG-E1A, Ad.5-CTV (Ad.5-CTV-M7), Ad.5/3-vec, Ad.5/3-PEG-E1A, and Ad.5/3-CTV (Ad.5/3-CTV-M7) for 48 hr and total proteins were isolated. The expression of MDA-7/IL-24 (23.8-kDa protein, with 35- to 40-kDa glycosylated species detected on the gel), E1A and EF-1α (as a loading control) proteins were analyzed by Western blot analyses. B and D) Cell viability using the MTT assay was quantified after 3 days and 6 days with the indicated doses of vp/cell of Ad.5-CTV (Ad.5-CTV-M7), Ad.5/3-CTV (Ad.5/3-CTV-M7) and their respective controls, C and D. Results are the mean±S.D. (n=3).
Figure 2B:
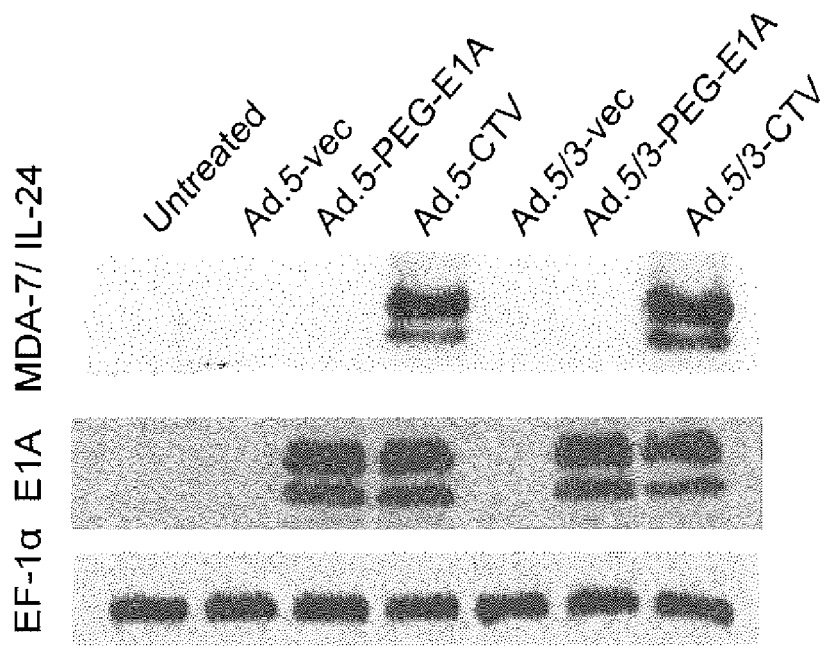

Results:

Ad.5/3-CTV (Ad.5/3-CTV-M7) displays enhanced mda-7/il-24 expression and inhibition of cell viability in low CAR prostate cancer cells The scheme for constructing Ad.5/3-CTV (Ad.5/3-CTV-M7), in which viral replication is controlled by the PEG-Prom and which also expresses mda-7/IL-24 in an Ad.5/3 background, is depicted in FIG. 1 and described in detail in Materials & Methods. As controls we used Ad.5-vec (replication-incompetent empty Ad.5), Ad.5/3-vec (replication-incompetent empty Ad.5/3), Ad.5-PEG-E1A, in which viral replication is controlled by the PEG-Prom in an Ad.5 background, and Ad.5/3-PEG-E1A, in which viral replication is controlled by the PEG-Prom in an Ad.5/3 background. We compared MDA-7/IL-24 expression upon infection of Ad.5/3-CTV (Ad.5/3-CTV-M7) and Ad.5-CTV (Ad.5-CTV-M7) in PC cells that contain low or high CAR on their surface. For this purpose, we used PC-3, which have a reduced level of CAR (D value 0.32) in comparison with DU-145, which express a high level of CAR (D value 0.92) (Dash et al., 2010b; Lebedeva et al., 2003). In PC-3, MDA-7/IL-24 expression was significantly higher upon infection with Ad.5/3-CTV (Ad.5/3-CTV-M7), as compared to Ad.5-CTV (Ad.5-CTV-M7), whereas infection with both Ad.5/3-CTV (Ad.5/3-CTV-M7) and Ad.5-CTV (Ad.5-CTV-M7) in DU-145 resulted in comparable expression of MDA-7/IL-24 protein (FIGS. 2A and 2B). Infection with control Ad vectors did not result in MDA-7/IL-24 expression. These findings indicate that infection with Ad.5/3-CTV (Ad.5/3-CTV-M7) promotes enhanced transgene delivery in low CAR containing PC cells compared to Ad.5-CTV (Ad.5-CTV-M7), and both CTVs are comparable in transgene delivery in high CAR PC cells. An analogous finding was evident when analyzing Ad replication by monitoring E1A protein levels in PC-3 and DU-145 cells (FIGS. 2A and 2B). In DU-145 cells a similar pattern of virus replication was apparent following infection with Ad.5 or Ad.5/3 background viruses, while in PC-3 cells replication of Ad.5/3 was significantly elevated in comparison with infection with Ad.5 (FIGS. 2A and 2B).

Figure 2C:
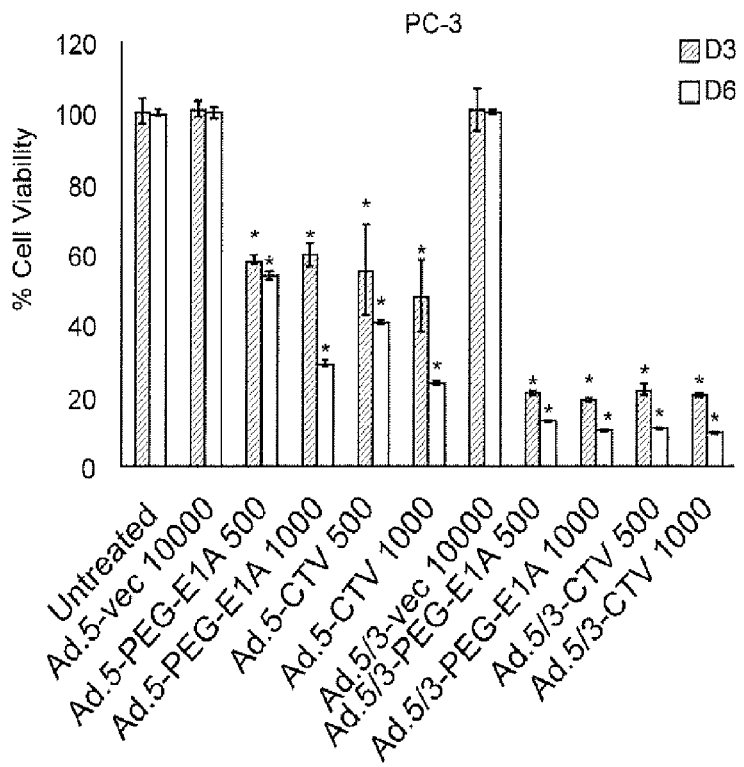
Figure 2D:
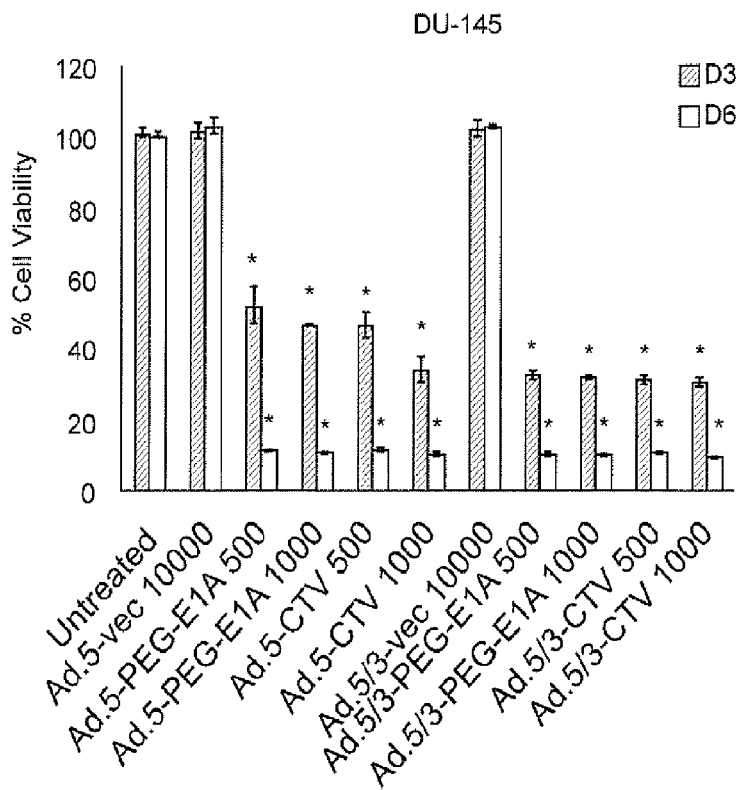

The efficacy of Ad.5/3-CTV (Ad.5/3-CTV-M7) and Ad.5-CTV (Ad.5-CTV-M7) in reducing cell proliferation of PC cells was evaluated in vitro by MTT assays. Ad.5/3-CTV (Ad.5/3-CTV-M7) infection resulted in enhanced reduction in the viability of PC-3 cells as compared to Ad.5-CTV (Ad.5-CTV-M7) infection at m.o.i.'s of 500 and 1000 VP/cell on day 3-post and day 6-post infection (FIG. 2C). In DU-145 cells both Ad.5/3-CTV (Ad.5/3-CTV-M7) and Ad.5-CTV (Ad.5-CTV-M7) showed parallel efficiencies in reducing growth when assayed using equivalent viral titers and evaluated at parallel time points (FIG. 2D). It should be noted that Ad.5-PEG-E1A and Ad.5/3-PEG-E1A was as effective as Ad.5-CTV (Ad.5-CTV-M7) and Ad.5/3-CTV (Ad.5/3-CTV-M7) in reducing cell viability in both cell lines indicating that the profound effect of Ad replication in inhibiting cell viability might mask the in vitro growth inhibitory effects of mda-7/IL-24. In these contexts, in vivo evaluation of CTV is mandatory to confirm the 'antitumor bystander' effect exerted by MDA-7/IL-24.

Figure 3A:
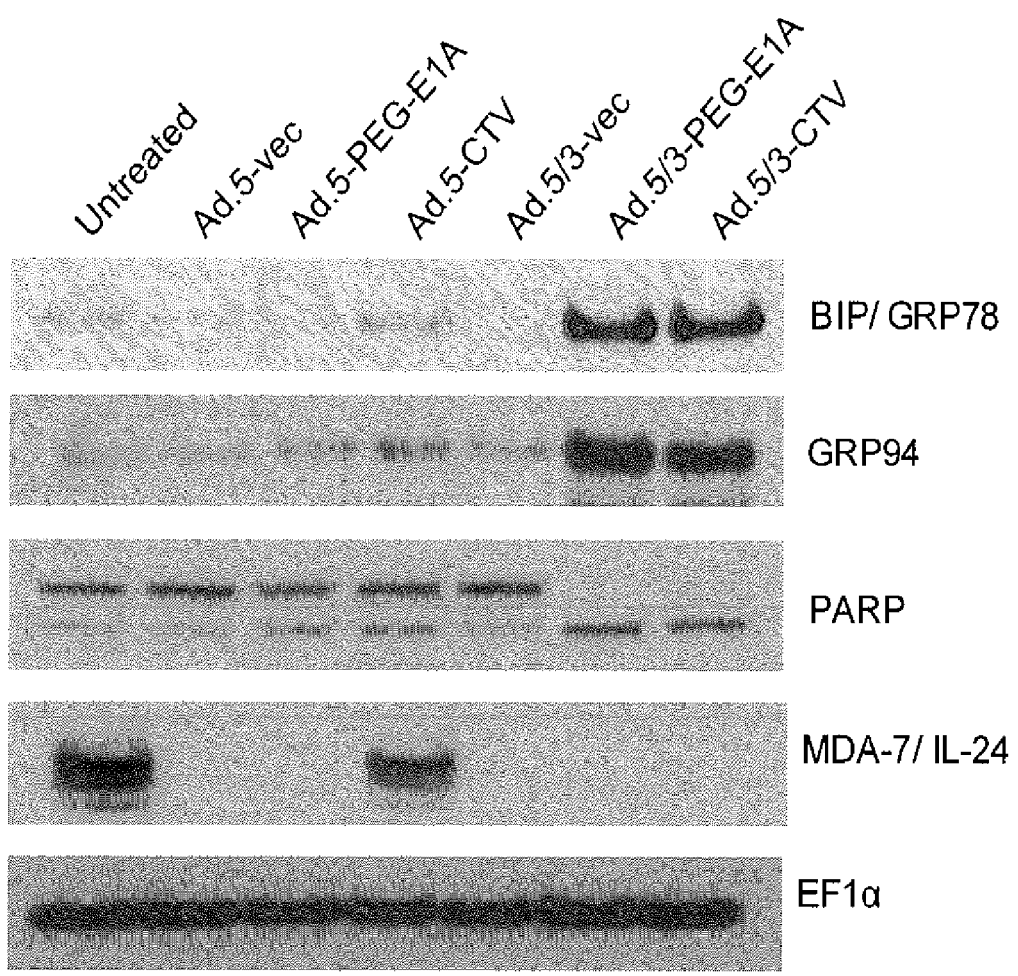
FIG. 3A-C. Ad.5/3-CTV (Ad.5/3-CTV-M7), but not Ad.5-CTV (Ad.5-CTV-M7), induce ER stress and apoptosis, and overcome therapy resistance in PC-3-Bcl-2 tumor cells. a)

Ad.5/3-CTV (Ad.5/3-CTV-M7), but not Ad.5-CTV (Ad.5-CTV-M7), Induces ER Stress and Apoptosis, and Overcomes Therapy Resistance in PC-3-Bcl-2 Tumor Cells We next analyzed the expression of mda-7/IL-24-downstream genes and signals that confer its tumor suppressor properties upon infection with Ad.5/3-CTV (Ad.5/3-CTV-M7) and Ad.5-CTV (Ad.5-CTV-M7) in low CAR PC-3 cells. Ad.5/3-CTV (Ad.5/3-CTV-M7) induces an ER stress response (unfolded-protein response) and we therefore determined the expression levels of ER-stress markers. In PC-3-Neo cells, the levels of BiP/GRP78 and GRP94 were significantly higher upon infection with Ad.5/3-CTV (Ad.5/3-CTV-M7) as compared with Ad.5-CTV (Ad.5-CTV-M7). Ad.5/3-CTV (Ad.5/3-CTV-M7) also efficiently induced apoptosis as evidenced by increased cleavage of PARP (FIG. 3A). It should be noted, that infection with the conditionally replication competent Ad.5/3, Ad.5/3-PEG-E1A, also induced a stress response, as did Ad.5/3-CTV (Ad.5/3-CTV-M7), as indicated by enhanced BiP/GRP78, GRP94 and PARP cleavage (FIG. 3A). However, this effect was not evident with Ad.5-PEG-E1A or Ad.5-CTV (Ad.5-CTV-M7) infection.

Figure 3B:
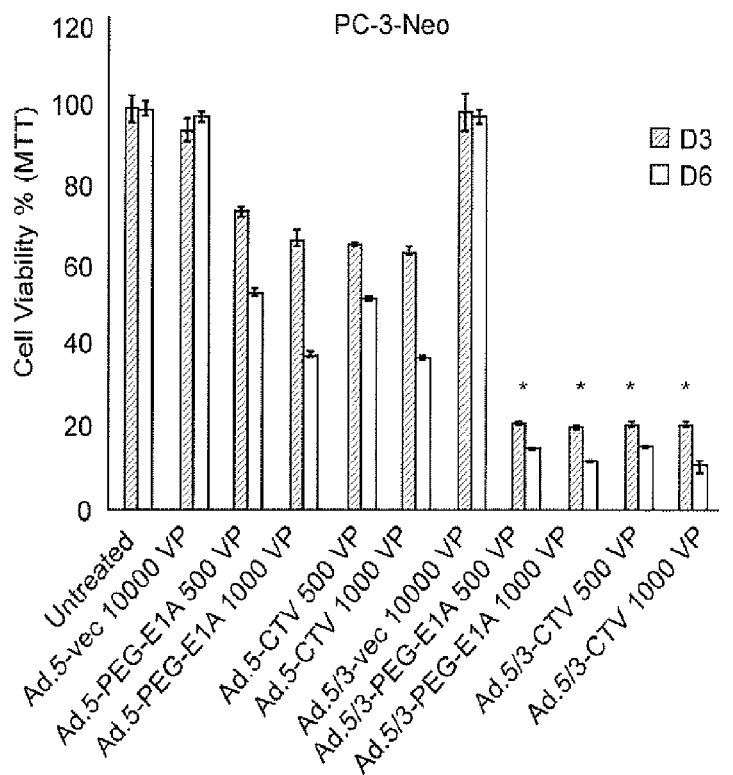
Figure 3C:
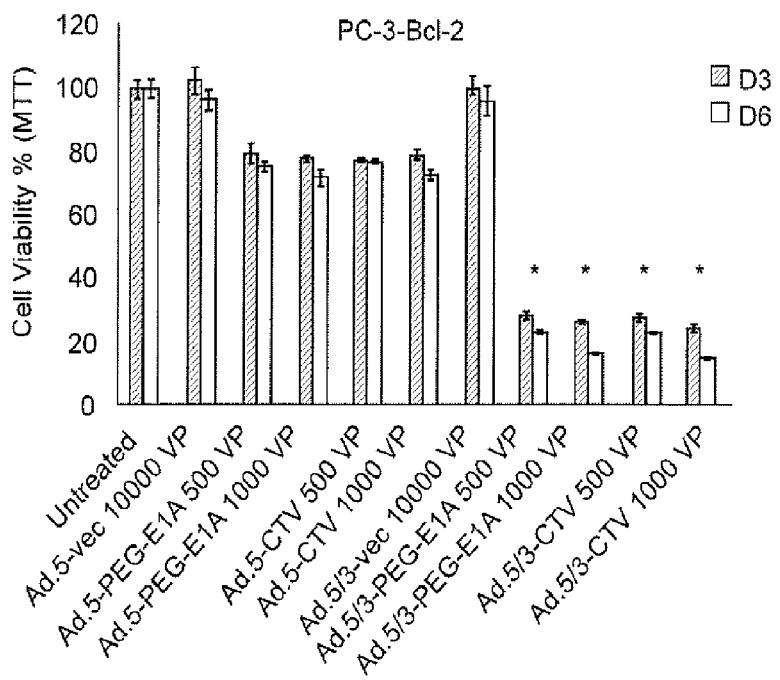

The Bcl-2 gene family plays a central role in PC and over expression of Bcl-2 gene family members confers resistance to specific cancer therapeutics (Lebedeva et al., 2003). In this context, we evaluated the efficacy of Ad.5/3-CTV (Ad.5/3-CTV-M7) vs. Ad.5-CTV (Ad.5-CTV-M7) in PC-3-Bcl-2 cells (PC-3 cells that stably over express Bcl-2), which are resistant to mda-7/IL-24-mediated killing (Lebedeva et al., 2003). As control, we used PC-3-Neo cells that are stably transformed with the same vector expressing only the neomycin resistance gene and not the Bcl-2 gene. In MTT assays, Ad.5-PEG-E1A and Ad.5-CTV (Ad.5-CTV-M7) were less effective in inhibiting cell proliferation (viability) of PC-3-Bcl-2, whereas PC3-Neo cells were sensitive to these viruses (FIGS. 3B and 3C). Accordingly, the effect of Ad.5-CTV was more robust in suppressing growth of PC-3-Neo as compared to PC-3-Bcl-2 cells, whereas the Ad.5/3-CTV (Ad.5/3-CTV-M7) displayed equivalent vigorous in vitro anti-proliferative activity in both cell types (FIGS. 3B and 3C). These findings support the enhanced potential therapeutic application of Ad.5/3-CTV (Ad.5/3-CTV-M7) vs. Ad.5-CTV (Ad.5-CTV-M7) in PC patients frequently showing Bcl-2 over expression and down-regulation of CAR.

Figure 4A:
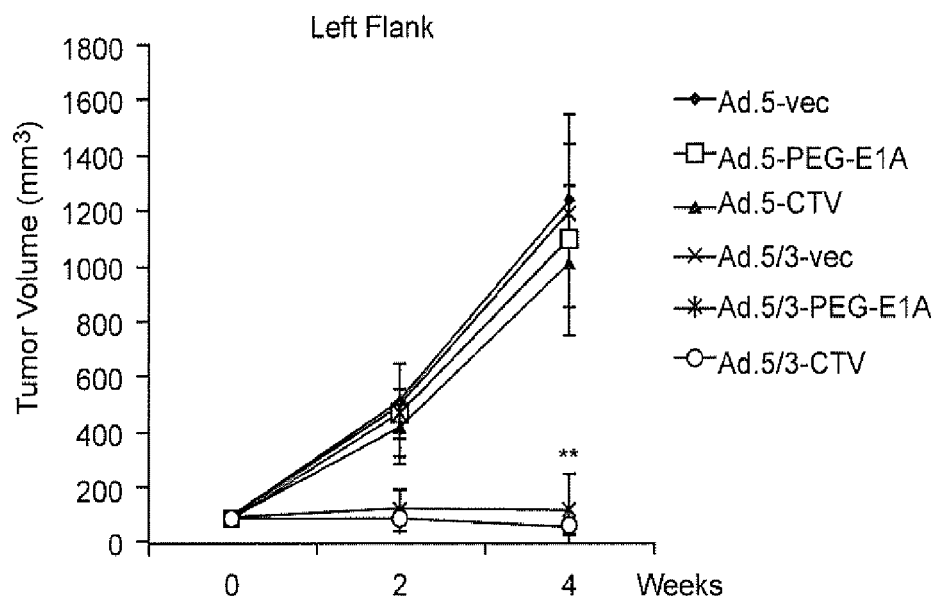
Figure 4B:
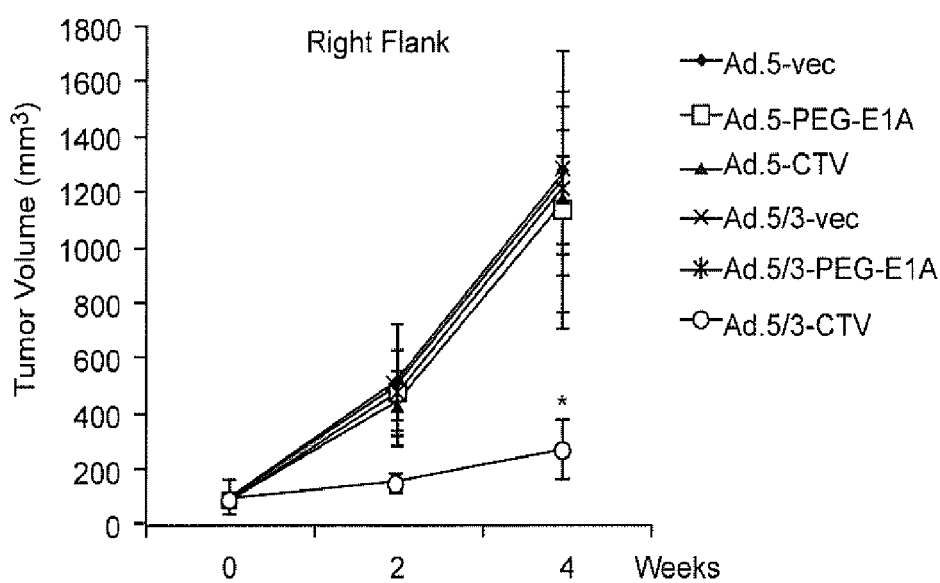
Figure 4C:
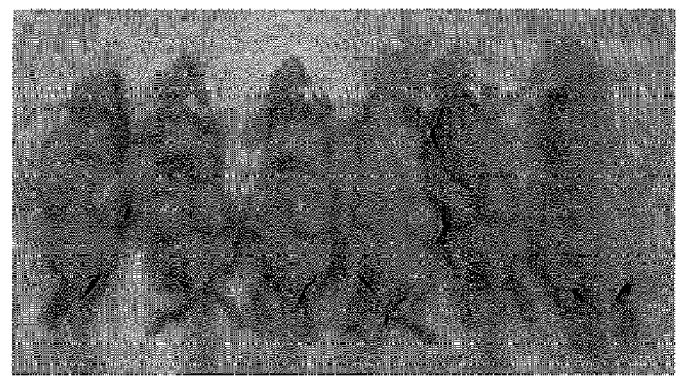
Figure 4D:
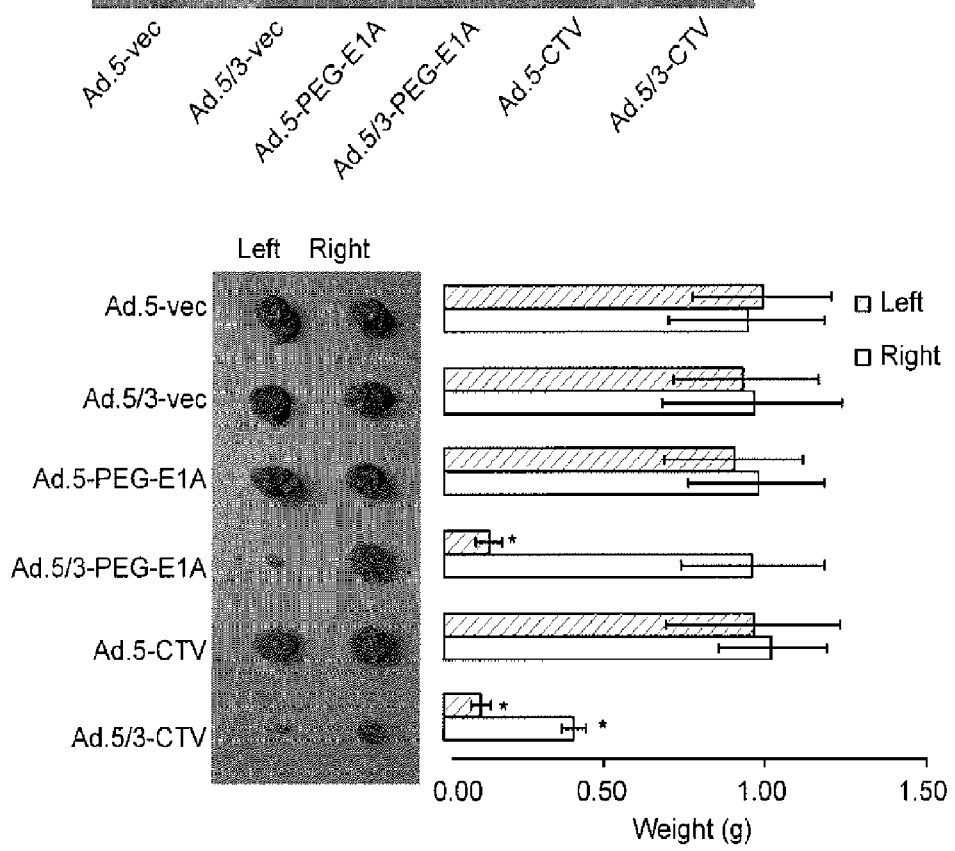
Figure 4E:
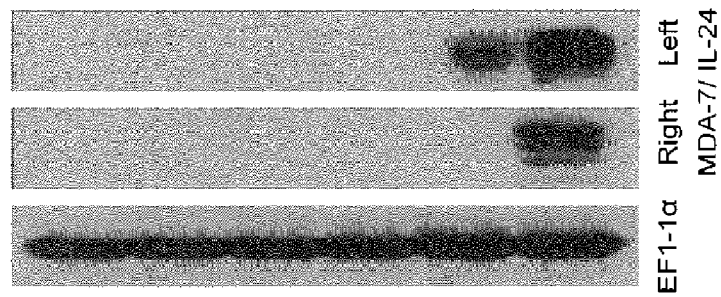

Ad.5/3-CTV (Ad.5/3-CTV-M7) Eradicates Primary and Inhibits Distant PC-3-Bcl-2 Xenografts in Nude Mice Experiments were performed to determine if the enhanced in vitro activity of Ad.5/3-CTV (Ad.5/3-CTV-M7) compared to Ad.5-CTV (Ad.5-CTV-M7) in low CAR PC-3-Bcl-2 cells translates into enhanced in vivo activity. PC-3-Bcl-2 tumor cells were inoculated in both the right and left flanks of athymic nude mice. After ~7 to 10 days palpable tumor xenografts of ~100 mm$^3$ developed and the mice received 8 intratumoral injections only in the left flank tumors over a 4-week period with 1×10$^{10}$ viral particles per 100 µL. The Ads used for this study included Ad.5-vec, Ad.5/3-vec, Ad.5-PEG-E1A, Ad.5/3-PEG-E1A, Ad.5-CTV (Ad.5-CTV-M7) and Ad.5/3-CTV (Ad.5/3-CTV-M7). No injections were administrated to right flank tumors. PC-3-Bcl-2 formed large, aggressive and actively proliferating tumors on both flanks that were not affected by treatment with Ad.5-vec, Ad.5/3-vec, Ad.5-PEG-E1A or Ad.5-CTV (Ad.5-CTV-M7). Although Ad.5/3-PEG-E1A inhibited the growth of tumors on the left flank, it had no effect on the distant tumors on the right flank (FIGS. 4A, 4B, 4C and 4D). In contrast, Ad.5/3-CTV (Ad.5/3-CTV-M7) dramatically inhibited tumor growth on the injected left flank and markedly inhibited tumor growth on the right flank, exceeding the therapeutic effect of any other viral treatment. These results provide definitive evidence for enhanced therapeutic efficacy of Ad.5/3-CTV (Ad.5/3-CTV-M7) as compared to Ad.5-CTV (Ad.5-CTV-M7) in prostate tumor cells with reduced CAR, and highlight the potent 'bystander anticancer' activity of mda-7/IL-24 resulting in growth inhibition of right-side, non-injected tumors. The effectiveness of Ad.5/3-CTV (Ad.5/3-CTV-M7) and Ad.5-CTV (Ad.5-CTV-M7) in transducing MDA-7/IL-24 in vivo was confirmed by Western blotting using total protein extracts from the harvested tumors and probing with MDA-7/IL-24 antibody. Ad.5/3-CTV (Ad.5/3-CTV-M7) generated more MDA-7/IL-24 protein in both flanks, validating the previously reported "bystander antitumor" effect of MDA-7/IL-24 (Chada et al., 2004; Lebedeva et al., 2007a; Sarkar et al., 2007b; Su et al., 2005a; Su et al., 2001a). In contrast, only weak MDA-7/IL-24 protein expression was evident in Ad.5-CTV (Ad.5-CTV-M7) injected PC-3-Bcl-2 tumor (left flank) and no protein expression was evident on the right flank tumor (FIG. 4E). These findings demonstrate that in low CAR PC cells, Ad.5/3-CTV (Ad.5/3-CTV-M7) can generate robust expression of MDA-7/IL-24 protein that is sufficient to inhibit tumor cell proliferation, and exert 'bystander antitumor' activity mediated by MDA-7/IL-24 in distant tumors.

Combination Treatment of Ad.5/3-CTV (Ad.5/3-CTV-M7) and BI-97C1 (Sabutoclax) Potentiates Inhibition of Prostate Tumor Growth In Vivo in Immune Competent Animals Because PC is a relatively slow-growing disease, repeated systemic gene therapy applications in combination with anti-tumor chemotherapeutic agents over the life span of the patient may be necessary to provide enduring clinical responses (Damber and Aus, 2008; Di Lorenzo and De Placido, 2006). Previous studies demonstrated that BI-97C1 (Sabutoclax), which is a pure optical derivative of Apogossypol (Wei et al., 2010), has significant activity as a single agent against PC cells in vitro and in vivo in nude mouse xenograft studies. Apogossypol derivatives antagonize the antiapoptotic Bcl-2 family members including Bcl-2 and Mcl-1 (Wei et al., 2009). MDA-7/IL-24 induces cancer-specific apoptosis through the translational inhibition of Mcl-1(Dash et al., 2010c). BI-97C1 (Sabutoclax) sensitizes prostate cancer cells to mda-7/IL-24-mediated toxicity in vitro and in vivo (Dash et al., 2011a).

Experiments were performed to determine if Ad.5/3-CTV (Ad.5/3-CTV-M7) in combination with BI-97C1 could also inhibit prostate tumor growth in vivo. For this analysis we used an immunocompetent transgenic mouse model of prostate cancer (the Hi-Myc mouse) that spontaneously develops PC. In Hi-Myc mice, prostate-specific c-Myc gene expression is controlled through the rat probasin promoter with two androgen response elements (ARR2/probasin promoter). Hi-Myc mice develop prostatic intraepithelial neoplasia (mPIN) as early as 2 to 4 weeks of age and invasive adenocarcinoma of the prostate at 6 months (Ellwood-Yen et al., 2003). Treatment was initiated at 22 weeks of age. The ability to deliver adenoviruses systemically is limited by sequestering of the virus in the liver and clearance of the virus by the immune system (Koizumi et al., 2007; Muruve, 2004; Schenk et al., 2010). To overcome these formidable problems we employed a microbubble-targeted ultrasound destruction (UTMD) approach (Das et al., 2012; Greco et al., 2010; Howard et al., 2006; Lu et al., 2003) in which microbubbles incorporating adenoviruses are targeted to release therapeutic viruses at the tumor site using ultrasound. Using ultrasound to sonicate the microbubbles creates transient nonlethal perforations in cells and other membranes. In this way, systemic and targeted delivery of mda-7/IL-24 to the prostate of Hi-Myc mice was performed by tail vein injection of microbubbles (MB) incorporating Ad.5/3-vec, Ad.5/3-PEG-E1A or Ad.5/3-CTV (Ad.5/3-CTV-M7) followed by sonoporation in the prostatic area (Dash et al., 2011a). A total of 8 tail vein injections of each adenovirus were administered over a 4-week period. BI-97C1 was administered intraperitoneally (i.p.) in each group at 3 mg/kg 3× a week throughout the study. The prostates of Hi-myc mice were sectioned and stained for MDA-7/IL-24 and Ki-67, proliferation marker, and apoptosis induction was analyzed by TUNEL assay. MDA-7/IL-24 expression was accompanied by increased TUNEL positive cells and decreased Ki-67 positive cells in the Ad.5/3-CTV (Ad.5/3-CTV-M7) and BI-97C1-treated group compared to the control groups (FIGS. 5A-C). Although, Ad.5/3-CTV (Ad.5/3-CTV-M7) alone induced significant apoptosis it was markedly augmented when used in combination with BI-97C1.

Discussion

The progression of PC is often slow and different therapeutics may be required during various stages of this process and at multiple times during the life of the patient. In the context of gene therapy, it may be necessary to employ different genes, used alone or in combination, and viral or non-viral gene delivery approaches over extended periods of time (Dash et al., 2010a, 2011a, 2011b). Accordingly, the use of conditionally replicating adenoviruses to administer therapeutic genes in prostate tumor cells represents a potentially viable treatment option (Sarkar et al., 2005a. 2005b, 2006, 2007, 2008; Curiel and Fisher, 2012; Das et al., 2012). A major challenge for effective gene therapy using non-replicating as well as conditionally replicating Ads is the ability to specifically deliver nucleic acids directly into diseased tissue. Additionally, progress in gene therapy has been hampered by concerns over the safety and utility of viral vectors, particularly for intravenous delivery, and the inefficiency of currently available non-viral transfection techniques (Dash et al., 2011b; Curiel and Fisher, 2012).

Recombinant Ads are one of the most common gene transfer vectors utilized in human clinical trials, but systemic administration of this virus is thwarted by host innate and adaptive antiviral immune responses which can limit and/or preclude repetitive treatment regiments (Jiang et al., 2004; Curiel and Fisher, 2012). Systemic delivery of Ads is also restricted because of non-specific trapping in the liver, preventing virus from reaching the diseased cells disseminated throughout the body. We have identified a superior gene therapy approach that employs a novel therapeutic gene mda-7/IL-24, a unique member of the IL-10 gene family of cytokines (Jiang et al., 1995, 1996; Fisher et al., 2003, 2007; Fisher, 2005; Lebedeva et al., 2005, 2007; Emdad et al., 2009; Dash et al., 2010a). Early phase I clinical studies suggest that mda-7/IL-24 may be an ideal agent for gene therapy of advanced cancers, including carcinomas from multiple organs and melanomas (Fisher et al., 2003, 2007; Cunningham et al., 2005; Tong et al., 2005; Eager et al., 2008). mda-7/IL-24 selectively induces apoptosis or toxic autophagy in a broad spectrum of human cancer cells in vitro and in vivo in animal models, whereas it appears devoid of toxicity in diverse normal human cells (Jiang et al, 1996; Huang et al., 2001; Sarkar et al., 2002a, 2005a, 2005b; Sauane et al., 2003, 2006, 2008; Fisher et al., 2003, 2007; Fisher, 2005; Lebedeva et al., 2005, 2007; Cunningham et al., 2005; Tong et al., 2005; Bhutia et al., 2010; Das et al., 2010a; Hamed et al., 2010b). Additionally, MDA-7/IL-24 is a secreted cytokine that exhibits potent direct and indirect "bystander antitumor" effects on adjacent and distant cancer cells (Su et al., 2001b, 2005a; Wolk et al., 2002; Chada et al., 2004; Fisher, 2005; Dash et al., 2010a).

The ability of type 5 Ad (Ad.5) to infect mammalian cells is dependent on the level of CAR on the cell surface. This limitation and correlation between infectivity and levels of CAR expression in human PC cells has been demonstrated previously (Okegawa et al., 2000; Pandha et al., 2003; Curiel and Fisher, 2012). DU-145 has high CAR, while PC-3 has lower cell surface CAR expression, which makes it relatively resistant to Ad.5 infection. To overcome resistance of PC-3 to Ad.5 infection, PC-3 cells have been genetically engineered to increase the original 35% CAR found in low CAR-positive cells to 86% CAR-positive cells (Okegawa et al., 2000). Consequently, infection with a recombinant Ad.5-CMV-p21 virus resulted in higher levels of p21 protein in the genetically altered PC-3 (enhanced CAR positive) virus-infected cells, thereby resulting in apoptosis (Okegawa et al., 2000). These studies highlight the importance of CAR as a major determinant of Ad.5-based gene therapy approaches.

To enhance therapeutic efficacy of Ad gene therapy we have used a number of approaches. We constructed a bipartite Ad.5 where viral replication is controlled by the minimal active region of the promoter of the PEG-3 gene (Su et al., 1997, 2005b), restricting viral replication to cancer cells with limited activity in normal cells, and mda-7/IL-24 is driven by a CMV promoter from the E3 region of Ad.5 (Sarkar et al., 2005a, 2006, 2007, 2008). These viruses, termed Cancer Terminator Viruses (CTVs) (reviewed in Das et al., 2012), have shown profound activity in athymic nude mouse human xenograft models, including breast carcinomas, prostate cancer (including therapy-resistant prostate cancers over expressing Bcl-2 or Bcl-$X_L$) and metastatic melanoma (Sarkar et al., 2005a, 2006, 2007, 2008; Greco et al., 2010). The enhanced therapeutic activity of the CTV relates to the profound direct apoptosis- and toxic autophagy-inducing effects and indirect antitumor activity of this secreted cytokine through its "bystander" effects, which include inhibition of tumor angiogenesis, synergism with other modes of cancer therapy (including chemotherapy, radiation and monoclonal antibodies) and promotion of a potent immune response against the tumor (Fisher, 2005; Lebedeva et al., 2007; Sarkar et al., 2007; Gao et al., 2008).

To enhance viral entry into cancer cells, many of which show downregulation of CAR, we engineered chimeric adenoviruses containing the Ad.3 sequence within the Ad.5 virus knob (Ad.5/3) (Dash et al., 2010b; Azab et al., 2012), which redirects binding of the vector to the Ad.3 receptor, desmoglein 2 (Wang et al., 2011). The finding that Ad.5/3-CTV (Ad.5/3-CTV-M7) eradicated not only primary injected tumors, but also distant non-injected tumors derived from a resistant PC cell line in a nude mouse xenograft model support the anticancer potency of this cancer therapeutic virus. As discussed, Ad.5/3-CTV (Ad.5/3-CTV-M7) is capable of infecting cancer cells regardless of their cell surface CAR status, which makes it potentially more efficacious than Ad.5-CTV (Ad.5/3-CTV-M7) that fails to efficiently infect and deliver the therapeutic genes in low CAR PC cells.

Systematic delivery of Ads is challenging because of sequestration of viruses in the liver restricting efficient delivery to disseminated tumors (Koizumi et al., 2007) and neutralization of viruses by the immune system (Koizumi et al., 2007). To prevent trapping of CTV in the liver and elimination of viruses by the immune system we have developed an innovative approach that involves the use of perfluorocarbon microbubbles and ultrasound (Greco et al., 2010; Dash et al., 2011a, 2011b). This approach is called ultrasound-targeted microbubble-destruction (UTMD). We have applied the UTMD approach using a tropism-modified Ad.5/3-CTV in Hi-Myc transgenic mice, which develop PC (Ellwood-Yen et al., 2003; Dash et al., 2011a). Ad.5/3-CTV (Ad.5/3-CTV-M7) in complement-treated microbubbles were administered systemically through the tail vein of mice and released in the prostate area through ultrasound in this syngeneic immunocompetent prostate cancer mouse model (Hi-Myc mouse) using UTMD (Dash et al., 2011a, 2011b). Hi-Myc mice develop, with high penetrance, prostatic intraepithelial neoplasia (PIN) that advances over time to invasive adenocarcinomas in all lobes of the prostate gland (Ellwood-Yen et al., 2003). In the present study show the combinatorial anticancer effect of Ad.5/3-CTV (Ad.5/3-CTV-M7) and the novel Mcl-1 antagonist, BI-97C1 (Sabutoclax), which significantly inhibits PC in Hi-Myc transgenic mice. For combination studies we chose an Mcl-1 antagonist based on our previous observations where we demonstrated that suppression of the pro-survival Bcl-2 family member, myeloid cell leukemia-1 (Mcl-1), is required for mda-7/IL-24-mediated apoptosis of prostate carcinomas (Dash et al., 2010c; Dash et al., 2011a). Here we demonstrate that pharmacological inhibition of Mcl-1 expression with the novel Apogossypol derivative BI-97C1 is sufficient to sensitize prostate tumors to mda-7/IL-24-induced (Ad.5/3-CTV) apoptosis.

In summary,

1) The prostate gland is not vital for survival and it is accessible by ultrasound.

2) Ad.5/3-CTV (Ad.5/3-CTV-M7) can be either injected directly into the primary tumor or delivered through UTMD with complement-treated microbubbles incorporating Ads resulting in cancer cell lysis and expression of MDA-7/IL-24 when ultrasound is applied.

3) The replication of this virus and the expression of the therapeutic genes can be targeted in cancer cells without non-specific expression in normal cells by using the cancer-specific and tissue-specific PEG-3 promoter.

4) Disease progression can be effectively monitored by measuring prostate-specific antigen (PSA) (Cookson, 2001; Gopalkrishnan et al., 2001). In these contexts, the use of Ad.5/3-CTV (Ad.5/3-CTV-M7) to administer the therapeutic and cancer-specific cytotoxic mda-7/IL-24 protein to selectively induce cytolysis and apoptosis in prostate tumor cells represents a potentially viable treatment option (Anderson, 1998; Sarkar et al., 2007; Das et al., 2012).

References For Example 1

Anderson, W F. 1998. Human gene therapy. Nature 392: 25-30.

Azab, B, Dash, R, Das, S K, Bhutia, S K, Shen, X N, Quinn, B A, Sarkar, S, Wang, X Y, Hedvat, M, Dmitriev, I P, Curiel, D T, Grant, S, Dent, P, Reed, J C, Pellecchia, M, Sarkar, D, and Fisher, P B. 2012. Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells. J Cellular Physiol, 227: 2145-2153.

Bhang, H-e, Gabrielson, K L, Laterra, J, Fisher, P B, and Pomper, M G. 2011. Tumor-specific imaging through progression elevated gene-3 promoter-driven gene expression. Nature Med 17: 123-129.

Bhutia, S K, Dash, R, Das, S K, Azab, B, Su, Z Z, Lee, S G, Grant, S, Yacoub, A, Dent, P, Curiel, D T, Sarkar, D, and Fisher, P B. 2010. Mechanism of autophagy to apoptosis switch triggered in prostate cancer cells by antitumor cytokine melanoma differentiation-associated gene 7/interleukin-24. Cancer Res 70: 3667-3676.

Chada, S, Mhashilkar, A M, Ramesh, R, Mumm, J B, Sutton, R B, Bocangel, D, Zheng, M, Grimm, E A, and Ekmekcioglu, S. 2004. Bystander activity of Ad-mda7: human MDA-7 protein kills melanoma cells via an IL-20 receptor-dependent but STAT3-independent mechanism. Mol Ther 10: 1085-1095.

Cookson, M M. 2001. Prostate cancer: screening and early detection. Cancer Control 8: 133-140.

Cunningham, C C, Chada, S, Merritt, J A, Tong, A, Senzer, N, Zhang, Y, Mhashilkar, A, Parker, K, Vukelja, S, Richards, D, Hood, J, Coffee, K, and Nemunaitis, J. 2005. Clinical and local biological effects of an intratumoral injection of mda-7 (IL24; INGN 241) in patients with advanced carcinoma: a phase I study. Mol Ther 11: 149-159.

Curiel D T, and Fisher P B. 2012. Applications of viruses for cancer therapy. Tew K D and Fisher P B (series editors). Adv Cancer Res 115: 1-334.

Damber J E, A G. 2008. Prostate cancer. Lancet 371: 1710-1721.

Dash, R, Bhutia, S K, Azab, B, Su, Zz, Quinn, B A, Kegelmen, T P, Das, S K, Kim, K, Lee, S G, Park, M A, Yacoub, A, Rahmani, M, Emdad, L, Dmitriev, I P, Wang, X Y, Sarkar, D, Grant, S, Dent, P, Curiel, D T, and Fisher, P B. 2010a. mda-7/IL-24: a unique member of the IL-10 gene family promoting cancer-specific toxicity. Cytokine & Growth Factor Rev 21: 381-391.

Dash, R, Dmitriev, I, Su, Z Z, Bhutia, S K, Azab, B, Vozhilla, N, Yacoub, A, Dent, P, Curiel, D T, Sarkar, D, and Fisher, P B. 2010b. Enhanced delivery of mda-7/IL-24 using a serotype chimeric adenovirus (Ad.5/3) improves therapeutic efficacy in low CAR prostate cancer cells. Cancer Gene Ther 17: 447-456.

Dash, R, Richards, J E, Su, Z Z, Bhutia, S K, Azab, B, Rahmani, M, Dasmahapatra, G, Yacoub, A, Dent, P, Dmitriev, I P, Curiel, D T, Grant, S, Pellecchia, M, Reed, J C, Sarkar, D, and Fisher, P B. 2010c. Mechanism by which Mcl-1 regulates cancer-specific apoptosis triggered by mda-7/IL-24, an IL-10-related cytokine. Cancer Res 70: 5034-5045.

Dash, R, Azab, B, Quinn, B A, Shen, X, Wang, X Y, Das, S K, Rahmani, M, Wei, J, Hedvat, M, Dent, P, Dmitriev, I P, Curiel, D T, Grant, S, Wu, B, Stebbins, J L, Pellecchia, M, Reed, J C, Sarkar, D, and Fisher, P B. 2011a. Apogossypol derivative BI-97C1 (Sabutoclax) targeting Mcl-1 sensitizes prostate cancer cells to mda-7/IL-24-mediated toxicity. Proc Natl Acad Sci USA 108: 8785-8790.

Dash, R, Azab, B, Shen, X N, Sokhi, U K, Sarkar, S, Su, Z Z, Wang, X Y, Claudio, P P, Dent, P, Dmitriev, I P, Curiel, D T, Grant, S, Sarkar, D, and Fisher, P B. 2011b. Developing an effective gene therapy for prostate cancer: new technologies with potential to translate from the laboratory into the clinic. Discov Med 11: 46-56.

Di Lorenzo, G, and De Placido, S. 2006. Hormone refractory prostate cancer (HRPC): present and future approaches of therapy. Int J Immunopathol Pharmacol 19: 11-34.

Ellwood-Yen, K, Graeber, T G, Wongvipat, J, Iruela-Arispe, M L, Zhang, J, Matusik, R, Thomas, G V, and Sawyers, C L. 2003. Myc-driven murine prostate cancer shares molecular features with human prostate tumors. Cancer Cell 4: 223-238.

Emdad, L, Lebedeva, I V, Su, Z-z, Gupta, P, Sauane, M, Dash, R, Grant, S, Dent, P, Curiel, D T, Sarkar, D, and Fisher, P B. 2009. Historical perspective and recent insights into our understanding of the molecular and biochemical basis of the antitumor properties of mda-7/IL-24. Cancer Biol & Ther 8: 391-400.

Eulitt, P J, Park, M A, Hossein, H, Cruikshanks, N, Yang, C, Dmitriev, I P, Yacoub, A, Curiel, D T, Fisher, P B, and Dent, P. 2011. Enhancing mda-7/IL-24 therapy in renal carcinoma cells by inhibiting multiple protective signaling pathways using sorafenib and by Ad.5/3 gene delivery. Cancer Biol Ther 10: 1290-1305.

Fisher, P B. 2005. Is mda-7/IL-24 a 'magic bullet' for cancer? Cancer Res 65: 10128-10138.

Fisher, P B, Gopalkrishnan, R V, Chada, S, Ramesh, R, Grimm, E A, Rosenfeld, M R, Curiel, D T, and Dent, P. 2003. mda-7/IL-24: A novel cancer selective apoptosis inducing cytokine gene: From the laboratory into the clinic. Cancer Biol Therapy 2: S23-S37.

Fisher P B, Sarkar D, Lebedeva I V, Emdad L, Gupta P, Sauane M, Su Z-z, Grant S, Dent P, Curiel D T, Senzer N, Nemunaitis J. 2007. Melanoma differentiation associated gene-7/interleukin-24 (mda-7/IL-24): novel gene therapeutic for metastatic melanoma. Toxicol & Applied Pharmacol 224: 300-307.

Gao, P, Sun, X, Chen, X, Wang, Y, Foster, B A, Subjeck, J, Fisher, P B, and Wang, X Y. 2008. Secretable chaperone Grp 170 enhances therapeutic activity of a novel tumor suppressor, mda-7/IL-24. Cancer Res 68: 3890-3898.

Gopalkrishnan, R V, Kang, D C, and Fisher, P B. 2001. Molecular markers and determinants of prostate cancer metastasis. J Cell Physiol 189: 245-256.

Greco, A, Di Benedetto, A, Howard, C M, Kelly, S, Nande, R, Dementieva, Y, Miranda, M, Brunetti, A, Salvatore, M, Claudio, L, Sarkar, D, Dent, P, Curiel, D T, Fisher, P B, and Claudio, P P. 2010. Eradication of Therapy-resistant Human Prostate Tumors Using an Ultrasound-guided Site-specific Cancer Terminator Virus Delivery Approach. Mol Ther 18: 295-306.

Hamed, H A, Yacoub, A, Park, M A, Eulitt, P J, Dash, R, Sarkar, D, Dmitriev, I P, Lesniak, MS, Shah, K, Grant, S, Curiel, D T, Fisher, P B, and Dent, P. 2010a. Inhibition of multiple protective signaling pathways and Ad.5/3 delivery enhances mda-7/IL-24 therapy of malignant glioma. Mol Ther 18: 1130-1142.

Hamed, H A, Yacoub, A, Park, M A, Eulitt, P, Sarkar, D, Dmitriev, I P, Chen, C-S, Grant, S, Curiel, D T, Fisher, P B, and Dent, P. 2010b. OSU-03012 enhances Ad.mda-7-induced GBM cell killing via ER stress and autophagy and by decreasing expression of mitochondrial protective proteins. Cancer Biol & Ther 9: 526-536.

Howard, C M, Forsberg, F, Minimo, C, Liu, J B, Merton, D A, and Claudio, P P. 2006. Ultrasound guided site specific gene delivery system using adenoviral vectors and commercial ultrasound contrast agents. J Cell Physiol 209: 413-421.

Huang, E Y, Madireddi, M T, Gopalkrishnan, R V, Leszczyniecka, M, Su, Z, Lebedeva, I V, Kang, D, Jiang, H, Lin, J J, Alexandre, D, Chen, Y, Vozhilla, N, Mei, M X, Christiansen, K A, Sivo, F, Goldstein, N I, Mhashilkar, A B, Chada, S, Huberman, E, Pestka, S, and Fisher, P B. 2001. Genomic structure, chromosomal localization and expression profile of a novel melanoma differentiation associated (mda-7) gene with cancer specific growth suppressing and apoptosis inducing properties. Oncogene 20: 7051-7063.

Jiang, H, and Fisher P B. 2003. Use of a sensitive and efficient subtraction hybridization protocol for the identification of genes differentially regulated during the induction of differentiation in human melanoma cells. Mol Cell Different 1: 285-299.

Jiang, H, Lin, J J, Su, Z Z, Goldstein, N I, and Fisher, P B. 1995. Subtraction hybridization identifies a novel melanoma differentiation associated gene, mda-7, modulated during human melanoma differentiation, growth and progression. Oncogene 11: 2477-2486.

Jiang, H, Su, Z Z, Lin, J J, Goldstein, N I, Young, C S, and Fisher, P B. 1996. The melanoma differentiation associated gene mda-7 suppresses cancer cell growth. Proc Natl Acad Sci U S A 93: 9160-9165.

Jiang, H, Wang, Z, Serra, D, Frank, M M, and Amalfitano, A. 2004. Recombinant adenovirus vectors activate the alternative complement pathway, leading to the binding of human complement protein C3 independent of anti-ad antibodies. Mol Ther 10: 1140-1142.

Koizumi, N, Yamaguchi, T, Kawabata, K, Sakurai, F, Sasaki, T, Watanabe, Y, Hayakawa, T, and Mizuguchi, H. 2007. Fiber-modified adenovirus vectors decrease liver toxicity through reduced IL-6 production. J Immunol 178: 1767-1773.

Lebedeva, I V, Sarkar, D, Su, Z Z, Kitada, S, Dent, P, Stein, C A, Reed, J C, and Fisher, P B. 2003. Bcl-2 and Bcl-x(L) differentially protect human prostate cancer cells from induction of apoptosis by melanoma differentiation associated gene-7, mda-7/IL-24. Oncogene 22: 8758-8773.

Lebedeva, I V, Sauane, M, Gopalkrishnan, R V, Sarkar, D, Su, Zz, Gupta, P, Nemunaitis, J, Cunningham, C, Yacoub, A, Dent, P, and Fisher, P B. 2005. mda-7/IL-24: Exploiting cancer's Achilles' heel. Mol Therapy 11: 4-18.

Lebedeva, I V, Emdad, L, Su, Z Z, Gupta, P, Sauane, M, Sarkar, D, Staudt, M R, Liu, S J, Taher, M M, Xiao, R, Barral, P, Lee, S G, Wang, D, Vozhilla, N, Park, E S, Chatman, L, Boukerche, H, Ramesh, R, Inoue, S, Chada, S, Li, R, De Pass, A L, Mahasreshti, P J, Dmitriev, I P, Curiel, D T, Yacoub, A, Grant, S, Dent, P, Senzer, N, Nemunaitis, J J, and Fisher, P B. 2007. mda-7/IL-24, novel anticancer cytokine: focus on bystander antitumor, radiosensitization and antiangiogenic properties and overview of the phase I clinical experience (Review). Int J Oncol 31: 985-1007.

Lu, Q L, Liang, H D, Partridge, T, and Blomley, M J. 2003. Microbubble ultrasound improves the efficiency of gene transduction in skeletal muscle in vivo with reduced tissue damage. Gene Ther 10: 396-405.

Muruve, D A. 2004. The innate immune response to adenovirus vectors. Hum Gene Ther 15: 1157-1166.

Eager R, Harle L, Nemunaitis J. 2008. Ad-MDA-7; INGN 241: a review of preclinical and clinical experience. Expert Opin Biol Ther 8: 1633-1643.

Okegawa, T, Li, Y, Pong, R C, Bergelson, J M, Zhou, J, and Hsieh, J T. 2000. The dual impact of coxsackie and adenovirus receptor expression on human prostate cancer gene therapy. Cancer research 60: 5031-5036.

Pandha, H S, Stockwin, L H, Eaton, J, Clarke, I A, Dalgleish, A G, Todryk, S M, and Blair, G E. 2003. Coxsackie B and adenovirus receptor, integrin and major histocompatibility complex class I expression in human prostate cancer cell lines: implications for gene therapy strategies. Prostate Cancer Prostatic Dis 6: 6-11.

Park, M A, Hamed, H A, Mitchell, C, Cruickshanks, N, Dash, R, Allegood, J, Dmitriev, I P, Tye, G, Ogretmen, B, Spiegel, S, Yacoub, A, Grant, S, Curiel, D T, Fisher, P B, and Dent, P. 2011. A serotype 5/3 adenovirus expressing MDA-7/IL-24 infects renal carcinoma cells and promotes toxicity of agents that increase ROS and ceramide levels. Mol. Pharmacol 79: 368-380.

Sarkar, D, Su, Z Z, Lebedeva, I V, Sauane, M, Gopalkrishnan, R V, Dent, P, and Fisher, P B. 2002a. Mda-7 (IL-24): Signaling and functional roles. BioTechniques, Oct. Suppl., 30-39.

Sarkar, D, Su, Z Z, Lebedeva, I V, Sauane, M, Gopalkrishnan, R V, Valerie, K, Dent, P, and Fisher, P B. 2002b. mda-7 (IL-24) Mediates selective apoptosis in human melanoma cells by inducing the coordinated overexpression of the GADD family of genes by means of p38 MAPK. Proc Natl Acad Sci USA 99: 10054-10059.

Sarkar, D, Su, Z Z, Vozhilla, N, Park, E S, Gupta, P, and Fisher, P B. 2005a. Dual cancer-specific targeting strategy cures primary and distant breast carcinomas in nude mice. Proc Natl Acad Sci USA 102: 14034-14039.

Sarkar, D, Su, Z Z, Vozhilla, N, Park, E S, Randolph, A, Valerie, K, and Fisher, P B. 2005b. Targeted virus replication plus immunotherapy eradicates primary and distant pancreatic tumors in nude mice. Cancer research 65: 9056-9063.

Sarkar, D, Su, Z Z, and Fisher, P B. 2006. Unique conditionally replication competent bipartite adenoviruses-cancer terminator viruses (CTV): efficacious reagents for cancer gene therapy. Cell Cycle 5: 1531-1536.

Sarkar, D, Lebedeva, I V, Su, Z Z, Park, E S, Chatman, L, Vozhilla, N, Dent, P, Curiel, D T, and Fisher, P B. 2007. Eradication of therapy-resistant human prostate tumors using a cancer terminator virus. Cancer Res 67: 5434-5442.

Sarkar, D, Su, Z Z, Park, E S, Vozhilla, N, Dent, P, Curiel, D T, and Fisher, P B. 2008. A cancer terminator virus eradicates both primary and distant human melanomas. Cancer Gene Therapy 15: 293-302.

Sauane, M, Gopalkrishnan, R V, Sarkar, D, Su, Zz, Lebedeva, I V, Dent, P, Pestka, S, and Fisher, P B. 2003. Mda-7/IL-24: novel cancer growth suppressing and apoptosis inducing cytokine. Cytokine and Growth Factor Reviews 14: 35-51.

Sauane, M, Gupta, P, Lebedeva, I V, Su, Z Z, Sarkar, D, Randolph, A, Valerie, K, Gopalkrishnan, R V, and Fisher, P B. 2006. N-glycosylation of MDA-7/IL-24 is dispensable for tumor cell-specific apoptosis and "bystander" antitumor activity. Cancer Res 66: 11869-11877.

Sauane, M, Su, Z Z, Gupta, P, Lebedeva, I V, Dent, P, Sarkar, D, and Fisher, P B. 2008. Autocrine regulation of mda-7/IL-24 mediates cancer-specific apoptosis. Proc Natl Acad Sci USA 105: 9763-9768.

Schenk, E, Essand, M, Bangma, C H, Barber, C, Behr, J P, Briggs, S, Carlisle, R, Cheng, W S, Danielsson, A, Dautzenberg, I J, Dzojic, H, Erbacher, P, Fisher, K, Frazier, A, Georgopoulos, L J, Hoeben, R, Kochanek, S, Koppers-Lalic, D, Kraaij, R, Kreppel, F, Lindholm, L, Magnusson, M, Maitland, N, Neuberg, P, Nilsson, B, Ogris, M, Remy, J S, Scaife, M, Schooten, E, Seymour, L, Totterman, T, Uil, T G, Ulbrich, K, Veldhoven-Zweistra, J L, de Vrij, J, van Weerden, W, Wagner, E, and Willemsen, R. 2010. Clinical adenoviral gene therapy for prostate cancer. Hum Gene Ther 21: 807-813.

Siegel, R, DeSantis, C, Virgo, K, Stein, K, Mariotto, A, Smith, T, Cooper, D, Gansler, T, Lerro, C, Fedewa, S, Lin, C, Leach, C, Cannady, R S, Cho, H, Scoppa, S, Hachey, M, Kirch, R, Jemal, A, and Ward, E. 2012. Cancer treatment and survivorship statistics, CA Cancer J Clin 62: 220-241.

Sternberg, C N. 2002. Highlights of contemporary issues in the medical management of prostate cancer. Crit Rev Oncol Hematol 43: 105-121.

Su, Z Z, Shi, Y, and Fisher, P B. 1997. Subtraction hybridization identifies a transformation progression-associated gene PEG-3 with sequence homology to a growth arrest and DNA damage-inducible gene. Proc Natl Acad Sci USA 94: 9125-9130.

Su, Z Z, Goldstein, N I, Jiang, H, Wang, M N, Duigou, G J, Young, C S, and Fisher, P B. 1999. PEG-3, a nontransforming cancer progression gene, is a positive regulator of cancer aggressiveness and angiogenesis. Proc Natl Acad Sci USA 96: 15115-15120.

Su, Z, Shi, Y, and Fisher, P B. 2000. Cooperation between AP1 and PEA3 sites within the progression elevated gene-3 (PEG-3) promoter regulate basal and differential expression of PEG-3 during progression of the oncogenic phenotype in transformed rat embryo cells. Oncogene 19: 3411-3421.

Su, Z, Shi, Y, Friedman, R, Qiao, L, McKinstry, R, Hinman, D, Dent, P, and Fisher, P B. 2001a. PEA3 sites within the progression elevated gene-3 (PEG-3) promoter and mitogen-activated protein kinase contribute to differential PEG-3 expression in Ha-ras and v-raf oncogene transformed rat embryo cells. Nucleic Acids Res 29: 1661-1671.

Su, Zz, Lebedeva, I V, Gopalkrishnan, R V, Goldstein, N I, Stein, C A, Reed, J C, Dent, P, and Fisher, P B. 2001b. A combinatorial approach for selectively inducing programmed cell death in human pancreatic cancer cells. Proc Natl Acad Sci USA 98: 10332-10337.

Su, Z Z, Gopalkrishnan, R V, Narayan, G, Dent, P, and Fisher, P B. 2002. Progression elevated gene-3, PEG-3, induces genomic instability in rodent and human tumor cells. J Cell Physiol 192: 34-44.

Su, Z, Emdad, L, Sauane, M, Lebedeva, I V, Sarkar, D, Gupta, P, James, C D, Randolph, A, Valerie, K, Walter, M R, Dent, P, and Fisher, P B. 2005a. Unique aspects of mda-7/IL-24 antitumor bystander activity: establishing a role for secretion of MDA-7/IL-24 protein by normal cells. Oncogene 24: 7552-7566.

Su, Z Z, Sarkar, D, Emdad, L, Duigou, G J, Young, C S, Ware, J, Randolph, A, Valerie, K, and Fisher, P B. 2005. Targeting gene expression selectively in cancer cells by using the progression-elevated gene-3 promoter. Proc Natl Acad Sci USA 102: 1059-1064.

Wang, H, Li, Z, Yumul, R, Lara, S, Hemminki, A, Fender, P, and Lieber, A. 2011. Multimerization of adenovirus serotype 3 fiber knob domains is required for efficient binding of virus to desmoglein 2 and subsequent opening of epithelial junctions. J Virol 85: 6390-6402.

Tong A W, Nemunaitis J, Su D, Zhang Y, Cunningham C, Senzer N, Netto G, Rich D, Mhashilkar A, Parker K, Coffee K, Ramesh R, Ekmekcioglu S, Grimm E A, van Wart Hood J, Merritt J, and Chada S. 2005. Intratumoral injection of INGN 241, a nonreplicating adenovector expressing the melanoma-differentiation associated gene-7 (mda-7/IL24): biologic outcome in advanced cancer patients. Mol Ther 11: 160-172.

Wei, J, Kitada, S, Rega, M F, Stebbins, J L, Zhai, D, Cellitti, J, Yuan, H, Emdadi, A, Dahl, R, Zhang, Z, Yang, L, Reed, J C, and Pellecchia, M. 2009. Apogossypol derivatives as pan-active inhibitors of antiapoptotic B-cell lymphoma/leukemia-2 (Bcl-2) family proteins. J Med Chem 52: 4511-4523.

Wei, J, Stebbins, J L, Kitada, S, Dash, R, Placzek, W, Rega, M F, Wu, B, Cellitti, J, Zhai, D, Yang, L, Dahl, R, Fisher, P B, Reed, J C, and Pellecchia, M. 2010. BI-97C1, an optically pure Apogossypol derivative as pan-active inhibitor of antiapoptotic B-cell lymphoma/leukemia-2 (Bcl-2) family proteins. J Med Chem 53: 4166-4176.

Wolk, K, Kunz, S, Asadullah, K, and Sabat, R. 2002. Cutting edge: immune cells as sources and targets of the IL-10 family members?J Immunol 168: 5397-5402.

Example 2

Chemoprevention Gene Therapy (CGT) of Pancreatic Cancer Using Perillyl Alcohol and a Novel Chimeric Serotype Cancer Terminator Virus Abstract Conditionally replication competent adenoviruses (Ads) that selectively replicate in cancer cells and simultaneously express a therapeutic cytokine, such as melanoma differentiation associated gene-7/Interleukin-24 (mda-7/IL-24), a Cancer Terminator Virus (CTV-M7), hold potential for treating human cancers. To enhance the efficacy of the CTV-M7, we generated a chimeric Ad.5 and Ad.3 modified fiber bipartite CTV (Ad.5/3-CTV-M7) that can infect tumor cells in a Coxsackie Adenovirus receptor (CAR) independent manner, while retaining high infectivity in cancer cells containing high CAR. Although mda-7/IL-24 displays broad-spectrum anticancer properties, pancreatic ductal adenocarcinoma (PDAC) cells display an intrinsic resistance to mda-7/IL-24-mediated killing due to an mda-7/IL-24 mRNA translational block. However, using a chemoprevention gene therapy (CGT) approach with perillyl alcohol (POH) and a replication incompetent Ad to deliver mda-7/IL-24 (Ad.mda-7) there is enhanced conversion of mda-7/IL-24 mRNA into protein resulting in pancreatic cancer cell death in vitro and in vivo in nude mice containing human PDAC xenografts. This combination synergistically induces mda-7/IL-24-mediated cancer-specific apoptosis by inhibiting anti-apoptotic Bcl-xL and Bcl-2 protein expression and inducing an endoplasmic reticulum (ER) stress response through induction of BiP/GRP-78, which is most evident in chimeric-modified non-replicating Ad.5/3-mda-7- and Ad.5/3-CTV-M7-infected PDAC cells. Moreover, Ad.5/3-CTV-M7 in combination with POH sensitizes therapy-resistant MIA PaCa-2 cell lines over-expressing either Bcl-2 or Bcl-xL to mda-7/IL-24-mediated apoptosis. Ad.5/3-CTV-M7 plus POH also exerts a significant antitumor 'bystander' effect in vivo suppressing both primary and distant site tumor growth, confirming therapeutic utility of Ad.5/3-CTV-M7 plus POH in PDAC treatment, where all other current treatment strategies in clinical settings show minimal efficacy.

Introduction

Pancreatic cancer is the fourth most common cause of cancer deaths in the USA [1] and worldwide. This disease develops in an asymptomatic manner, and is usually advanced or metastatic in >80% cases at the time of diagnosis, making curative therapy impossible and leading to poor prognosis with incidence equaling mortality [1]. The plethora of molecular changes associated with progression of pancreatic cancer may facilitate its resistance to conventional chemotherapy and radiotherapy [2]. For this reason, it is imperative to develop rational molecular-targeted therapies that uniquely affect cancer cells irrespective of the precise genetic alterations promoting the cancerous state of these tumors. Obtaining this objective is particularly relevant in the context of pancreatic cancer.

In principle, conditionally replication competent Ads (CRCAs) should provide a viable approach for cancer therapy, which has already been approved by the FDA in China to treat diverse cancers [3]. In most currently used CRCAs, replication is dependent on a cells' p53 or pRb status, thereby limiting its universal applicability in cancer therapy. To create a more ubiquitous cancer-specific replicating CRCA, we engineered a CRCA manifesting the unique properties of tumor-specific E1A expression, thereby regulating virus replication, under the control of the minimal promoter of rat progression elevated gene-3 (PEG-Prom) [4, 5] with concomitant production of mda-7/IL-24, referred to as a Cancer Terminator Virus (CTV; Ad.PEG-E1A-mda-7; Ad.5-CTV-M7) [6, 7]. In addition to its cancer specific antitumor activity, mda-7/IL-24, an IL-10 gene family member secreted cytokine [8], can auto-regulate its own production [9] making it a suitable candidate for gene therapy with potential to eradicate not only primary infected tumor cells that receive mda-7/IL-24, but also distant tumor cells [10].

In the context of pancreatic cancer, decreased infectivity is a significant obstacle for successful gene therapy using an Ad serotype-5 (Ad.5) virus. The initial CTVs consisted of an Ad.5 expressing mda-7/IL-24 (Ad.5-CTV-M7) [6, 7] or interferon gamma (Ad.5-CTV-□) [11], with infectivity depending on Coxsackie-Adenovirus Receptors (CAR) on target cells. The number of cell surface CAR is frequently reduced in many tumor types, including pancreatic cancer [12], thereby limiting effective therapy. Using serotype chimerism, a novel CTV expressing mda-7/IL-24 (Ad.5/3-CTV-M7) was created by replacing the Ad.5 fiber knob with the Ad.3 fiber knob thereby facilitating infection in a CAR-independent manner [2, 13, 14]. An additional advantage of the Ad.5/3-CTV-M7 is its retention of high infectivity of cancer cells that contain high CAR. We previously compared Ad.5/3-mda-7 with Ad.5-mda-7 in low CAR PC-3 human prostate cancer cells, demonstrating higher efficiency in inhibiting cell viability in vitro [14]. Moreover, Ad.5/3-mda-7 potently suppressed in vivo tumor growth in a nude mouse xenograft model and in spontaneously induced prostate cancer that develops in Hi-myc transgenic mice [14]. Additional attributes of mda-7/IL-24 as a cancer gene therapeutic agent, include its ability as a secreted cytokine to kill cancer cells at distant sites in the body through "bystander" anticancer activity, which includes direct apoptosis-induction of cancer cells, robust anti-angiogenic activity, potent immune modulating properties and an ability to synergize with conventional therapies, including radiation, chemotherapy and antibody-based therapy [15-18]. Based on the noteworthy activity of Ad.5/3-mda-7 [8, 9, 19, 20] and the Ad.5-CTV-M7 [6, 7] as anticancer gene therapy agents, we anticipate that an Ad.5/3-CTV-M7 will provide even more vigorous and wide spectrum antitumor activity [21].

Initial Phase I studies with Ad.mda-7 (INGN 241) injected directly into tumors of patients with advanced carcinomas and melanomas, demonstrated safety and clinical activity in inducing cancer-specific apoptosis [22-26]. Unlike direct tumor administration of therapeutic viruses, systemic administration of viruses has generally proven disappointing and ineffective, particularly in the context of metastatic disease [27]. Two significant impediments to effective systemic use of therapeutic viruses are non-specific trapping of viruses in the liver or other non-tumor sites and neutralization and clearance of viruses by the immune system [28]. To circumvent these obstacles, we are employing an inventive novel stealth-delivery approach to deliver encapsulated Ads in microbubbles (MBs) (Ad/MB) coupled with ultrasound targeted MB destruction (ultrasound-targeted microbubble-destruction; UTMD) technology [2, 14, 29-31]. The effectiveness of the UTMD approach has been confirmed by administering Ad.5-CTV-M7 in MBs resulting in curing of primary-treated and distant-untreated human prostate cancer xenografts in nude mice [29] and by delivering Ad.5/3-mda-7 in MBs in the prostate region thereby decreasing prostate tumor volume and mass in Hi-myc transgenic mice [14, 31].

Although effective in a wide gamut of genetically diverse human cancers in vitro and in vivo, pancreatic cancer cells display an intrinsic resistance towards mda-7/IL-24-induced killing [15]. This resistance is manifested by a limited conversion of mda-7/IL-24 mRNA into protein in pancreatic cancer cells due to reduced association of this mRNA with polysomes [32]. We demonstrated that ROS inducers (such as arsenic trioxide and dithiophene) could relieve this 'translational block' and sensitize both mutant and wild type K-RAS pancreatic cancer cells to mda-7/IL-24-induced apoptosis, which could be abrogated by ROS inhibitors (N-acetyl-L-cysteine or Tiron) [2, 32, 33]. ROS generation by hypoxia [34, 35] or UV-B [36], as well as extracellular $H_2O_2$ [37], promotes phosphorylation of p70S6 Kinase and its downstream molecule 4EBP-1, thereby activating the mTOR signaling pathway. Based on these observations, and our previous findings [32, 38], we predicted that ROS generated by perillyl alcohol (POH) might promote the formation of pre-initiation complexes, resulting in the enhanced association of weakly-translated mda-7/IL-24 with polysomes, subsequently leading to more MDA-7/IL-24 protein. When POH was combined with a CTV producing mda-7/IL-24 (CTV-M7), which produces greater quantities of mda-7/IL-24 mRNA as compared to non-replicating Ad.mda-7, we anticipated a greater production of MDA-7/IL-24 protein and a more profound antitumor effect in pancreatic cancer cells. Moreover, we hypothesized that systemic delivery of a chimeric recombinant CTV producing mda-7/IL-24 (Ad.5/3-CTV-M7) by MB coupled with the UTMD approach combined with the chemoprevention non-toxic dietary agent POH might be beneficial in eliciting an enhanced antitumor response in pancreatic cancers in vivo, rather than using either agent alone or single agents with complementary mechanisms of action. We presently provide confirmation of this hypothesis and demonstrate profound therapeutic activity of the Ad.5/3-CTV-M7 with POH, CGT approach, for the therapy of human pancreatic cancers.

Material and Methods

Cell Lines and Generating Stable Clones

AsPC-1 and BxPC-3 cell lines were obtained from the ATCC, maintained in RPMI-1640 (GIBCO®, Invitrogen™, Auckland, NZ) supplemented with 10% Fetal Bovine Serum (FBS) (Sigma-Aldrich, St. Louis, Mo., USA). MIA PaCa-2 and PANC-1, also obtained from the ATCC, were maintained in DMEM (GiBCO®) supplemented with 10% FBS, and Immortalized normal pancreatic mesenchymal cell line, LT-2 were obtained from EMD Millipore (Billerica, Mass., USA) and hTERT immortalized human pancreatic nestin expressing cells (hTERT-HPNE; HPNE-1) were obtained from the ATCC and were maintained as instructed by the ATCC. All cell lines were cultured at 37° C. in a 5% $CO_2$ and 95% air-humidified incubator. To obtain Bcl-2 and Bcl-xL overexpressing clones, MIA PaCa-2 cells were transfected with pEGFP-C1/Bcl-2 (Addgene Plasmid 17999:GFP-Bcl-2) (Addgene, Cambridge, Mass., USA) or pSFFV-neo/Bcl-xL (Addgene Plasmid 8749: 3120 pSFFV-neo Bcl-xL), respectively. Individual clones were selected after ~3-4 weeks of continuous maintenance in culture medium containing 1 mg/ml G418 sulfate [39], and were further characterized for the presence/expression of the inserted plasmid by PCR and Western blotting.

Construction of Ad.5/3-PEG-E1A-Mda-7 (Ad-5/3-CTV-M7)

To construct Ad.5/3-PEG-E1A-mda-7, AdenoQuick cloning system (OD260, Inc., Boise, Id., USA) was employed. CMV-mda-7 along with $Kan^R$ (kanamycin resistance marker) was inserted into the E1 deleted region of pAd.5/3 (ΔE1) by homologous recombination between pAd5/3 (ΔE1) genomic plasmid with pE3.1 shuttle vector containing the mda-7/IL-24 expression cassette KanR, and Kanamycin selection strategy was used to select Ad.5/3-E3-E4-mda-7 and then pAd5/3.E3-E4-mda-7 was cut with Swa I to excise the $Kan^R$. The resultant pAd5/3.E3-mda-7 plasmid was recombined with the pE1.2 shuttle vector containing E1A-1B genes under control of PEG-3 promoter resulting in Ad5/3.PEG-E1A-1B-mda-7 genomic plasmid. This plasmid was digested with Pac I to release viral ITRs and was transfected into A549 cells to rescue the CRCA, Ad.5/3-PEG-E1A-E1B-mda-7 (Ad.5/3-PEG-E1A-mda-7; Ad.5/3-CTV-M7). Similar strategies were employed to make Ad.5/3-mda-7 and the Ad.5/3-PEG-E1A construct. The constructs were purified using CsCl gradient, titrated both by OD260-SDS (vp/ml) (Optical absorbance at 260 nm of lysed Ad using 0.1% Sodium dodecyl-sulphate solution) method and TCID50 (median or 50% tissue culture infective dose) or plaque forming methods (pfu/ml). We thank Drs. Curiel and Dmitriev (Washington University School of Medicine; St. Louis, Mo. USA for assistance in preparing and expanding various Ads.

Cell Viability Assays

Pancreatic cancer cell lines were infected with Ad in incomplete medium for 3 h followed by treatment with Perillyl alcohol (POH) (200 μM) in complete medium (10% FBS) for 72 h, and cell proliferation assays were performed at O.D. 560 nm using cell proliferation assays after adding 100 μl of 3-(4,5-dimethylthiazol-2-yl)-2,5-diphenyltetrazolium bromide (Sigma Aldrich) (MTT) dye (1 mg/ml) (Sigma-Aldrich).

Interaction Index or Combination Index

If agent 1 and agent 2 have 50% inhibitory effect, then it can be assumed that the combined effect of agent 1+agent 2 will be 0.5+0.5 {(1−0.5)}=0.75 (75%). In this case the fraction effect for a combination of two agents i.e., Fa(1,2) can be calculated from the single-agent effects, i.e., F1 and F2, denoted by Fa(1,2)=F1+F2(1−F1)(Webb equation or fractional product method)

For mutually non-exclusive events, and considering the dose-effect graph is hyperbolic or the slope of the graph is 1, at each combination dose, Interaction index or combination index (CI) of two agents at given dose is denoted simply by, $$CI = \frac{Fa(1, 2)}{Foa(1, 2)}$$

$< 1$ (Synergistic)
$CI = 1$ (Additive)
$< 1$ (Antagonistic)

where F1, F2 are the fraction effects obtained from agent 1 and 2, respectively, at a given dose when used as single agents alone. Fa(1,2) is mathematically calculated fraction effect of two agents when used in combination at a fixed given dose and Foa(1,2) is the fraction effect of two agents obtained experimentally at the fixed given dose [40, 41].

Apoptotic Assays

Apoptotic assays were performed using an FITC Annexin V Apoptosis Detection Kit I (BD Pharmingen™, San Diego, Calif., USA), according to the manufacturer's instructions. Flow cytometry assays were performed immediately after staining using FACS Canto (BD Bosciencese). Data were analyzed using FACSDIVA software.

ROS Measurements

To determine ROS production, cells were stained with 100 μl of 10 μM carboxy-H2DCFDA (Molecular Probes™, Invitrogen) in PBS for 30 min followed by treatment with Perillyl alcohol and fluorescence was measured with a Fluorometer using a green filter at the indicated time points.

Preparation of Whole-Cell Lysates and Western Blotting Analyses

Cells were treated for 48 h, lysed using cell lysis buffer (Cell Signaling Technology, Inc., Danvers, Mass., USA) supplemented with 1 mM PMSF (Sigma-Aldrich) with Protease cocktail inhibitor, Phosphatase inhibitor (Roche, Indianapolis, Ind. USA), and whole cell lysates were collected after centrifugation at 12000 rpm at 4° C. For Western blotting analyses, the primary antibodies used were mouse monoclonal anti-MDA-7/IL-24 (1:2000; Gen Hunter Corporation, Nashville, Tenn., USA), anti-E1A (1:1000; EMD Millipore) anti-EF1á (1:5000; EMD Millipore), rabbit monoclonal anti-Bcl-xL (1:1000), anti-PARP (1:1000), anti-Bcl-2 (1:1000; Cell Signaling Technology), rabbit polyclonal anti-BiP/GRP-78 (1:500; Santa Cruz Biotechnology, Inc., Santa Cruz, Calif., USA). The secondary antibodies used were polyclonal goat anti-mouse IgG (1:1000; Dako, Carpinteria, Calif., USA) and polyclonal swine anti-rabbit IgG (1:3000; Dako).

Detection of MDA-7/IL-24 Protein Using ELISA

MDA-7/IL-24 was quantified by using a human IL-24 DuoSet ELISA Development Kit from R&D Systems (R&D Systems, Inc., Minneapolis Mass., USA) according to the manufacturer's instructions. The capture antibodies used were monoclonal mouse anti-human IL-24 (R&D Systems), and detection antibodies used were biotinylated conjugated goat anti-human IL-24 (R&D Systems), which was finally quantified by Streptavidin-HRP after adding substrate solution ($H_2O_2$ and Tetramethylbenzidine). The cell culture supernatant or serum was collected at the indicated times and stored at −80° C. until used for quantification. The absorbance was read at 450 nm with background corrections set at 560 nm.

Preparation of Adenoviruses-Complexed with Microbbubles (MB) (MB/Ad)

Perflurocarbon Microbbubles (MBs) encapsulated by lipid monolayer and polyethylene glycol stabilizer were reconstituted in 1 ml of PBS containing $1 \times 10^{11}$ viral particles of indicated Ads, and unenclosed surface-associated Ads were treated with complement as previously described [42], and finally MB/Ad was dissolved in 1 ml of PBS prior to treatment.

In Vivo Xenograft Models

Athymic nude mice were injected s.c. in both flanks with $5 \times 10^6$ MIA PaCa-2/luc (a stable clone of MIA PaCa-2 cells containing integrated pGL-3/luc). The mice were injected by the i.p. route daily with vehicle or POH (75 mg/kg body weight) dissolved in tricaprylin. When tumors reached ~100 mm³ in size (~12-14 days), the animals were randomized into subgroups (n=6 animals per subgroup) and MB/Ad were administered. The mice received injections of 100 μl of MB/Ad through the tail vein once per week for a period of 4 weeks. Ultrasound (sonoporation) was performed with a SonoSite scanner (SonoSite) equipped with the transducer L25 set at 0.7 Mechanical Index, 1.8 MPa for 10 min in the left flank tumor of the of mice. Bioluminescence imaging (BLI) was done using a Xenogen In Vivo imaging system (IVIS) (Califer Life Sciences, Inc., Hopkinton, Mass.) after i.p. administration of D-luciferin (150 mg/kg body weight). Images were analyzed by Living Image software. At the end of the experiment, the mice were sacrificed and tumors were collected and preserved in neutral buffered formalin at 4° C. before embedding in paraffin for immunohistochemical analysis. The same tumor induction and treatment protocol was followed for in vivo studies in nude mice bearing MIA-PaCa-2/Bcl-xL (a stable clone of MIA PaCa-2 cells containing pSFFV-neo/Bcl-xL) xenograft model for demonstrating the efficacy of the CGT approach in therapy-resistant pancreatic cancers. A minimum of six animals were used per experimental group. Tumor volume (since these cells did not contain a luciferase gene) was calculated using the formula: $\pi/6 \times larger\ diameter \times (smaller\ diameter)^2$. At the end of the experiment, the animals were sacrificed, and the tumors were removed and weighed. The VCU Institutional Animal Care and Use Committee approved the experimental protocols used in this study and the animals were cared for in accordance with institutional guidelines.

Statistical Analyses

Statistical analyses were performed using GraphPad Prism 5.0 (GraphPad Software, Inc.). Student's t-test or 1-way ANOVA was used as indicated, to study the level of significance ($P<0.05$).

Results

Figure 6A:
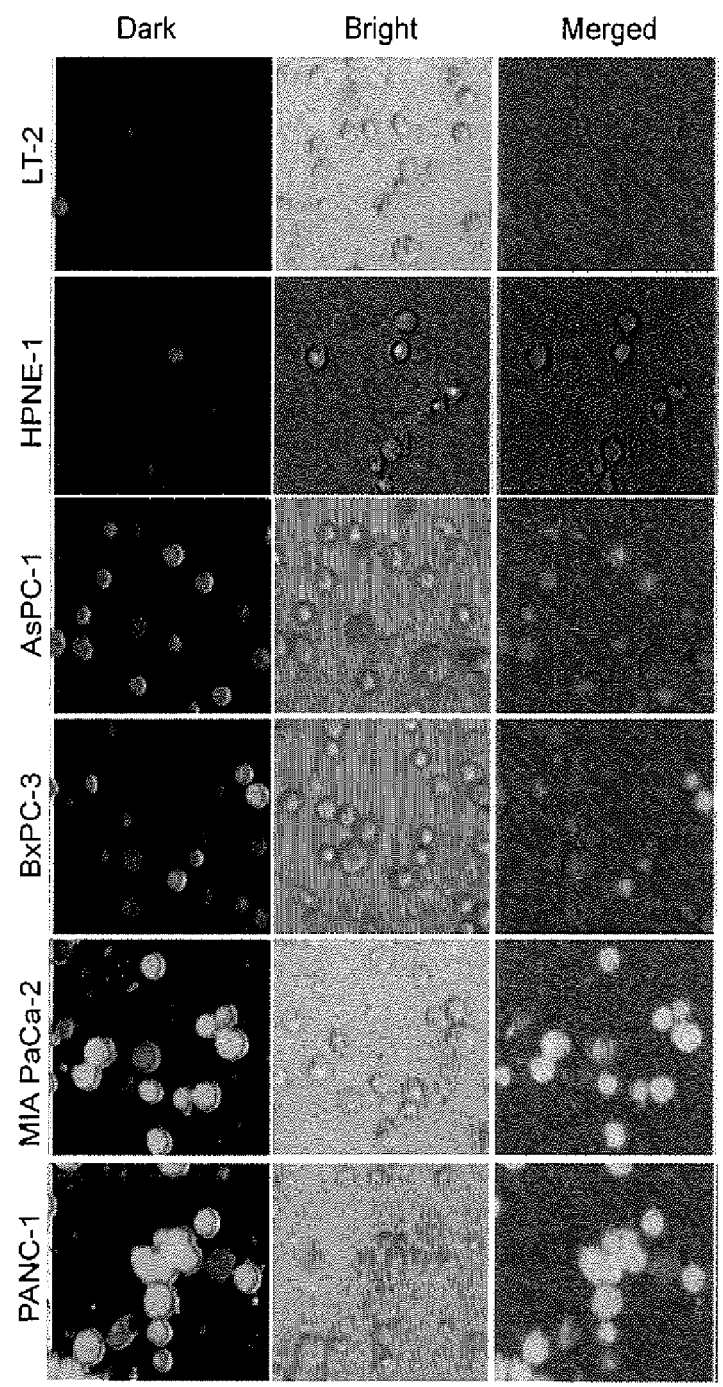
Figure 6B:
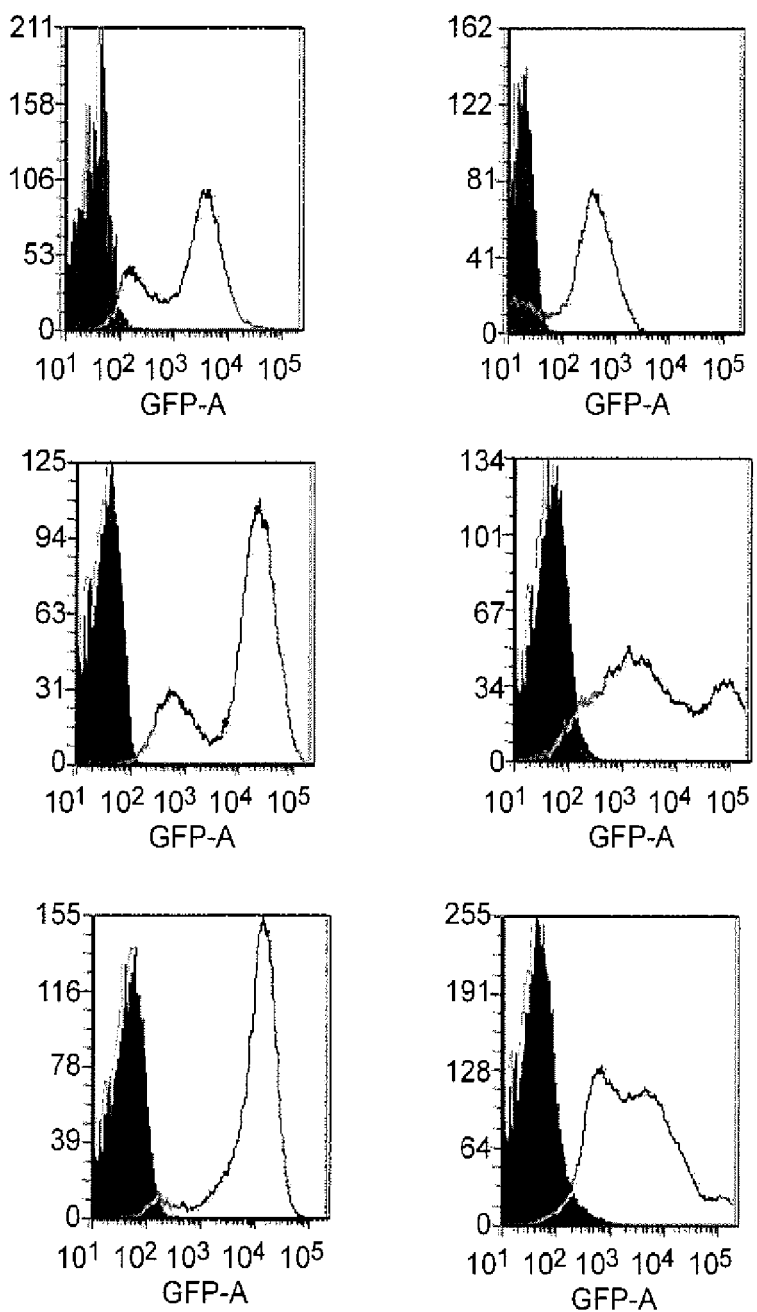
Figure 6C:
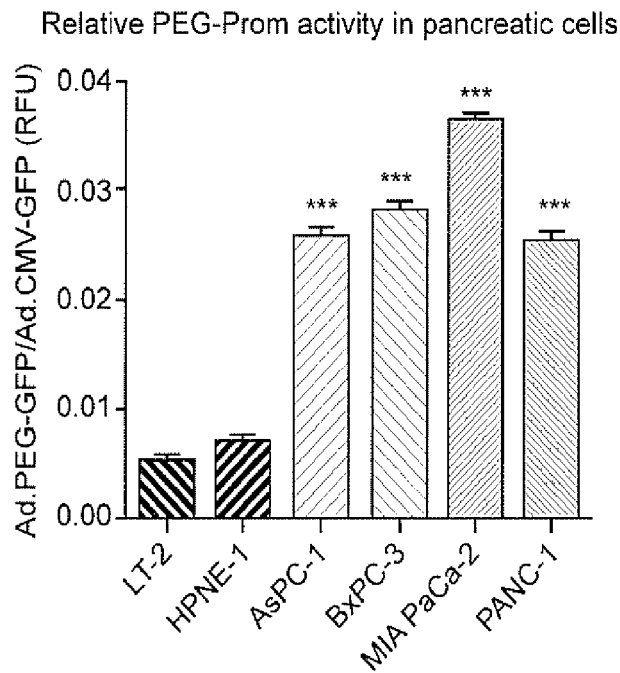
Figure 6D:
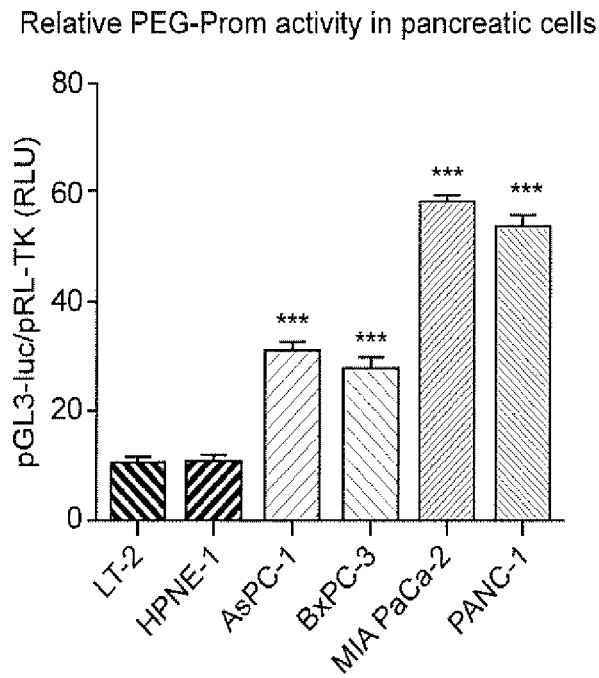

PEG-Prom is Selectively Expressed at Elevated Levels in Pancreatic Cancer Cells Vs. Normal Immortal Pancreatic Cells The PEG-Prom, isolated from the PEG-3 gene [4, 5] displays selective cancer-specific activity in a broad spectrum of cancers vs. normal counterparts, including tumors of the prostate, breast, brain, colon, pancreas and melanoma [4, 6, 7, 11, 13, 31]. To confirm differential expression of the PEG-Prom in multiple pancreatic cancer cells lines, mutant K-ras pancreatic cancer cells, AsPC-1, PANC-1 and MIA PaCa-2 and a wild type K-ras pancreatic cancer cell, BxPC-3, and immortal normal pancreatic cells, LT-2 and HPNE-1, were infected with replication-incompetent Ads expressing GFP or Luc under control of the PEG-Prom or CMV-Prom [4]. Cells were infected with 5000 vp/cell and were examined 2-days post infection. Ad.5-PEG-GFP activity was higher in pancreatic cancer cell lines vs. normal pancreatic cells as confirmed by immunofluorescence (FIG. 6A) and flow-cytometric (FIG. 6B) analyses. Although MIA PaCa-2 expresses lower levels of CAR (unpublished data), it showed high expression of Ad-PEG-GFP, since it expresses elevated levels of AP-1, c-Jun [11]. The combination of AP-1 and PEA-3 transcription factors is responsible for enhanced expression of the PEG-Prom in diverse cancers vs. normal cellular counterparts [4]. In order to minimize any differential effects due to CAR-dependent entry of Ad-5.GFP, we also infected parallel cultures with Ad.5-CMV-GFP, and normalized the value of Ad.5-PEG-GFP/Ad.5-CMV-GFP (FIG. 6C). As predicted, GFP expression driven by the PEG-Prom displayed differential elevated expression in the four pancreatic cancer cell lines. The PEG-Prom activity of the PDAC cell lines MIA PaCa-2, PANC-1, AsPC-1 and BxPC-3 was significantly higher as compared to normal immortal pancreas counterparts, LT-2 and HPNE-1. To provide further confirmation of PEG-Prom specificity and to avoid the dependence on receptors, especially CAR, for Ad entry, we also transfected the pancreatic cancer cell lines with pPEG-luc and pRL-TK (20:1), and found that PEG-Prom activity was again significantly elevated in the PDAC cell lines as compared to LT-2 and HPNE-1 cells (FIG. 6D).

Chimeric Modified Ad.5/3-CTV-M7 Potentiates the Activity of Mda-7/IL-24 and Acts Synergistically with POH in Reducing Pancreatic Tumor Cell Viability To test the hypothesis that bipartite CRCAs will cause oncolysis and reduce cell viability in PDAC as compared to normal pancreatic cell lines, we engineered and employed a series of CRCAs with an Ad.5 backbone (Ad.5-PEG-E1A, Ad.5-CTV-M7) as well as an Ad.5/3 backbone (Ad.5/3-mda-7, Ad.5/3-PEG-E1A and Ad.5/3-CTV-M7) in which the replication of Ad is controlled by the PEG-Prom. Pancreatic cancer cells treated with a replication incompetent Ad.5-mda-7 or Ad.5/3-mda-7 showed almost no effect at an m.o.i. of 1000 vp/cell in all cell lines tested, whereas a minor effect was observed at a higher m.o.i. of 10000 vp/cell in the case of Ad.5/3-mda-7 after 3-days post-infection. With the Cancer Terminator Virus (CTV-M7) cell viability was reduced dramatically even at lower m.o.i. The $IC_{50}$ of PDAC cell lines treated with Ad.5-CTV-M7 was found to be ~100 vp/cell in all cell lines tested with minimal effect in the LT-2 cell line even at 10000 vp/cell of Ad.5-CTV-M7 (FIG. 13A-D). PDAC cell killing was most dramatic when cells were treated with Ad.5/3-CTV-M7 ($IC_{50}$~50 vp/cell).

Pancreatic cancer cells, containing either a wild type or mutant K-RAS gene, display inherent resistance towards mda-7/IL-24-induced apoptosis [32], which can be reversed with addition of the chemoprevention agent POH [38]. POH has been used to treat various solid malignancies and is currently undergoing evaluation in phase II clinical trials [2]. POH is very unstable and cannot be detected in plasma and the major metabolites of POH are Perillic acid and Dihydroperillic acid which have an ~1-3 h half-life. The products are not accumulated over time even when POH is administered at a dose of 800-1600 mg/m$^2$/dose [43-45], which produce minimal side effects. Based on previous studies, 500 μM of Perillic acid in plasma was associated with minimal toxicities [43, 44]. Considering the toxicity profile, we choose a sub-lethal dose of 200 μM of POH, which is clinically achievable, to evaluate the efficacy of this chemoprevention dietary agent in potentially treating PDAC. Although 200 μM of POH is not lethal and does not affect proliferation of PDAC cell lines, this dose is sufficient to induce significant amounts of ROS in a temporal manner in both wild type and mutant K-ras pancreatic cell lines (FIG. 14). In previous studies [32], we did not notice appreciable formation of ROS after 24 h treatment with 200 μM POH, even though this treatment promoted translation of the MDA-7/IL-24 protein and this effect was inhibited by addition of ROS inhibitors. Since we observed an increase in ROS with treatment with 200 μM of POH at 6 h treatment, we performed a time course study, which indicated elevated levels of ROS between 1 and 12 h, with maximum levels at 6 h and baseline levels of ROS at 24 h in PDAC cells following POH treatment (FIG. 14). This temporal relationship in ROS induction may explain the differences in detection of ROS in the present study as opposed to an earlier study monitoring levels at 24 h [32]. It is also possible that the early window of induction by POH is sufficient when enough mda-7/IL-24 mRNA is available to facilitate translation into MDA-7/IL-24 protein and death in pancreatic cancer cells. In this context, the transient increase in ROS by POH would be predicted to be more effective in producing MDA-7/IL-24 protein when infected with the CTV-M7, which results in high levels of mda-7/IL-24 mRNA.

To investigate the potential combinatorial effect of our chemoprevention gene therapy (CGT) approach, both wild type K-ras (BxPC-3) and mutant K-ras (MIA PaCa-2) cells were infected with a replication incompetent Ad.5-mda-7 or Ad.5/3-mda-7 (1-10000 vp/cell), or a CRCA either Ad.5-CTV-M7 or Ad.5/3-CTV-M7, for 3 h followed by treatment with 200 μM POH, and cell proliferation/viability was monitored 72 h post-infection. Combinatorial treatment with a replication incompetent Ad or CRCA carrying mda-7/IL-24 with POH resulted in a leftward shift of the dose response curve in both cell lines indicating a synergistic effect of this combination (FIGS. 7A and 7B). Additionally, we mathematically calculated the effect of POH in combination with Ad.5-CTV-M7 and Ad.5/3-CTV-M7. We found that there was a synergistic effect in both the BxPC-3 and MIA-PaCa-2 cell lines (FIGS. 15A-D).

Figure 9A:
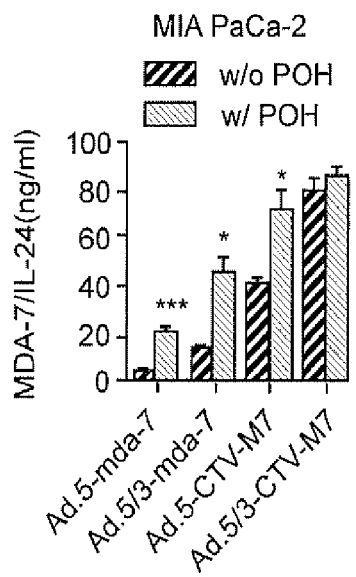
Figure 9B:
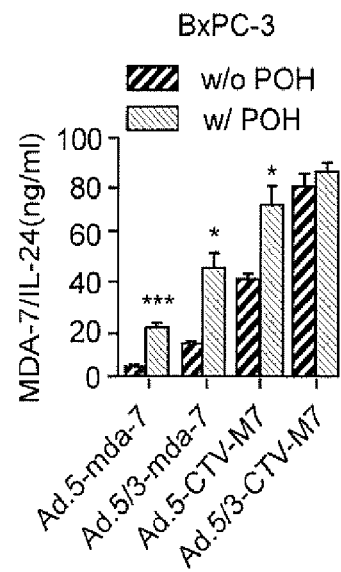
Figure 9C:
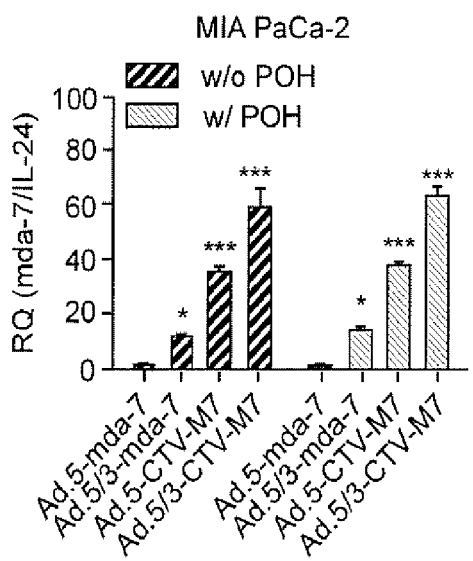
Figure 9D:
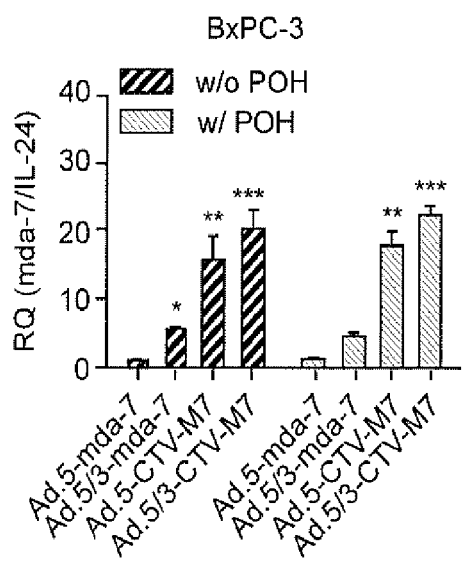
Figure 9E:
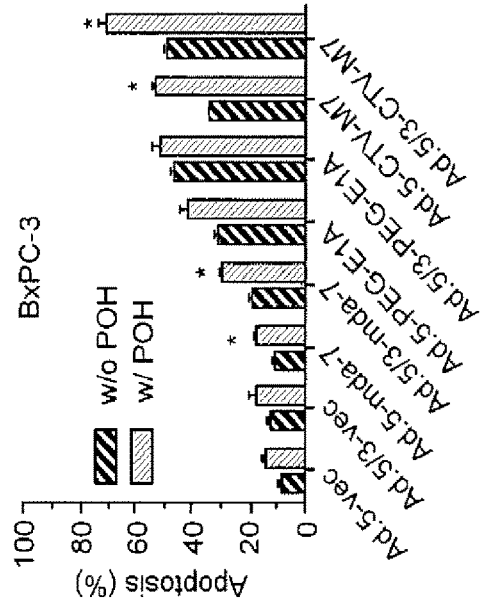
Figure 9F:
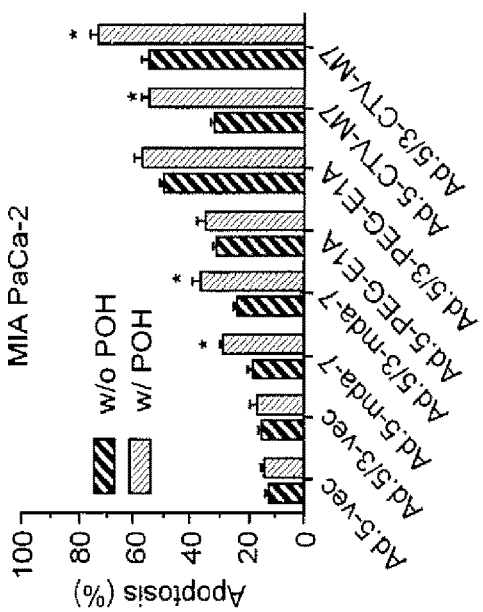

Combinatorial Treatment with Ad Producing Mda-7/IL-24 and POH Induces Apoptosis Induction and MDA-7/IL-24 Protein Production in PDAC Cell Lines We next focused on defining the mechanism underlying reduced cell growth/viability and apoptosis induction in PDAC cells treated with replication incompetent Ads (2500 vp/cell) or CRCAs (CTVs) (250 vp/cell) followed by POH treatment. Infection with Ads expressing mda-7/IL-24 and treatment with POH significantly increased MDA-7/IL-24 protein expression, which correlated with its apoptotic activities as reflected by PARP cleavage (FIG. 8). The cancer-specific replication of CRCAs, as confirmed by E1A expression (FIG. 8), lead to elevated levels of mda-7/IL-24 mRNA (FIGS. 9A, 9B, 9C and 9D) that might be responsible for increased MDA-7/IL-24 protein expression in CTV-M7 as compared to MDA-7/IL-24 protein expression resulting from replication incompetent Ads. By using 1 way-ANOVA, it was found that there were highly significant differences in mRNA expression in Ad.5-CTV-M7 and Ad.5/3-CTV-M7 infected as compared to Ad.5-mda-7 infected PDAC cells (FIGS. 9C and 9D). Moreover, Ad replication leads to ROS [46], which might facilitate MDA-7/IL-24 production following infection with CTV-M7.

There was a decrease in Bcl-2 and Bcl-xL expression in MIA PaCa-2 and BxPC-3 cells following infection with Ad.5-CTV-M7 and Ad.5/3-CTV-M7, which decreased even further following combination therapy with POH (FIG. 8). No noticeable change was observed in either PDAC cell line infected with Ad.5-mda-7 or Ad.5/3-mda-7 alone, but the change in Bcl-2 and Bcl-xL following CGT treatment correlated with intracellular as well as extracellular/secreted MDA-7/IL-24 expression (FIGS. 8, 9A and 9B). MDA-7/IL-24 has Hsp-90-like chaperone (BiP/GRP-78) binding sites present in the C and F helices, and mutations in these binding sites prevents mda-7/IL-24 from executing its apoptotic functions [47] in cancer cells. Binding of MDA-7/IL-24 to BiP/GRP-78 results in localization in the endoplasmic reticulum (ER) [32]. Since the ER is the principal site of MDA-7/IL-24 localization and its subsequent folding; the increase in MDA-7/IL-24 expression can lead to an unfolded protein (UPR) response that results in increased production of chaperone binding proteins BiP/GRP-78, GRP-94 and its downstream targets p38-MAPK and GADD that concludes in apoptosis in carcinomas of the breast, lung, prostate and melanoma [9, 20, 47-49]. Ad.5-CTV-M7 and Ad.5/3-CTV-M7 infection of wild type and mutant K-ras PDAC cell lines increase expression of BiP/GRP-78, which was further increased following treatment with POH as compared to untreated control Ad.5-vec and Ad.5/3-vec infected cells. Although there was minimal or no expression of BiP/GRP-78 in Ad.5-mda-7 or Ad.5/3-mda-7 infected cells, expression was increased dramatically following combination treatment, which coincided with the increased expression of MDA-7/IL-24 that culminated in apoptosis, as reflected by PARP cleavage and Annexin V/PI staining (FIGS. 8 and 9A-F).

CTV-M7 Eradicates Therapy-Resistant Bcl-2 and Bcl-xL Overexpressing PDAC Cells

Figure 10A:
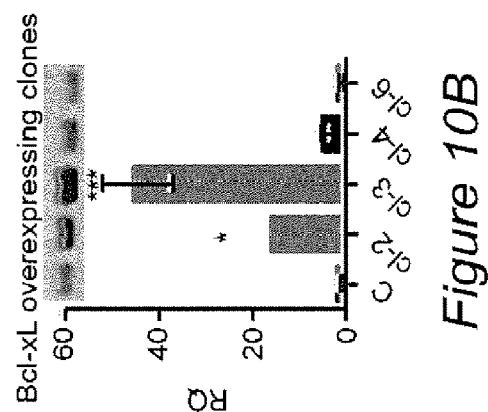
Figure 10B:
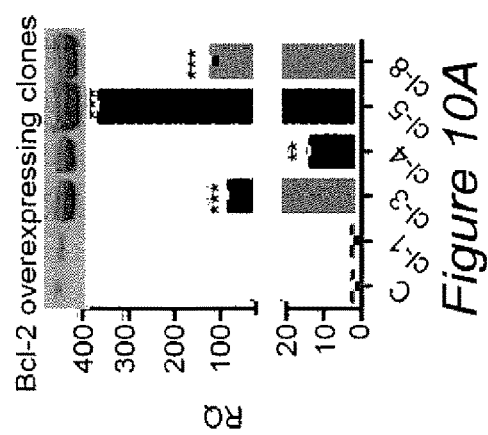

The antiapoptotic Bcl-2 family plays an important role in the development of therapy resistant pancreatic cancers [50]. Although Bcl-2 plays a significant function in various cancers, it may not contribute to progression of pancreatic cancers, since expression decreases with PDAC progression and lymph node metastasis [51]. In contrast, Bcl-xL appears to be a key contributor to PDAC progression [52] and chemoresistance [50, 53]. Thapsigargin inhibits ER residing $Ca^{+2}$-ATPase functions, and thus induces ER stress-mediated apoptosis [54]. Downregulation of Bcl-xL sensitizes (3-islet cells to Thapsigargin-induced ER-mediated apoptosis [54], whereas overexpression of Bcl-xL protects cells from ER-mediated apoptosis [55, 56]. Bcl-2 and Bcl-xL also protect prostate carcinoma cells from mda-7/IL-24-mediated induction of growth suppression and apoptosis [14, 39]. ER-stress plays an important role in mda-7/IL-24-mediated apoptosis in pancreatic cancers (FIGS. 8 and 9). Moreover, Bcl-xL is markedly downregulated by mda-7/IL-24 plus POH in PDAC cells. Thus, it is anticipated that overexpression of Bcl-xL might play a pivotal role in developing intrinsic resistance towards Ad.5/3-mda-7-mediated therapy, however, in the presence of Ad.5-CTV-M7 or Ad.5/3-CTV-M7 and POH, robust expression of MDA-7/IL-24 may lead to increased and sustained ER stress culminating in PDAC cell death. To experimentally test this possibility, we established stable Bcl-2 and Bcl-xL overexpressing MIA PaCa-2 clones (FIGS. 10A and 10B).

Figure 10C:
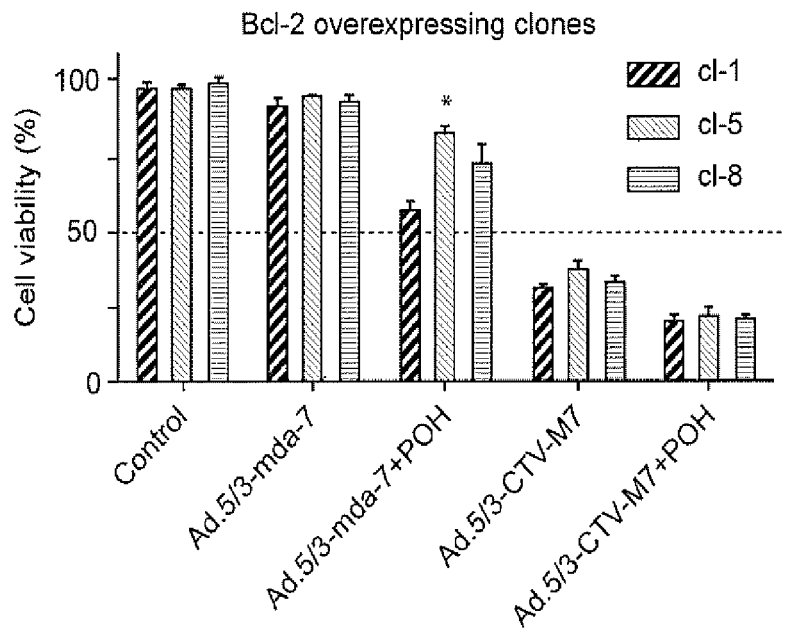
Figure 10D:
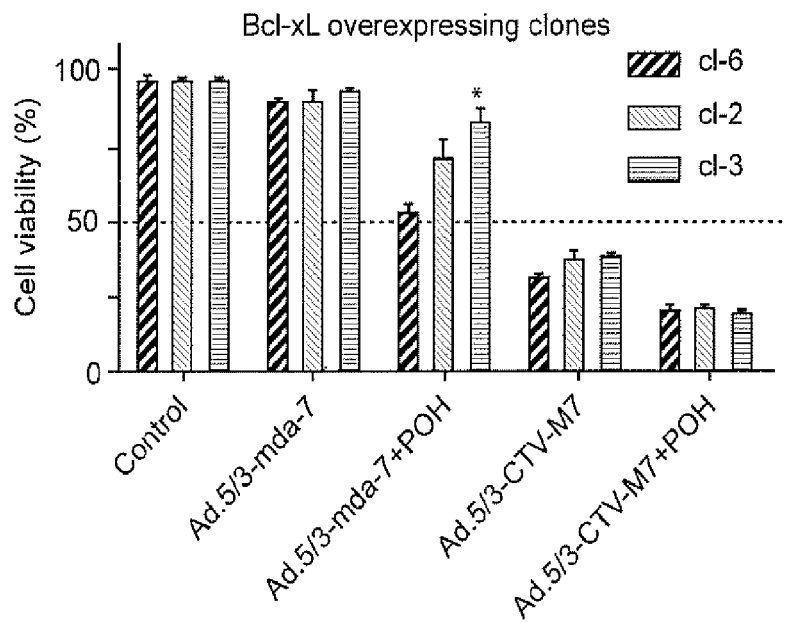
Figure 10E:
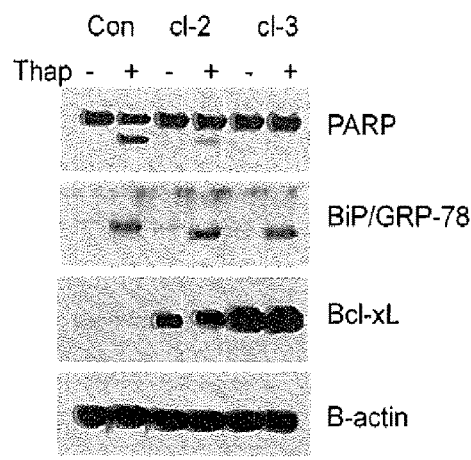
Figure 10F:
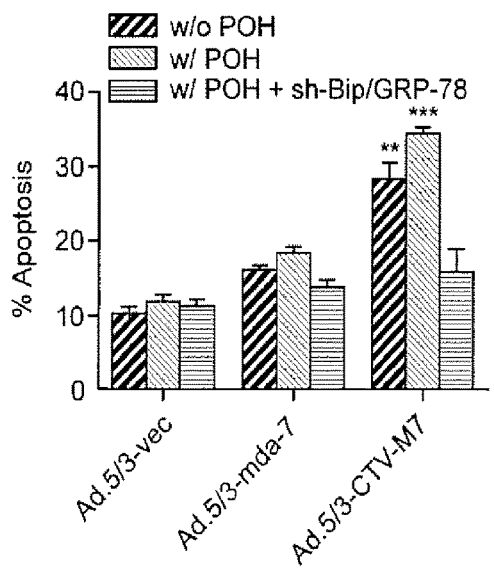
Figure 10G:
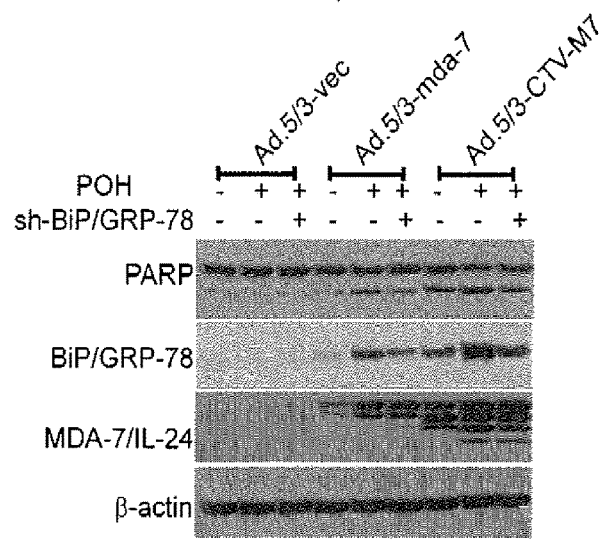

Infection with Ad.5/3-mda-7 did not significantly inhibit cell viability in Bcl-2 and Bcl-xL overexpressing MIA PaCa-2 clones, whereas simultaneous treatment with POH resulted in decreased viability, which inversely correlated with the level of Bcl-2 and Bcl-xL (FIGS. 10C and 10D). When Bcl-2 and Bcl-xL overexpressing clones of MIA PaCa-2 were infected with Ad.5/3-CTV-M7 and treated with POH, there was a significant decrease in viability, which was similar in parental and Bcl-2 or Bcl-xL overexpressing clones. These results support the utility of CTV-M7 in treating therapy-resistant PDAC that is mediated by overexpression of Bcl-2 or Bcl-xL (FIGS. 10C and 10D). Additionally, Bcl-xL overexpressing MIA PaCa-2 clones displayed partial resistance towards Thapsigargin-induced ER stress-mediated apoptosis as indicated by decreased PARP cleavage (FIG. 10E). Although Thapsiagargin induced similar levels of BiP/GRP-78 in parental control MIA PaCa-2, modestly Bcl-xL overexpressing MIA Paca-2 cl-2 and high Bcl-xL overexpressing MIA PaCa-2 cl-3, PARP cleavage inversely correlated with the levels of Bcl-xL (FIG. 10E). These results indicate that overexpression of Bcl-xL can override the increase in BiP/GRP-78 produced by treatment with Thapsigargin that leads to extensive PARP cleavage in PDAC cells. Inhibiting BiP/GRP-78 using sh-BiP/GRP-78 reduced apoptosis in MIA PaCa-2 Bcl-xL cl-3 cells (high expresser) treated with Ad.5/3-CTV-M7 plus POH (FIG. 10F) without inhibiting production of MDA-7/IL-24 (FIG. 10G). Since robust expression of MDA-7/IL-24 by Ad.5/3-CTV in the presence of POH leads to profound expression of BiP/GRP-78, induction of persistent ER stress may result in a switch from pro-survival to pro-apoptotic signaling events [57](FIGS. 10F and 10G). Reduced expression of BiP/GRP-78 correlated with decreased sensitivity to MDA-7/IL-24-mediated apoptosis (FIGS. 10F and 10G), reinforcing a role for sustained ER stress as a mediator of cell death in therapy resistant cells, which could provide an alternative approach to overcome therapy resistance in cancers.

Chimeric Modified CTV-M7 (Ad.5/3-CTV-M7) Eradicates Tumors in Mice Bearing Human PDAC Xenografts A major impediment in cancer gene therapy is the lack of efficient non-toxic systemic gene delivery systems. Ad and Ad-associated gene therapies have been used efficiently for many years to deliver genes [58] and can be manipulated to replicate specifically in cancer cells with robust expression of therapeutic genes [7, 11, 29, 38]. A major obstacle to Ad gene therapy is to provide a means of shielding the therapeutic Ad (i.e., Ad.mda-7 or CTV-M7) from destruction by the immune system and non-specific trapping and clearance in the liver or other organ sites not harboring neoplastic cells [28, 59]. To overcome this problem, we developed an innovative stealth delivery approach in which therapeutic Ads are conjugated with MBs (Ad/MB) and treated with complement prior to injection into the tail vein, which shields the Ads in the circulation from trapping in the liver [29] and elimination by the immune system [28, 30, 59]. To further support the role of MBs in 'stealth delivery' of Ads, we confirmed that Ads conjugated with MBs treated with complement did not elicit an innate immune response (i.e., activation of IL-6, TNF-α and IFN-γ) following intravenous tail vein injection into an immune-competent C57B6 mice [30]. In contrast, Ads alone or MB-encapsulated Ads without complement treatment were immunogenic [30]. Moreover, complement-treated MBs containing a therapeutic tropism-modified Ad (Ad.5/3-mda-7) coupled with UTMD approach effectively delivered virus in the tumor region of the prostate in immune-competent transgenic Hi-myc mice resulting in an inhibition in tumor development [14].

Figure 11A:
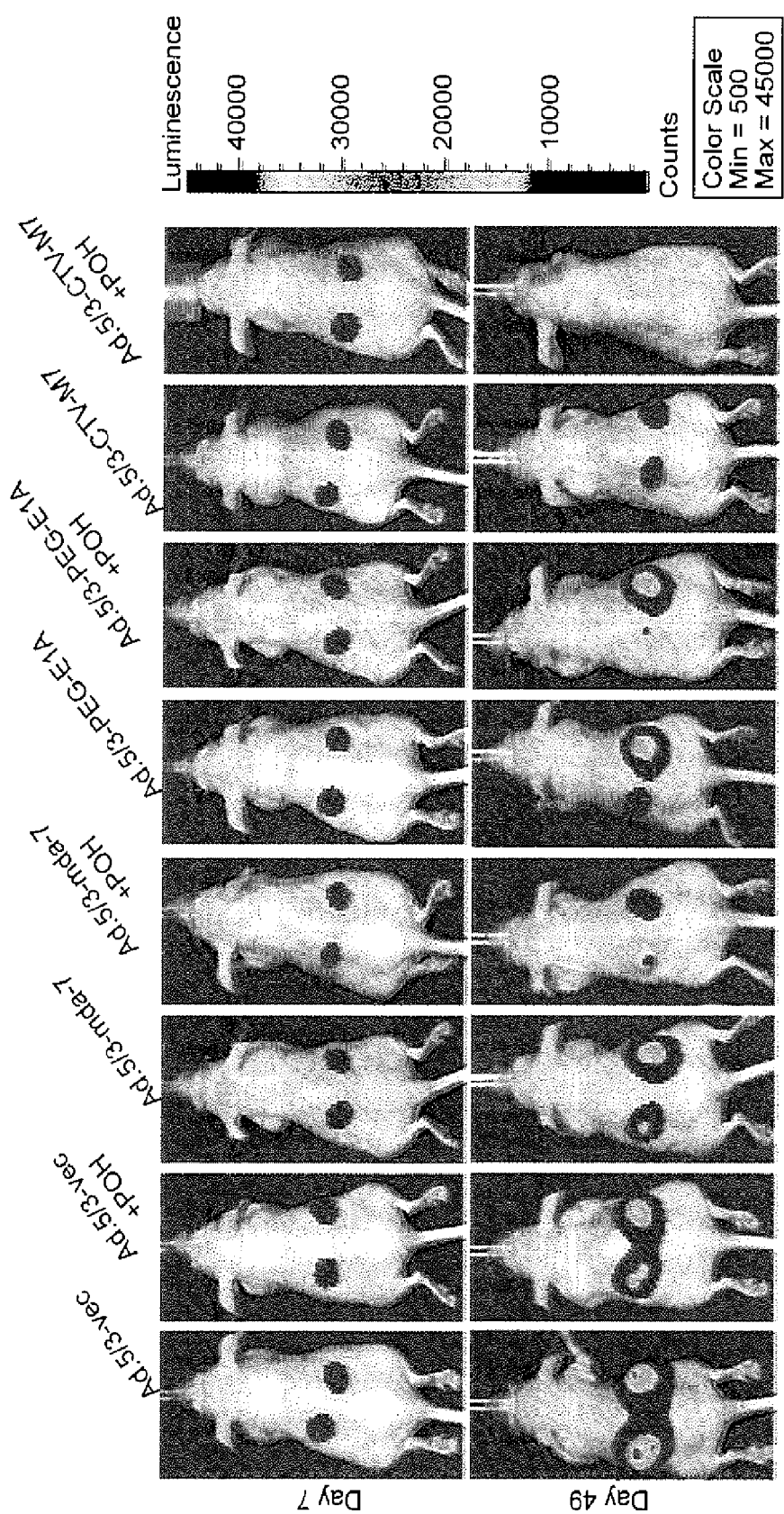
Figure 11B:
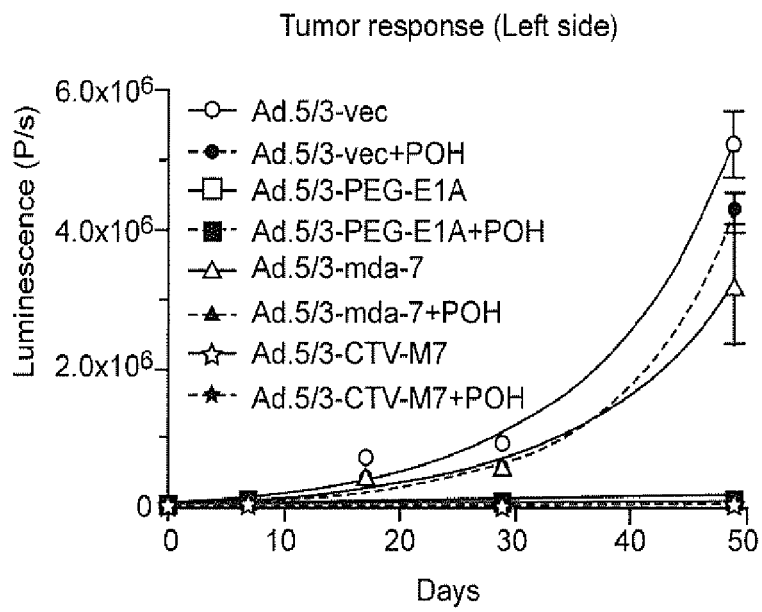
Figure 11C:
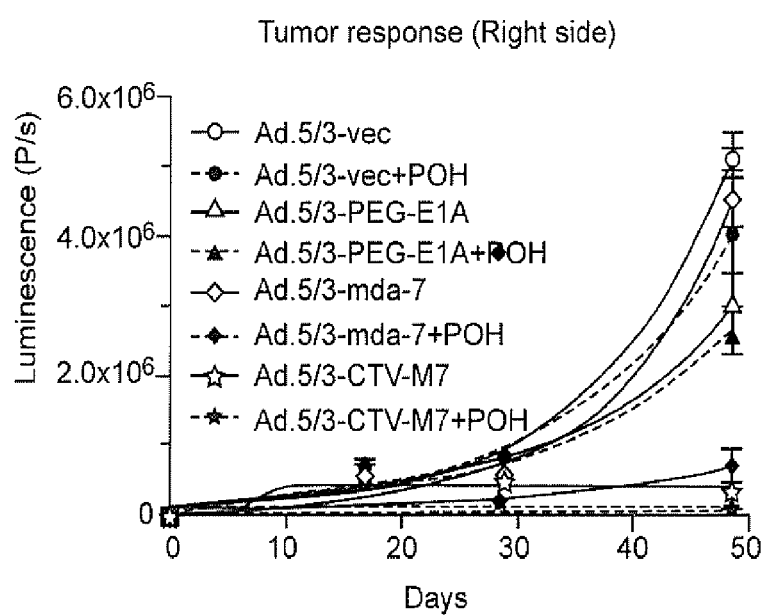

As a proof-of-principle for site-specific systemic delivery of therapeutic Ads, nude mice were injected in each flank with $5\times10^6$ MIA PaCa-2/luc or MIA PaCa-2/Bcl-xL cells. Tumor-bearing MIA PaCa-2/luc or MIA PaCa-2/Bcl-xL nude mice (n=6 in each group) were then injected in their tail vein with 100 µl of complement treated Ad/MB (Ad.5/3-vec/MB, Ad.5/3-mda-7/MB, Ad.5/3-PEG-E1A/MB, Ad.5/3-CTV-M7/MB) ~12 to 14 days post cell-implantation. Following tail vein administration of Ad/MB, a portable SonoSite Micro-Maxx US platform equipped with an L25 linear array transducer set at 0.7 Mechanical Index, 1.8 MPa for 10 min was used to sonoporate the tumor implanted on the left flank. Mice were injected with Ad/MB once a week for 4 wks for a total of four treatments, and POH was i.p. administered daily from the first day until the $6^{th}$ week. Some mice were killed 1 day after the last treatment with Ad (i.e., $4^{th}$ week of Ad treatment) to determine the level of secreted MDA-7/IL-24 protein in the serum and its potential contributing role as an anti-tumor agent. Bioluminescene imaging (BLI) was used to quantify tumor size after i.p. administration of 150 mg/kg D-luciferin. There was a positive correlation (r=0.92) of Luminescence intensity vs. cell number (FIG. 16), indicating the utility of BLI in determining tumor size non-invasively. There was a significant decrease in tumor sizes in both the left and right flanks of mice treated with Ad.5/3-CTV-7/MB plus POH as compared to vector infected control (Ad.5/3-vec plus POH) after two weeks of treatment with gene therapy (FIG. 17), and there was no detectable tumor at the end of the experiment (FIGS. 11A-E and FIG. 17). This may reflect the ability of MDA-7/IL-24 to promote a 'bystander' antitumor effect causing a reduction in the growth of the distant tumor not treated with Ad/MB. There was no significant change in dose response curve of MIA PaCa-2/luc cells treated with Ad.5-vec+POH as compared to vehicle Ad.5/3-vec indicating that the dose used for POH is a non-toxic but therapeutically inactive. Although we found a significant difference in tumor size on the left sided tumor treated with Ad.5/3-PEG-E1A, no significant change in tumor size was observed in right-flank tumor compared to right-flank tumor of the vehicle-treated group (FIGS. 11B, and 11C).

Figure 11D:
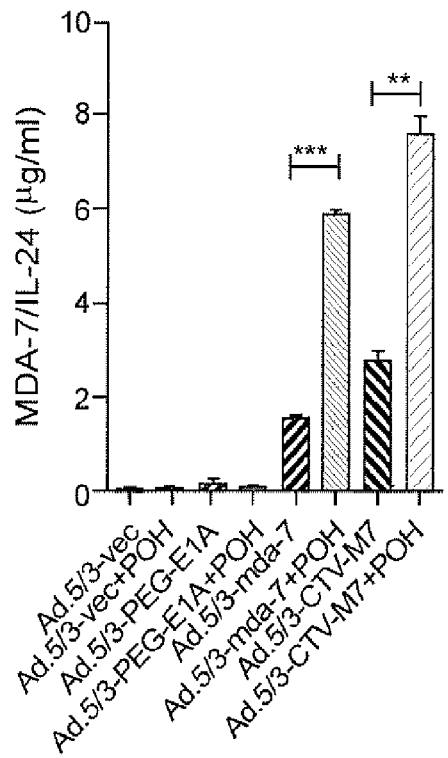
Figure 11E:
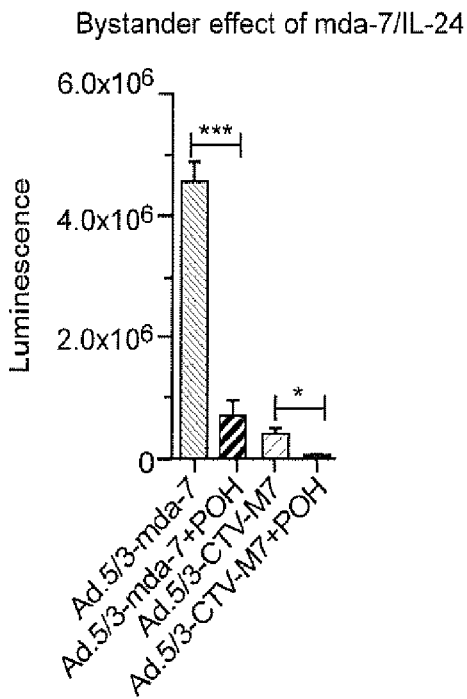

Using ELISA we observed a higher level of MDA-7/IL-24 in blood plasma of animals receiving Ad.5/3-mda-7/MB and Ad.5/3-CTV-M7/MB plus POH as compared to Ad.5/3-mda-7/MB and Ad.5/3-CTV-M7/MB, respectively, without POH treatment (FIG. 11D). In the context of Ad.5/3-mda-7 plus POH, this effect on the distal tumor can be attributed directly to secreted MDA-7/IL-24 and 'bystander' antitumor activity in the non-treated right-sided tumor (FIG. 11E). Since the level of MDA-7/IL-24 protein in the serum of animals treated with Ad.5/3-CTV-M7/MB plus POH is elevated in comparison with Ad.5/3-mda-7/MB plus POH, the enhanced effect observed on the distant tumor may involve 'bystander' antitumor activity caused by secreted MDA-7/IL-24 as well as potential secondary viral infection of released Ad.5/3-CTV-M7. In contrast, although there was almost complete eradication of tumors in the left flank of mice treated with Ad.5/3.PEG-E1A alone and with POH, there was a minimal change in the right-flank tumors (FIGS. 11A, 11B and 11C). This observation further validates the superior efficacy of CRCAs armed with a therapeutic cytokine gene (mda-7/IL-24), such as the novel Ad.5/3-CTV-M7, that can produce MDA-7/IL-24 which directly kills tumor cells and also affects tumors at distant sites by virtue of 'bystander' anti-tumors effects, which can eradicate distant PDAC tumors in the opposite flank when animals are treated with POH, i.e., the CGT approach.

Figure 12A:
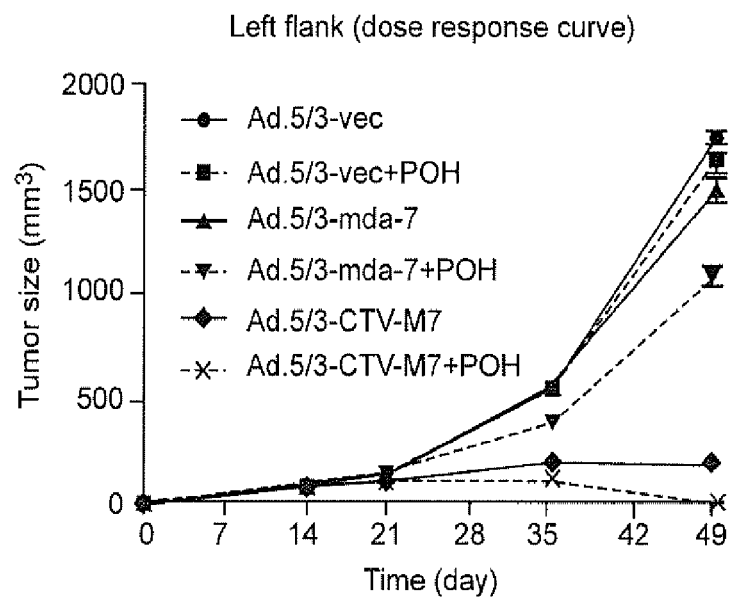
Figure 12B:
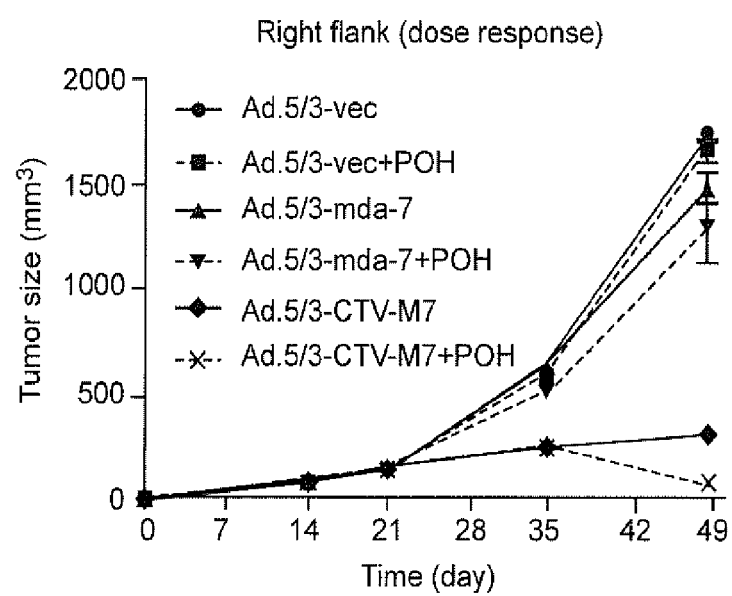
Figure 12C:
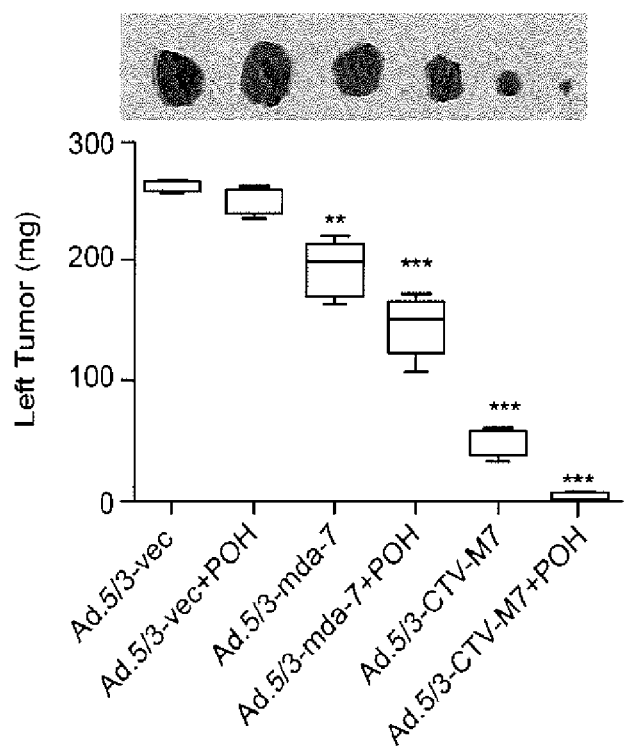
Figure 12D:
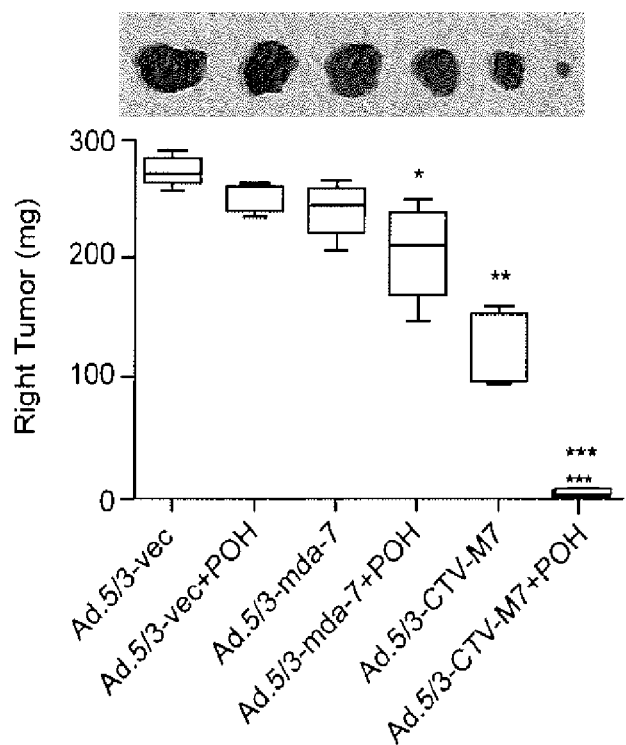
Figure 12E:
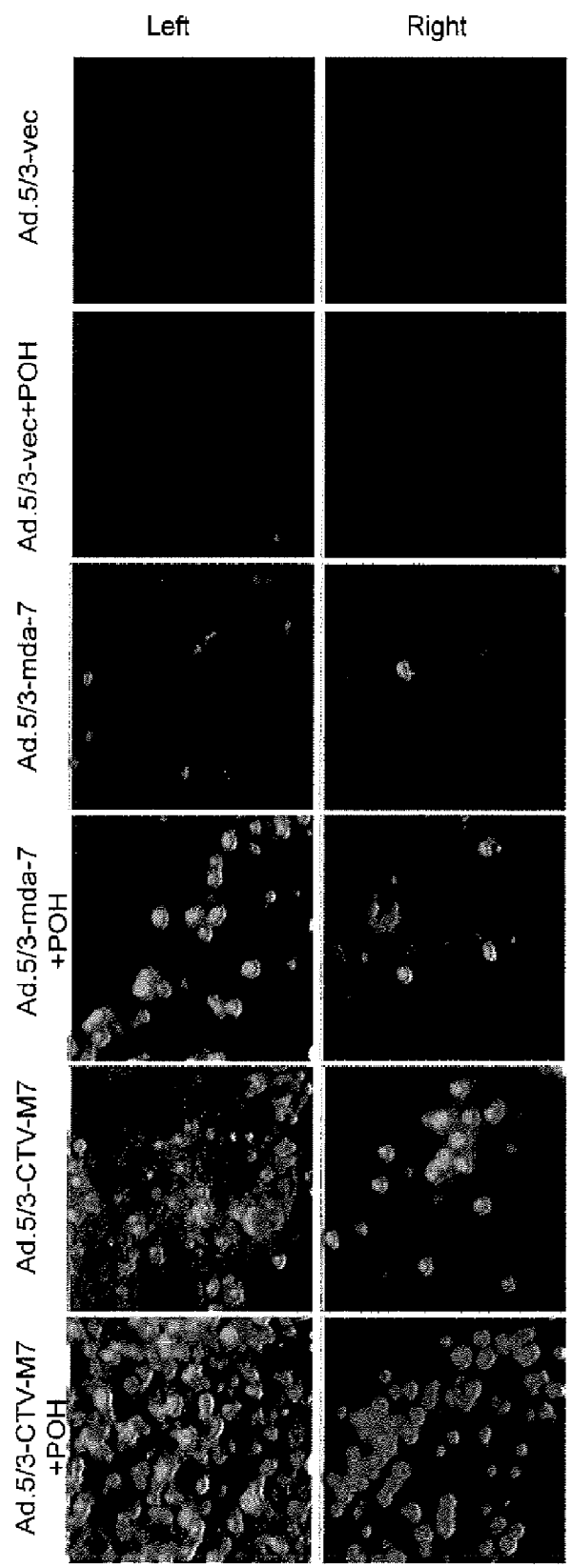
Figure 13A:
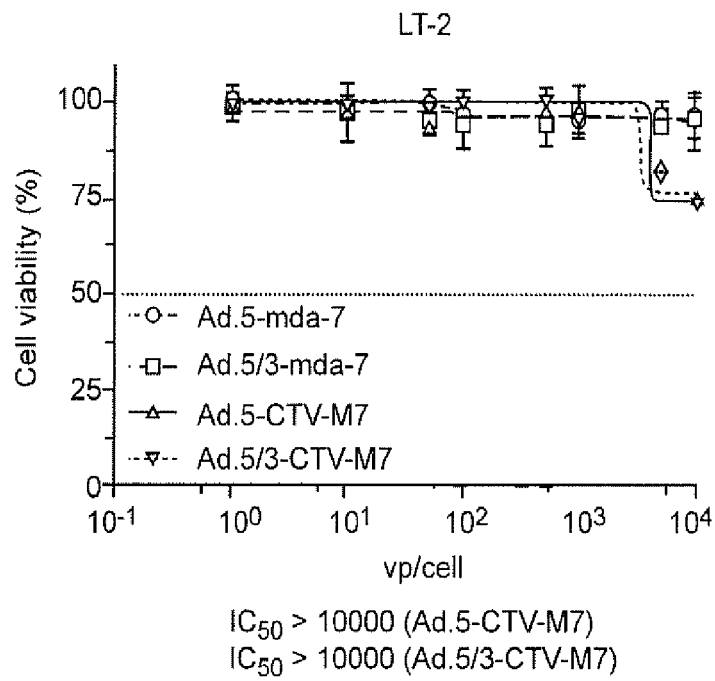
Figure 13B:
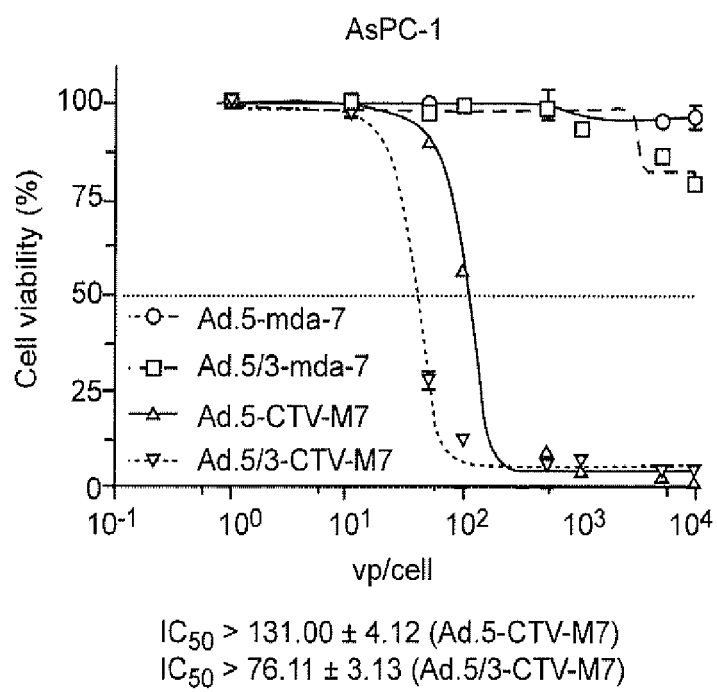
Figure 13C:
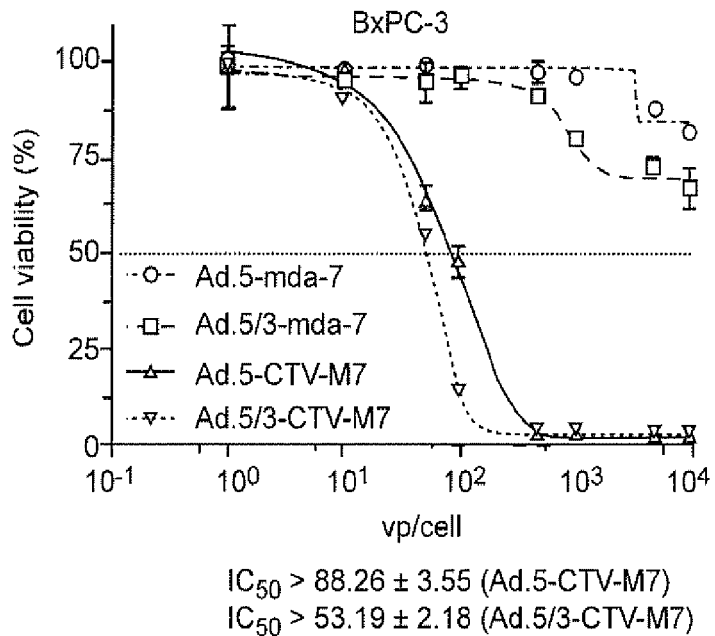
Figure 13D:
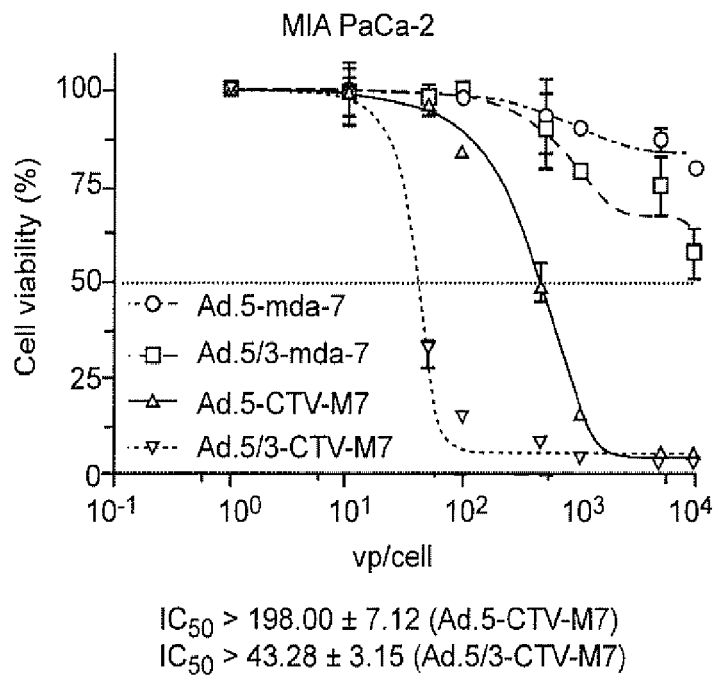

Enhanced Antitumor In Vivo Effect of Chimeric Modified CTV-M7/MB in Combination with POH in Therapy-Resistant PDAC, Potential Clinical Significance Bcl-xL is overexpressed in PDAC and transcriptionally regulated by activated Ras-Raf-MAPK signaling and as well as NF-κB/STAT3 signaling pathways [60-62] which contributes to chemoresistance [63] and poor prognosis in pancreatic cancer patients [53, 64, 65]. Chemotherapy regimens like 5-flurouracil (5-FU) and gemcitabine are standard first line therapeutics employed in clinics for the treatment of advanced pancreatic cancers. Repeated exposure of PDAC cells to 5-FU and gemcitabine leads to enhanced anti-apoptotic Bcl-xL expression [63], which eventually can promote chemotherapy resistance in pancreatic cancers, and is a causal factor in disease progression. In order to evaluate a therapy-resistant PDAC model system, we used MIA PaCa-2/Bcl-xL (MIA PaCa-2 cells overexpressing Bcl-xL) to initiate tumors on both flanks of nude mice. Twelve to fourteen days after tumor cell injection, mice were treated as mentioned previously, using MB and ultrasound with the UTMD approach, with replication incompetent Ad.5/3-mda-7 or replication competent Ad.5/3-CTV-M7 with or without POH. There was a significant decrease in tumor volume as well as tumor mass of the sonoporated left-flank in Ad.5/3-CTV-M7 and Ad.5/3-CTV-M7+POH treated group as compared to Ad.5/3-vec treated group (FIGS. 12A, 12B, 12C and 12D). Although we observed a statistically significant decrease in the tumor size of right flank tumors in mice treated with Ad.5/3-CTV-M7 alone in the left flank tumors, a profound decrease in tumor size of the right flank tumors was observed in those mice treated with Ad.5/3-CTV-M7 plus POH. Since this combination induces a significant increase in the production and secretion of MDA-7/IL-24 protein (FIGS. 8, 10A-G and 11A-E), the combinatorial effect of this CGT treatment supports the prominent role of secreted MDA-7/IL-24 in executing its 'bystander' effect in reducing growth and killing the secondary untreated tumor in this therapy-resistant PDAC model (FIG. 12A-E). Bcl-xL leads to intrinsic resistance to mda-7/IL-24-mediated apoptosis in PDAC cells, as observed in prostate cancer cells [39], which was reversed upon treatment with Ad.5/3-CTV-M7. This tumor inhibition was enhanced further in the presence of POH, as shown by TUNEL staining of tumor cells (FIG. 12E).

Discussion

Based on cell culture studies and preclinical animal models, it was assumed that viruses, particularly viruses that could conditionally replicate in cancer cells, would provide ideal weapons to treat cancer [58]. Unfortunately, this promise has not been realized and the majority of clinical cancer trials using virally administered gene therapies have produced only marginal positive results, and responses have not been enduring. The efficacy of therapeutic viruses has been even more disappointing in the context of metastatic disease. Newer strategies, including modifying the tropism of viruses to enhance their delivery to tumor cells, improved strategies for targeted delivery of therapeutic viruses and development of bipartite viruses that not only replicate selectively in cancer cells but can also produce a therapeutic gene product that destroys distant tumor cells through 'bystander' activity are bringing us closer to realizing the promise of therapeutic viruses to treat cancer [58]. In order to increase the therapeutic efficacy of Ads by enhancing their infectivity and the ability to deliver transgenes to cancer cells, Ads have been genetically modified resulting in chimeric recombinant Ad.5/3 which displays increased efficacy in infecting cells irrespective of CAR receptors [2, 13, 31, 66]. To increase the therapeutic impact of the Ad.5/3 virus we engineered this virus to display cancer-specific replication by using the PEG-Prom [4] and further augmented therapeutic ability by incorporating an additional therapeutic gene, either interferon gamma or mda-7/IL-24, referred to as CTVs (CTV-γ; and CTV-M7), which would permit distant 'bystander' anticancer activity [2, 4, 6, 7, 11]. Systemic administration of Ad.5/3-PEG-E1A, a cancer-specific replicating Ad (CRCA), using a MB plus ultrasound (UTMD) approach leads to a significant change in tumor volume in a treated tumor, without significantly changing tumor size of a secondary tumor (reflecting a potential metastasis) implanted on the opposite flank, even though these CRCAs theoretically have the potential to migrate to this distant tumor site in athymic animals. These results emphasize the inefficiency of using only a CRCA systemically, suggesting that the ability to transfer adequate amounts of bioactive CRCAs to a distant secondary tumor site is difficult (and perhaps impossible to achieve, using current vectors and direct systemic delivery approaches). In contrast, further arming of CRCAs with a therapeutic transgene that is a secreted cytokine, such as mda-7/IL-24 [7, 8, 19], results in improved clinical responses by the combined effect of oncolysis and robust MDA-7/IL-24 production and secretion [6, 7, 67]. Thus, CTV-M7 can act on distant tumor cells (FIGS. 11A-E and 12A-E) and limits the growth of the distant tumor [2, 7, 67].

Although mda-7/IL-24 effectively induces apoptosis in a wide spectrum of cancer cells of diverse origin, pancreatic cancer cells are refractory to mda-7/IL-24-mediated killing due to inhibition of mda-7/IL-24 mRNA translation into protein [15, 32, 38]. We previously demonstrated that ROS induced by POH enriched association of mda-7/IL-24 mRNA with polysomes leading to enhanced translation into MDA-7/IL-24 protein [32]. The exact mechanism of action of POH in enhancing the translation of mda-7/IL-24 mRNA into protein requires further investigation. Earlier preclinical studies documented chemotherapeutic effects of POH or its derivatives in inhibiting liver, prostate [68], colon [69] and pancreatic cancer [70], but this effectiveness did not translate in Phase II clinical trials of POH in metastatic prostate [71], metastatic refractory breast [72] and colon cancer [73]. In most clinical studies employing POH, treatment was initiated after the onset of cancer and its metastasis, which might be the reason for its ineffective clinical activity when used at the prescribed non-toxic dose. It is possible that POH could be used to inhibit the initiation of pancreatic cancer (chemoprevention) if taken daily in food supplements in high-risk groups [2], which has not been adequately explored. POH also synergizes with radiotherapy or chemotherapy in inhibiting various cancers [74, 75]. Through synergy with other modes of therapy, the clinical dose of POH might be reduced to a tolerable and achievable physiological level. We observed a transient increase in ROS formation even at a low physiologically achievable dose of ~200 µM of POH. This dose is sufficient to activate the protein translation machinery by activation of p-70S6K/p4EBP-1 that helps in formation of pre-initiation complex, and thus enhanced MDA-7/IL-24 protein expression from the weakly translated mda-7/IL-24 mRNA (unpublished data). This present study highlights that using two agents with complementary mechanisms of action may prove more efficacious than administering a single agent in the therapy of pancreatic cancer, and the robust expression of MDA-7/IL-24 along with the combined oncolytic effects associated with CTV-M7 plus POH might be effective in eliminating the residual tumors and thus providing a way to prevent disease relapse.

Pancreatic cancer is refractory to conventional therapies, which may be a consequence of the accumulation of multiple genetic alterations with disease progression that is further complicated by the presence of metastasis at the time of diagnosis. These genetic mutations often lead to constitutive K-Ras and NF-κB activation, which is associated with >90% of PDAC [2, 61]. Ras-Raf-MAPK signaling as well as NF-κB/STAT3 signaling pathways lead to transcriptional up-regulation of Bcl-xL in PDAC [60-62], which contributes to chemoresistance [63] and poor prognosis in pancreatic cancer patients [53, 64, 65]. Present results indicate that Bcl-xL is significantly downregulated upon mda-7/IL-24 expression with maximum decreases when combined with POH treatment, whereas overexpression of Bcl-xL imparts protection to mda-7/IL-24-induced apoptosis in PDAC (FIGS. 8 and 10A-G). Our previous studies indicated that Bcl-xL differentially protects cancer cells from MDA-7/IL-24-induced apoptosis [39]. Although Bcl-xL can produce resistance towards MDA-7/IL-24-mediated apoptosis, overexpressing MDA-7/IL-24 by CTVs (which results in higher levels of this cytokine) can circumvent resistance by enhancing and prolonging ER stress that switches from pro-survival to pro-apoptotic signaling that leads to cell death. Our data demonstrates that CRCAs expressing the mda-7/IL-24 transgene (Ad.5/3-PEG-E1A-mda-7; Ad.5/3-CTV-M7) reduce PDAC tumors in the treated left flank of mice as compared to Ad.5/3-vec and Ad.5/3-mda-7, which may be due to the oncolytic properties of Ad.5/3-CTV-M7 combined with the apoptosis-promoting properties of MDA-7/IL-24. Combination CGT therapy with POH and Ad.5/3-CTV-M7 leads to profound changes in tumor volume in the secondary site (tumors on the opposite flank of animals) as compared to either agent alone in a therapy-resistant in vivo model of PDAC. Apart from the role of POH in promoting enhanced MDA-7/IL-24 expression, which might initiate sustained ER stress, its role in ROS generation leading to mitochondrial stress may also contribute to enhanced cancer cell killing. Both ER stress and mitochondrial stress might cooperate and promote signal transduction changes leading to apoptosis even in therapy-resistant PDAC. Through a detailed understanding of precisely how MDA-7/IL-24 induces cancer-specific apoptosis, irrespective of genetic diversity in tumors, with complementary and additional cellular alterations promoted by POH might provide a viable combinatorial approach in treating pancreatic cancers where all other therapeutic modalities prove ineffectual.

In summary, this Example 2 highlights a chemoprevention gene therapy (CGT) strategy for the effective therapy of PDAC in vitro and in vivo in animal models with tumors on both flanks. We highlight that Ad.5/3-CTV-M7/MB coupled with the novel UTMD delivery approach [14, 29] as a non-toxic and precise method of targeted gene delivery, which when combined with POH, which augments the expression of mda-7/IL-24 by facilitating its translation into protein, sensitizes PDAC to mda-7/IL-24-mediated cytotoxicity, thereby significantly enhancing therapeutic efficacy. The combinatorial approach is superior to Ad.5/3-CTV-M7 alone or POH used as a single modality treatment as physiologically achievable doses. Based on the safety and diagnostic profile of MBs, which are now in Phase II and III clinical trials for cardiovascular disease the profound potential clinical value of Ad.5/3-CTV-M7, and the fact that mda-7/IL-24 has been successfully translated into the clinic in a Phase I clinical trial [22-26] as safe and efficacious in advanced cancers, this unique CGT strategy may be translated into the clinic for the treatment of currently incurable pancreatic cancers.

References for Example 2

[1] American Cancer Society. Cancer Facts and Figures 2012. Atlanta, Ga.: American Cancer Society Inc. 2012.

[2] Sarkar S, Azab B M, Das S K, et al. Chemoprevention gene therapy (CGT): novel combinatorial approach for preventing and treating pancreatic cancer. Curr Mol Med 2012;

[3] Garber K. China approves world's first oncolytic virus therapy for cancer treatment. J Natl Cancer Inst 2006; 98: 298-300.
[4] Su Z Z, Sarkar D, Emdad L, et al. Targeting gene expression selectively in cancer cells by using the progression-elevated gene-3 promoter. Proc Natl Acad Sci USA 2005; 102: 1059-64.
[5] Su Z Z, Shi Y, Fisher P B. Subtraction hybridization identifies a transformation progression-associated gene PEG-3 with sequence homology to a growth arrest and DNA damage-inducible gene. Proc Natl Acad Sci USA 1997; 94: 9125-30.
[6] Sarkar D, Su Z Z, Park E S, et al. A cancer terminator virus eradicates both primary and distant human melanomas. Cancer Gene Ther 2008; 15: 293-302.
[7] Sarkar D, Su Z Z, Vozhilla N, Park E S, Gupta P, Fisher P B. Dual cancer-specific targeting strategy cures primary and distant breast carcinomas in nude mice. Proc Natl Acad Sci USA 2005; 102: 14034-9.
[8] Sauane M, Gopalkrishnan R V, Sarkar D, et al. MDA-7/IL-24: novel cancer growth suppressing and apoptosis inducing cytokine. Cytokine Growth Factor Rev 2003; 14: 35-51.
[9] Sauane M, Su Z Z, Gupta P, et al. Autocrine regulation of mda-7/IL-24 mediates cancer-specific apoptosis. Proc Natl Acad Sci USA 2008; 105: 9763-8.
[10] Dash R, Bhutia S K, Azab B, et al. mda-7/IL-24: a unique member of the IL-10 gene family promoting cancer-targeted toxicity. Cytokine Growth Factor Rev 2010; 21: 381-91.
[11] Sarkar D, Su Z Z, Vozhilla N, et al. Targeted virus replication plus immunotherapy eradicates primary and distant pancreatic tumors in nude mice. Cancer Res 2005; 65: 9056-63.
[12] Pearson A S, Koch P E, Atkinson N, et al. Factors limiting adenovirus-mediated gene transfer into human lung and pancreatic cancer cell lines. Clin Cancer Res 1999; 5: 4208-13.
[13] Dash R, Dmitriev I, Su Z Z, et al. Enhanced delivery of mda-7/IL-24 using a serotype chimeric adenovirus (Ad.5/3) improves therapeutic efficacy in low CAR prostate cancer cells. Cancer Gene Ther 2010; 17: 447-56.
[14] Dash R, Azab B, Quinn B A, et al. Apogossypol derivative BI-97C1 (Sabutoclax) targeting Mcl-1 sensitizes prostate cancer cells to mda-7/IL-24-mediated toxicity. Proc Natl Acad Sci USA 2011; 108: 8785-90.
[15] Su Z, Lebedeva I V, Gopalkrishnan R V, et al. A combinatorial approach for selectively inducing programmed cell death in human pancreatic cancer cells. Proc Natl Acad Sci USA 2001; 98: 10332-7.
[16] Lebedeva I V, Emdad L, Su Z Z, et al. mda-7/IL-24, novel anticancer cytokine: focus on bystander antitumor, radiosensitization and antiangiogenic properties and overview of the phase I clinical experience (Review). Int J Oncol 2007; 31: 985-1007.
[17] Emdad L, Sarkar D, Lebedeva I V, et al. Ionizing radiation enhances adenoviral vector expressing mda-7/IL-24-mediated apoptosis in human ovarian cancer. J Cell Physiol 2006; 208: 298-306.
[18] McKenzie T, Liu Y, Fanale M, Swisher S G, Chada S, Hunt K K. Combination therapy of Ad-mda7 and trastuzumab increases cell death in Her-2/neu-overexpressing breast cancer cells. Surgery 2004; 136: 437-42.
[19] Jiang H, Lin J J, Su Z Z, Goldstein N I, Fisher P B. Subtraction hybridization identifies a novel melanoma differentiation associated gene, mda-7, modulated during human melanoma differentiation, growth and progression. Oncogene 1995; 11: 2477-86.
[20] Sarkar D, Su Z Z, Lebedeva I V, et al. mda-7 (IL-24) Mediates selective apoptosis in human melanoma cells by inducing the coordinated overexpression of the GADD family of genes by means of p38 MAPK. Proc Natl Acad Sci USA 2002; 99: 10054-9.
[21] Das S K, Sarkar S, Dash R, et al. Chapter One—Cancer terminator viruses and approaches for enhancing therapeutic outcomes. Adv Cancer Res 2012; 115: 1-38.
[22] Eager R, Harle L, Nemunaitis J. Ad-MDA-7; INGN 241: a review of preclinical and clinical experience. Expert Opin Biol Ther 2008; 8: 1633-43.
[23] Tong A W, Nemunaitis J, Su D, et al. Intratumoral injection of INGN 241, a nonreplicating adenovector expressing the melanoma-differentiation associated gene-7 (mda-7/IL24): biologic outcome in advanced cancer patients. Mol Ther 2005; 11: 160-72.
[24] Fisher P B, Gopalkrishnan R V, Chada S, et al. mda-7/IL-24, a novel cancer selective apoptosis inducing cytokine gene: from the laboratory into the clinic. Cancer Biol Ther 2003; 2: S23-37.
[25] Fisher P B, Sarkar D, Lebedeva I V, et al. Melanoma differentiation associated gene-7/interleukin-24 (mda-7/IL-24): novel gene therapeutic for metastatic melanoma. Toxicol Appl Pharmacol 2007; 224: 300-7.
[26] Cunningham C C, Chada S, Merritt J A, et al. Clinical and local biological effects of an intratumoral injection of mda-7 (IL24; INGN 241) in patients with advanced carcinoma: a phase I study. Mol Ther 2005; 11: 149-59.
[27] Hamid O, Varterasian M L, Wadler S, et al. Phase II trial of intravenous CI-1042 in patients with metastatic colorectal cancer. J Clin Oncol 2003; 21: 1498-504.
[28] Muruve D A. The innate immune response to adenovirus vectors. Hum Gene Ther 2004; 15: 1157-66.
[29] Greco A, Di Benedetto A, Howard C M, et al. Eradication of therapy-resistant human prostate tumors using an ultrasound-guided site-specific cancer terminator virus delivery approach. Mol Ther 2010; 18: 295-306.
[30] Dash R, Azab B, Shen X N, et al. Developing an effective gene therapy for prostate cancer: New technologies with potential to translate from the laboratory into the clinic. Discov Med 2011; 11: 46-56.
[31] Azab B, Dash R, Das S K, et al. Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells. J Cell Physiol 2012; 227: 2145-53.
[32] Lebedeva I V, Su Z Z, Vozhilla N, et al. Mechanism of in vitro pancreatic cancer cell growth inhibition by melanoma differentiation-associated gene-7/interleukin-24 and perillyl alcohol. Cancer Res 2008; 68: 7439-47.
[33] Lebedeva I V, Su Z Z, Sarkar D, et al. Induction of reactive oxygen species renders mutant and wild-type K-ras pancreatic carcinoma cells susceptible to Ad.mda-7-induced apoptosis. Oncogene 2005; 24: 585-96.
[34] Bell E L, Klimova T A, Eisenbart J, Schumacker P T, Chandel N S. Mitochondrial reactive oxygen species trigger hypoxia-inducible factor-dependent extension of the replicative life span during hypoxia. Mol Cell Biol 2007; 27: 5737-45.
[35] Gerasimovskaya E V, Tucker D A, Stenmark K R. Activation of phosphatidylinositol 3-kinase, Akt, and mammalian target of rapamycin is necessary for hypoxia-induced pulmonary artery adventitial fibroblast proliferation. J Appl Physiol 2005; 98: 722-31.

[36] Huang C, Li J, Ke Q, et al. Ultraviolet-induced phosphorylation of p70(S6K) at Thr(389) and Thr(421)/Ser (424) involves hydrogen peroxide and mammalian target of rapamycin but not Akt and atypical protein kinase C. Cancer Res 2002; 62: 5689-97.

[37] Bae G U, Seo D W, Kwon H K, et al. Hydrogen peroxide activates p70(S6k) signaling pathway. J Biol Chem 1999; 274: 32596-602.

[38] Lebedeva I V, Su Z Z, Vozhilla N, et al. Chemoprevention by perillyl alcohol coupled with viral gene therapy reduces pancreatic cancer pathogenesis. Mol Cancer Ther 2008; 7: 2042-50.

[39] Lebedeva I V, Sarkar D, Su Z Z, et al. Bcl-2 and Bcl-x(L) differentially protect human prostate cancer cells from induction of apoptosis by melanoma differentiation associated gene-7, mda-7/IL-24. Oncogene 2003; 22: 8758-73.

[40] Webb J L. Effect of more than one inhibitor. Enzyme and Metabolic Inhibitors. New York: Academic Press; 1963. p. 66-79.

[41] Chou T C. Theoretical basis, experimental design, and computerized simulation of synergism and antagonism in drug combination studies. Pharmacol Rev 2006; 58: 621-81.

[42] Howard C M, Forsberg F, Minimo C, Liu J B, Merton D A, Claudio P P. Ultrasound guided site specific gene delivery system using adenoviral vectors and commercial ultrasound contrast agents. J Cell Physiol 2006; 209: 413-21.

[43] Ripple G H, Gould M N, Stewart J A, et al. Phase I clinical trial of perillyl alcohol administered daily. Clin Cancer Res 1998; 4: 1159-64.

[44] Hudes G R, Szarka C E, Adams A, et al. Phase I pharmacokinetic trial of perillyl alcohol (NSC 641066) in patients with refractory solid malignancies. Clin Cancer Res 2000; 6: 3071-80.

[45] da Fonseca C O, Simao M, Lins I R, Caetano R O, Futuro D, Quirico-Santos T. Efficacy of monoterpene perillyl alcohol upon survival rate of patients with recurrent glioblastoma. J Cancer Res Clin Oncol 2011; 137: 287-93.

[46] McGuire K A, Barlan A U, Griffin T M, Wiethoff C M. Adenovirus type 5 rupture of lysosomes leads to cathepsin B-dependent mitochondrial stress and production of reactive oxygen species. J Virol 2011; 85: 10806-13.

[47] Gupta P, Walter M R, Su Z Z, et al. BiP/GRP78 is an intracellular target for MDA-7/IL-24 induction of cancer-specific apoptosis. Cancer Res 2006; 66: 8182-91.

[48] Wu J, Kaufman R J. From acute ER stress to physiological roles of the Unfolded Protein Response. Cell Death Differ 2006; 13: 374-84.

[49] Pataer A, Hu W, Xiaolin L, et al. Adenoviral endoplasmic reticulum-targeted mda-7/interleukin-24 vector enhances human cancer cell killing. Mol Cancer Ther 2008; 7: 2528-35.

[50] Hinz S, Trauzold A, Boenicke L, et al. Bcl-XL protects pancreatic adenocarcinoma cells against CD95- and TRAIL-receptor-mediated apoptosis. Oncogene 2000; 19: 5477-86.

[51] Campani D, Esposito I, Boggi U, et al. Bcl-2 expression in pancreas development and pancreatic cancer progression. J Pathol 2001; 194: 444-50.

[52] Evans J D, Cornford P A, Dodson A, Greenhalf W, Foster C S, Neoptolemos J P. Detailed tissue expression of bcl-2, bax, bak and bcl-x in the normal human pancreas and in chronic pancreatitis, ampullary and pancreatic ductal adenocarcinomas. Pancreatology 2001; 1: 254-62.

[53] Bai J, Sui J, Demirjian A, Vollmer C M, Jr., Marasco W, Callery M P. Predominant Bcl-XL knockdown disables antiapoptotic mechanisms: tumor necrosis factor-related apoptosis-inducing ligand-based triple chemotherapy overcomes chemoresistance in pancreatic cancer cells in vitro. Cancer Res 2005; 65: 2344-52.

[54] Carrington E M, McKenzie M D, Jansen E, et al. Islet beta-cells deficient in Bcl-xL develop but are abnormally sensitive to apoptotic stimuli. Diabetes 2009; 58: 2316-23.

[55] Morishima N, Nakanishi K, Tsuchiya K, Shibata T, Seiwa E. Translocation of Bim to the endoplasmic reticulum (ER) mediates ER stress signaling for activation of caspase-12 during ER stress-induced apoptosis. J Biol Chem 2004; 279: 50375-81.

[56] Zhou Y P, Pena J C, Roe M W, et al. Overexpression of Bcl-x(L) in beta-cells prevents cell death but impairs mitochondrial signal for insulin secretion. Am J Physiol Endocrinol Metab 2000; 278: E340-51.

[57] Szegezdi E, Logue S E, Gorman A M, Samali A. Mediators of endoplasmic reticulum stress-induced apoptosis. EMBO Rep 2006; 7: 880-5.

[58] Curiel D T, Fisher P B. Advances in Cancer Research: Applications of viruses for cancer therapy. 1st ed2012. 1-326 p.

[59] Jiang H, Wang Z, Serra D, Frank M M, Amalfitano A. Recombinant adenovirus vectors activate the alternative complement pathway, leading to the binding of human complement protein C3 independent of anti-ad antibodies. Mol Ther 2004; 10: 1140-2.

[60] Boucher M J, Morisset J, Vachon P H, Reed J C, Laine J, Rivard N. MEK/ERK signaling pathway regulates the expression of Bcl-2, Bcl-X(L), and Mcl-1 and promotes survival of human pancreatic cancer cells. J Cell Biochem 2000; 79: 355-69.

[61] Greten F R, Weber C K, Greten T F, et al. Stat3 and NF-kappaB activation prevents apoptosis in pancreatic carcinogenesis. Gastroenterology 2002; 123: 2052-63.

[62] Hamacher R, Schmid R M, Saur D, Schneider G. Apoptotic pathways in pancreatic ductal adenocarcinoma. Mol Cancer 2008; 7: 64.

[63] Shi X, Liu S, Kleeff J, Friess H, Buchler M W. Acquired resistance of pancreatic cancer cells towards 5-Fluorouracil and gemcitabine is associated with altered expression of apoptosis-regulating genes. Oncology 2002; 62: 354-62.

[64] Friess H, Lu Z, Andren-Sandberg A, et al. Moderate activation of the apoptosis inhibitor bcl-xL worsens the prognosis in pancreatic cancer. Ann Surg 1998; 228: 780-7.

[65] Westphal S, Kalthoff H. Apoptosis: targets in pancreatic cancer. Mol Cancer 2003; 2: 6.

[66] Hamed H A, Yacoub A, Park M A, et al. Inhibition of multiple protective signaling pathways and Ad.5/3 delivery enhances mda-7/IL-24 therapy of malignant glioma. Mol Ther 2010; 18: 1130-42.

[67] Chada S, Mhashilkar A M, Ramesh R, et al. Bystander activity of Ad-mda7: human MDA-7 protein kills melanoma cells via an IL-20 receptor-dependent but STAT3-independent mechanism. Mol Ther 2004; 10: 1085-95.

[68] Chung B H, Lee H Y, Lee J S, Young C Y. Perillyl alcohol inhibits the expression and function of the androgen receptor in human prostate cancer cells. Cancer Lett 2006; 236: 222-8.

[69] Bardon S, Foussard V, Fournel S, Loubat A. Monoterpenes inhibit proliferation of human colon cancer cells by modulating cell cycle-related protein expression. Cancer Lett 2002; 181: 187-94.

[70] Stark M J, Burke Y D, McKinzie J H, Ayoubi A S, Crowell P L. Chemotherapy of pancreatic cancer with the monoterpene perillyl alcohol. Cancer Lett 1995; 96: 15-21.

[71] Liu G, Oettel K, Bailey H, et al. Phase II trial of perillyl alcohol (NSC 641066) administered daily in patients with metastatic androgen independent prostate cancer. Invest New Drugs 2003; 21: 367-72.

[72] Bailey H H, Attia S, Love R R, et al. Phase II trial of daily oral perillyl alcohol (NSC 641066) in treatment-refractory metastatic breast cancer. Cancer Chemother Pharmacol 2008; 62: 149-57.

[73] Meadows S M, Mulkerin D, Berlin J, et al. Phase II trial of perillyl alcohol in patients with metastatic colorectal cancer. Int J Gastrointest Cancer 2002; 32: 125-8.

[74] Rajesh D, Stenzel R A, Howard S P. Perillyl alcohol as a radio-/chemosensitizer in malignant glioma. J Biol Chem 2003; 278: 35968-78.

[75] da Fonseca C O, Linden R, Futuro D, Gattass C R, Quirico-Santos T. Ras pathway activation in gliomas: a strategic target for intranasal administration of perillyl alcohol. Arch Immunol Ther Exp (Warsz) 2008; 56: 267-76.

Example 3

Histone Deacetylase Inhibitors Interact with MDA-7/IL-24 to Kill Primary Human Glioblastoma Cells Abstract We presently demonstrate that histone deacetylase inhibitors (HDACIs) enhance toxicity of melanoma differentiation associated gene-7/interleukin 24 (mda-7/IL-24) in invasive primary human GBM cells. Additionally, a method is described to augment efficacy of adenoviral delivery of mda-7/IL-24 in these cells. HDACIs synergized with MDA-7/IL-24 killing GBM cells. Enhanced lethality correlated with increased autophagy that was dependent on expression of ceramide synthase 6. HDACIs interacted with MDA-7/IL-24 prolonging generation of ROS and $Ca^{2+}$. Quenching of ROS and $Ca^{2+}$ blocked HDACI and MDA-7/IL-24 killing. In vivo MDA-7/IL-24 prolonged survival of animals carrying orthotopic tumors and HDACIs enhanced survival further. A serotype 5/3 adenovirus more effectively delivers mda-7/IL-24 to GBM tumors than a serotype 5 virus. Hence, we constructed a serotype 5/3 adenovirus that conditionally replicates in tumor cells expressing MDA-7/IL-24, in which the adenoviral E1A gene was driven by the cancer-specific promoter progression elevated gene-3 (Ad.5/3-PEG-E1A-mda-7; also called Ad.5/3-CTV; Ad.5/3-CTV-M7). Ad.5/3-CTV (Ad.5/3-CTV-M7) increased survival of mice carrying GBM tumors to a significantly greater extent than did a non-replicative virus Ad.5/3-mda-7. Ad.5/3-CTV (Ad.5/3-CTV-M7) exhibited no toxicity in the brains of Syrian hamsters. Collectively our data demonstrates that HDACIs enhance MDA-7/IL-24 lethality and adenoviral delivery of mda-7/IL-24 combined with tumor specific viral replication is an effective pre-clinical GBM therapeutic.

Introduction

Glioblastoma multiforme (GBM) is diagnosed in ~20,000 patients per annum (Robins et al, 2007). Even under circumstances in which virtually all of the tumor can be surgically removed and the patients are maximally treated with radiation and chemotherapy, the mean survival of this disease is only extended from 3 months to 1 year (Robins et al, 2007).

The mda-7 gene (Interleukin 24, IL-24) was isolated from human melanoma cells induced to undergo differentiation by treatment with interferon and mezerein (Jiang et al, 1995). The expression of MDA-7/IL-24 protein is decreased in advanced melanomas, with almost undetectable levels in metastatic disease (Jiang et al, 1995; Ekmekcioglu et al, 2001; Ellerhorst et al, 2002). Enforced expression of MDA-7/IL-24, by use of a recombinant adenovirus Ad.5-mda-7, inhibits the growth and kills a broad spectrum of cancer cells, without exerting harmful effects in normal human epithelial or fibroblast cells (Gupta et al, 2006; Lebedeva et al, 2005; Fisher et al, 2003; Fisher 2005; Su et al, 2001; Su et al, 1998). Mda-7/IL-24 was evaluated in a Phase I clinical trial in patients with advanced cancers indicating that an Ad.5-mda-7 (INGN 241) injected intra-tumorally was safe and with repeated injections, significant clinical activity was evident (Lebedeva et al, 2005; Fisher et al, 2003; Cunningham et al, 2005).

The ability of MDA-7/IL-24 to modulate cell survival processes in transformed cells has been investigated by our groups (Dash et al, 2010; Dent et al, 2010a; Dent et al, 2010b; Bhutia et al, 2011; Sauane et al, 2010; Yacoub et al, 2010a; Yacoub et al, 2008a; Yacoub et al, 2008b). Prior work in GBM cells has shown, using bacterially synthesized GST-MDA-7 protein, that in the low nanomolar concentration range GST-MDA-7 primarily causes a growth arrest response with little induction of cell killing, whereas at ~20-fold greater concentrations, the cytokine causes profound growth arrest and tumor cell death (Sauane et al, 2010; Yacoub et al, 2010a). Key factors implicated in MDA-7/IL-24 toxicity included $Ca^{2+}$ elevation, ceramide generation and reactive oxygen species (ROS) production (Sauane et al, 2010; Yacoub et al, 2010). Expression of MDA-7/IL-24 increased the levels of autophagy, and inhibition of autophagy protected against MDA-7/IL-24 toxicity (Yacoub et al, 2010a; Yacoub et al, 2008a; Yacoub et al, 2008b).

Many cancer gene therapy studies have utilized type 5 adenovirus vectors (Curiel and Fisher, 2012). For a type 5 virus to infect a cell requires expression of the Coxsackie and Adenovirus receptor (CAR), however, CAR is known to be down-regulated in many cancer types including GBM (Curiel and Fisher, 2012; Paul et al, 2008). To circumvent the low efficiency of type 5 adenovirus infection, we created a novel tropism modified vector by replacing the type 5 virus fiber knob with the fiber knob of the type 3 adenovirus resulting in enhanced infection of tumor cells in a CAR-independent manner and our prior pre-clinical studies in prostate cancer and GBM provide evidence for the enhanced therapeutic efficacy of Ad.5/3-mda-7 versus Ad.5-mda-7 (Dash et al, 2010; Hamed et al, 2010). Further studies developed a conditionally replication-competent adenovirus where expression of the adenoviral early region 1A (E1A) virus gene and conditional virus replication was driven by the promoter of progression elevated gene-3 (PEG-3); a promoter which is active only in cancer cells, such as GBM cells, but has little activity in normal cells, such as primary astrocytes (Ad.5-PEG-E1A-mda-7; a cancer terminator virus, Ad.5-CTV (Ad.5-CTV-M7) (Su et al, 2005; Sarkar et al, 2007; Sarkar et al, 2008). Ad.5-CTV (Ad.5-CTV-M7) injected into prostate cancer or melanoma xenografts in athymic mice eradicated both the primary infected tumor but also an uninfected tumor growing on the opposite flank (Sarkar et al, 2007; Sarkar et al, 2008). This finding can be explained by the fact that secreted MDA-7/IL-24 protein, generated from cells infected with Ad.5-mda-7, induces growth inhibition and apoptosis in surrounding non-infected cancer cells, through a "bystander" anti-tumor effect (Sauane et al, 2008; Emdad et al, 2009).

HDAC inhibitors (HDACIs) are a structurally diverse class of agents, e.g., vorinostat (SAHA; Zolinza) and sodium valproate, (Depakote). These agents block histone deacetylation and neutralization of positively charged lysine residues on histone tails, thereby modifying chromatin structure/condensation and transcription (Ellis and Pili, 2010; Spiegel et al, 2012). The mode of HDACI action is in fact multifactorial with an additional ~20 targets (Dai et al, 2005; Frew et al, 2009; Tang et al, 2012). We have shown that induction of DNA damage and the generation of ceramide and ROS production is a common mechanism involved in both MDA-7/IL-24 and HDACs-induced anti-tumor activity. As with MDA-7/IL-24, HDACIs have been shown to have selective toxicity in tumor cells compared to non-transformed cells (Rosato and Grant, 2004).

The present studies were performed to determine whether MDA-7/IL-24 and HDACIs could interact to kill GBM cells and whether a serotype 5/3 adenovirus that conditionally replicates in tumor cells expressing MDA-7/IL-24 increased the survival of mice carrying GBM tumors to a greater extent than did a non-replicative virus Ad.5/3-mda-7.

Materials and Methods.

Materials.

Suberohydroxamic acid (SBHA) and Vorinostat (SAHA) were supplied by Calbiochem (San Diego, Calif.) as a powder, dissolved in sterile DMSO, and stored frozen under light-protected conditions at −80° C. Trypsin-EDTA, DMEM and RPMI medium, and penicillin-streptomycin were purchased from GIBCOBRL (GIBCOBRL Life Technologies, Grand Island, N.Y.). Dr. C. D. James, University of California, San Francisco very generously originally supplied primary human GBM cells (GBM6, GBM12, GBM14) and information on the genetic background of such cells. Dr. S Spiegel (VCU) supplied the plasmid to express LC3-GFP. Other reagents were of the highest quality commercially available (Yacoub et al, 2010a; Yacoub et al, 2008a; Yacoub et al, 2008b; Sarkar et al, 2008).

Methods.

Generation of Adenoviruses. Recombinant serotype 5 and serotype 5/3 adenoviruses to express MDA-7/IL-24 and control empty vector were generated as described in refs. Dash et al, 2010; Hamed et al, 2010. Ad5/3.PEG-E1.mda-7 (Ad.5/3-CTV; Ad.5/3-CTV-M7) was prepared in collaboration with Drs. Igor Dmitriev and David Curiel, Washington University School of Medicine in Saint Louis, Mo. This recombinant virus was generated in three consecutive steps. 1) Homologous recombination of pAd5/3 genomic plasmid with pShuttlE3 plasmid containing the mda-7/IL-24 expression cassette and kanamycin selection resulted in the pAd5/3.E3-mda-7 genome. 2) pAd5/3.E3-mda-7 was cut with Swa I to excise the kanamycin resistance gene. 3) The resultant pAd5/3.E3-mda-7 plasmid was recombined with pShuttlE1 plasmid containing E1A and E1B genes under control of the PEG-3 promoter resulting in Ad5/3.PEG-E1.mda-7 (Ad5/3-CTV; Ad.5/3-CTV-M7) genomic plasmid. This plasmid was digested with Pac I to release viral ITRs and transfected in A549 cells to rescue the CRCA, Ad.5/3-CTV (Ad.5/3-CTV-M7). Similar strategies were used to generate Ad.5/3-cmv-E1A-mda-7 and Ad.5/3-PEG-mda-7. Viruses were expanded and titers determined as previously described (Sarkar et al, 2005; Azab et al, 2012; Dash et al, 2011).

Cell Culture and In Vitro Exposure of Cells to GST-MDA-7, "Ad.mda-7" and Drugs. All GBM lines were cultured at 37° C. (5% (v/v $CO_2$) in vitro using RPMI supplemented with 5% (v/v) fetal calf serum and 10% (v/v) Non-essential amino acids. For short-term cell killing assays and immunoblotting, cells were plated at a density of $3 \times 10^3$ per $cm^2$ and 36 h after plating were treated with MDA-7/IL-24 and/or various drugs, as indicated. In vitro small molecule inhibitor treatments were from a 100 mM stock solution of each drug and the maximal concentration of Vehicle (DMSO) in media was 0.02% (v/v). For adenoviral infection, cells were infected 12 h after plating and the expression of the recombinant viral transgene was allowed to occur for at least 12 h prior to any additional experimental procedure. Cells were not cultured in reduced serum media during any study.

Recombinant Adenoviral Vectors; Infection In Vitro. We generated and purchased previously noted recombinant serotype 5 adenoviruses to express dominant negative caspase 9, c-FLIP-s, CRM A, and BCL-XL (Vector Biolabs, Philadelphia, Pa.). Cells were infected with these adenoviruses at an approximate m.o.i. of 50. Cells were incubated for 24 h to ensure adequate expression of transduced gene products prior to drug exposures.

Detection of Cell Death by Trypan Blue Assays. Cells were harvested by trypsinization with Trypsin/EDTA for ~10 min at 37° C. As some apoptotic cells detached from the culture substratum into the medium, these cells were also collected by centrifugation of the medium at 1,500 rpm for 5 min. The pooled cell pellets were resuspended and mixed with trypan blue dye. Trypan blue stain, in which blue dye incorporating cells were scored as being dead, was performed by counting of cells using a light microscope and a hemacytometer. Five hundred cells from randomly chosen fields were counted and the number of dead cells was counted and expressed as a percentage of the total number of cells counted.

Plasmid Transfection. Plasmid DNA (0.5 g/total plasmid transfected) was diluted into 50 µl of RPMI growth media that lacked supplementation with FBS or with penicillin-streptomycin. Lipofectamine 2000 reagent (1 µl) (Invitrogen, Carlsbad, Calif.) was diluted into 50 µl growth media that lacked supplementation with FBS or with penicillin-streptomycin. The two solutions were then mixed together and incubated at room temperature for 30 min. The total mix was added to each well (4-well glass slide or 12-well plate) containing 200 µl growth media that lacked supplementation with FBS or with penicillin-streptomycin. The cells were incubated for 4 h at 37° C., after which time the media was replaced with RPMI growth media containing 5% (v/v) FBS and 1× pen-strep.

Microscopy for LC3-GFP Expression. Where indicated LC3-GFP transfected cells, were 12 h after transfection infected with either "Ad.cmv" or "Ad.mda-7", then cultured for 24 h. LC3-GFP transfected cells were visualized at the indicated time points on the Zeiss Axiovert 200 microscope using the FITC filter.

Intra-Cerebral Inoculation of GBM Cells: Athymic female NCr-nu/nu mice (NCI-Fredrick) weighing ~20 g, were used for this study. Mice were maintained under pathogen-free conditions in facilities approved by the American Association for Accreditation of Laboratory Animal Care and in accordance with current regulations and standards of the U.S. Department of Agriculture, Washington, D.C., the U.S. Department of Health and Human Services, Washington, D.C., and the National Institutes of Health, Bethesda, Md. GBM cells were cultured in DMEM supplemented with 5% (v/v) fetal calf serum and 100 µg/ml (1% v/v) penicillin-streptomycin. Cells were incubated in a humidified atmosphere of 5% (v/v) $CO_2$ at 37° C. Mice were anesthetized via i.p. administration of (ketamine, 40 mg/kg; xylazine, 3 mg/kg) and immobilized in a stereotactic frame (KOPF). A 24-gauge needle attached to a Hamilton syringe was inserted into the right basal ganglia to a depth of 3.5-mm and then withdrawn 0.5-mm to make space for tumor cell accumulation. The entry point at the skull was 2-mm lateral and 1-mm dorsal to the bregma. Intra-cerebral injection of $0.5 \times 10^6$ glioma cells (~40 mice per cell line per separate experiment) in 2 µl of DMEM medium was performed over 10 min. The skull opening was enclosed with sterile bone wax and the skin incision was closed using sterile surgical staples. Adenoviral vectors were administered seven days after tumor cell implantation via stereotactic injection into the intra-cerebral tumor using the same anesthesia procedure and stereotactic frame coordinates, as described above. Viral vectors suspended in 2 µl of PBS were delivered by slow infusion over a 6 min period.

Immunohistochemistry and Staining of Fixed Tumor Sections. Post sacrifice, tumors and associated mouse brains were fixed in OCT compound (Tissue Tek); cryostat sectioned (Leica) as 12 µm sections. Nonspecific binding was blocked with a 2% (v/v) Rat Sera, 1% (v/v) Bovine Sera, 0.1% (v/v) Triton X100, 0.05% (v/v) Tween-20 solution then sections were stained for cell signaling pathway markers: For staining of sectioned tumors, primary antibodies were applied overnight, sections washed with phosphate buffer solution, and secondary antibodies applied for detection (as indicated in the Figures): goat anti-rat Alexa 488/647 (1:500; Invitrogen); goat anti-mouse Alexa 488/647 (1:500; Invitrogen) secondary antibody as per the primary antibody used as per the manufacturer's instructions. Sections were then de-hydrated, cleared and mounted with cover-slips using Permount. Apoptotic cells with double stranded DNA breaks were detected using the Upstate TUNEL Apotoic Detection Kit according to the manufacturer's instructions. Slides were applied to high powered light/confocal microscopes (Zeiss LSM 510 Meta-confocal scanning microscope; Zeiss HBO 100 microscope with Axio Cam MRm camera) at the indicated magnification in the Figures/Figure legends. Data shown are representative slides from several sections from the same tumor with multiple tumors (from multiple animals; and multiple experiments) having been examined (n=at least 3-8 animals-tumors).

Data Analysis. Comparison of the effects of various treatments was performed using one way analysis of variance and a two tailed Student's t-test. Differences with a p-value of <0.05 were considered statistically significant. Statistical examination of in vivo animal survival data utilized log rank statistical analyses between the different treatment groups. Experiments shown are the means of multiple individual points from multiple experiments (±SEM).

Results

We determined whether HDACIs enhanced MDA-/IL-24 toxicity in primary human GBM cells. GBM6, GBM12 and primary human astrocytes were infected with empty vector serotype 5 adenovirus (Ad.5-cmv), or a virus to express MDA-7/IL-24 (Ad.5-mda-7). Use of serotype 5 recombinant adenoviruses has been widespread for in vitro use as well as in the clinic. Twelve h after infection cells were treated with increasing doses of the HDACIs, sodium valproate or suberohydroxamic acid (SBHA). In a dose-dependent fashion treatment with HDACIs enhanced the lethality of MDA-7/IL-24 in GBM cells but not in primary human astrocytes (FIGS. 18A-18C). Drug alone, without infection of control virus, was identical to that in control virus infected cells (data not shown). In colony formation assays both valproate and SBHA synergized with MDA-7/IL-24 protein to kill GBM cells (Table 1).

Table 1. MDA-7/IL-24 Synergizes with HDACIs to Kill Primary Human GBM Cells.

GBM6 cells were plated as single cells (500-2,500 per 60-mm dish, in sextuplicate). Twelve h after plating cells were treated with GST or GST-MDA-7 (10-30 nM), SBHA (1-3 µM) or sodium valproate (0.5-1.5 mM), as indicated. Forty-eight h later cells were washed free of drugs and colonies were permitted to form for 20 days. (n=3, +/−SEM). Using the Calcusyn for Windows program we calculated the fraction affected (Fa) and the Combination Index (CI). A CI value of less than 1.00 indicates a synergy of interaction.

| GST-MDA-7 (nM) | SBHA (µM) | Fa | CI | GST-MDA-7 (nM) | Na Val. (mM) | Fa | CI |
|---|---|---|---|---|---|---|---|
| 10 | 1 | 0.36 | 0.55 | 10 | 0.5 | 0.29 | 0.46 |
| 20 | 2 | 0.60 | 0.50 | 20 | 1.0 | 0.40 | 0.46 |
| 30 | 3 | 0.81 | 0.41 | 30 | 1.5 | 0.49 | 0.37 |

Figure 19A:
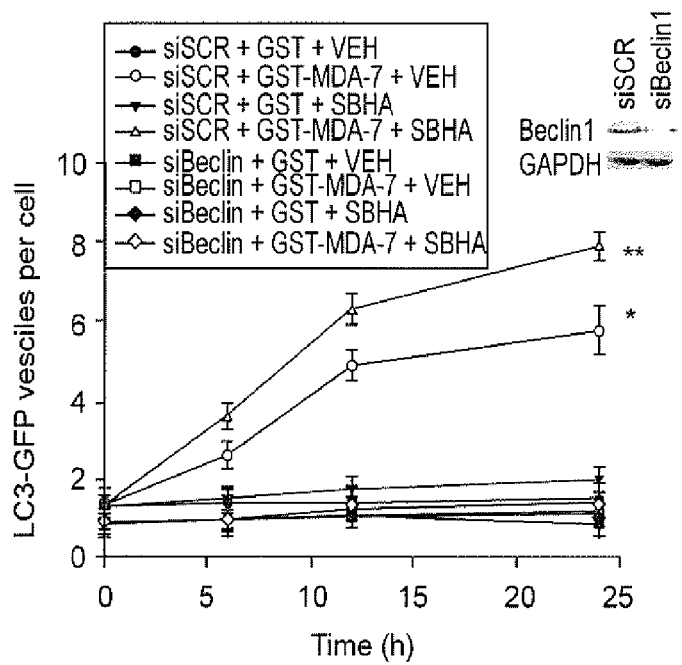
Figure 19B:
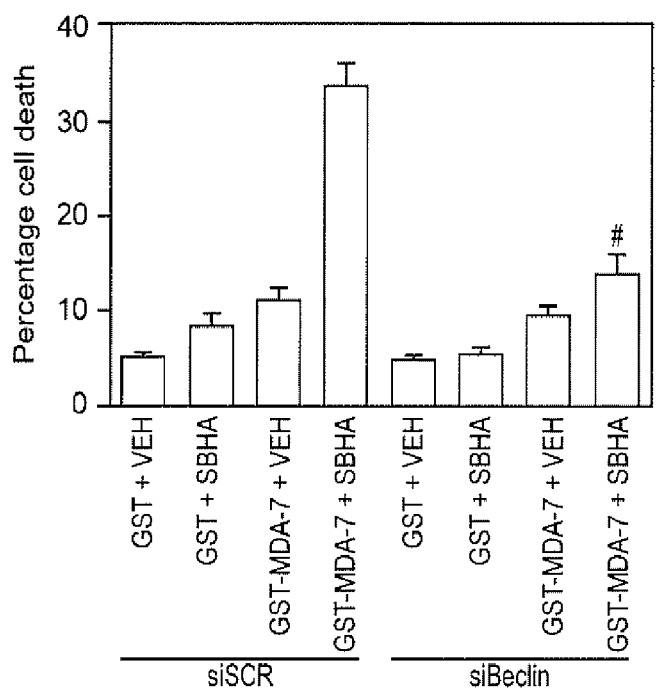

In a time-dependent fashion MDA-7/IL-24 protein increased autophagy (LC3-GFP vesicle) levels in GBM cells (FIG. 2A). SBHA enhanced MDA-7/IL-24 stimulated autophagy levels; knock down of Beclin1 abolished autophagy. Knock down of Beclin1 suppressed both MDA-7/IL-24 and MDA-7/IL-24 plus SBHA toxicity (FIG. 19A-B).

Figure 19C:
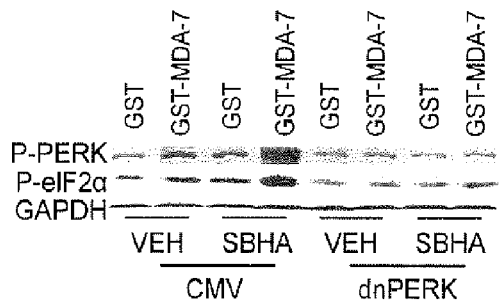
Figure 19D:
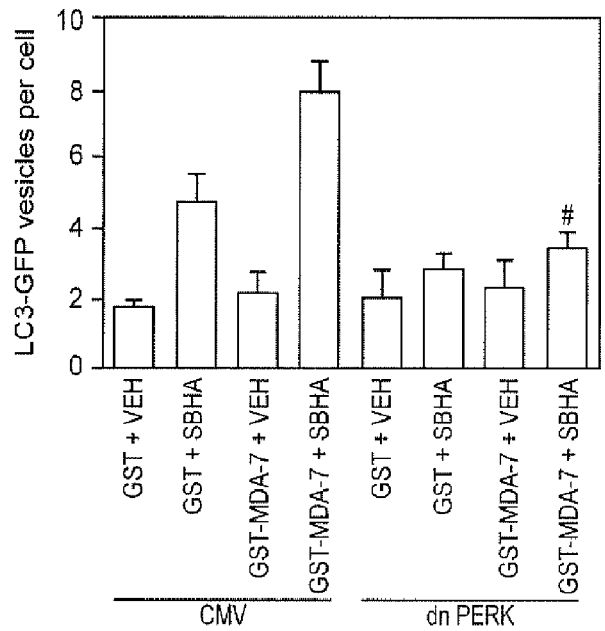

MDA-7/IL-24 protein and SBHA interacted in a greater than additive fashion to activate PKR-like endoplasmic reticulum kinase (PERK) and to increase phosphorylation of the downstream substrate of PERK, eIF2κ (FIG. 19C). Expression of dominant negative PERK suppressed the induction of autophagy and suppressed killing by the combination of agents (FIG. 19D and FIG. 20).

Ceramide generation plays a key role in MDA-7/IL-24 lethality, with activation of the de novo ceramide synthesis pathway (ceramide synthase 6 (LASS6)) playing a key role in MDA-7/IL-24-induced ROS levels and changes in cytosolic $Ca^{2+}$ (Yacoub et al, 2010a). Knock down of LASS6 expression suppressed the induction of autophagy in GBM cells and suppressed killing by the combination of Ad.5-mda-7 and SBHA (FIGS. 21A and 21B).

We next determined the roles of ROS and changes in cytosolic $Ca^{2+}$ in the response of GBM cells to MDA-7/IL-24 and HDACIs. Ad.5-mda-7 and SBHA interacted in a greater than additive fashion to increase ROS and $Ca^{2+}$ levels (FIGS. 22A and 22B). HDACI treatment: (1) increased the initial Ad.5-mda-7-induced ROS and $Ca^{2+}$ levels; and (2) prolonged the increase in ROS and $Ca^{2+}$ signaling. Quenching of ROS expressing thioredoxin (TRX) or quenching of $Ca^{2+}$ using calbindin suppressed MDA-7/IL-24 and MDA-7/IL-24 plus SBHA toxicity (FIG. 22C).

GBM cells were infected to express c-FLIP-s and CRM A (inhibitors of the extrinsic apoptosis pathway) or infected to express BCL-XL and dominant negative caspase 9 (inhibitors of the intrinsic apoptosis pathway). Expression of c-FLIP-s or CRM A did not alter MDA-7/IL-24 toxicity as a single agent (FIG. 23A). However, expression of c-FLIP-s or CRM A suppressed the ability of SBHA to enhance MDA-7/IL-24 toxicity. Expression of BCL-XL or dominant negative caspase 9 suppressed MDA-7/IL-24 and MDA-7/

Figure 23B:
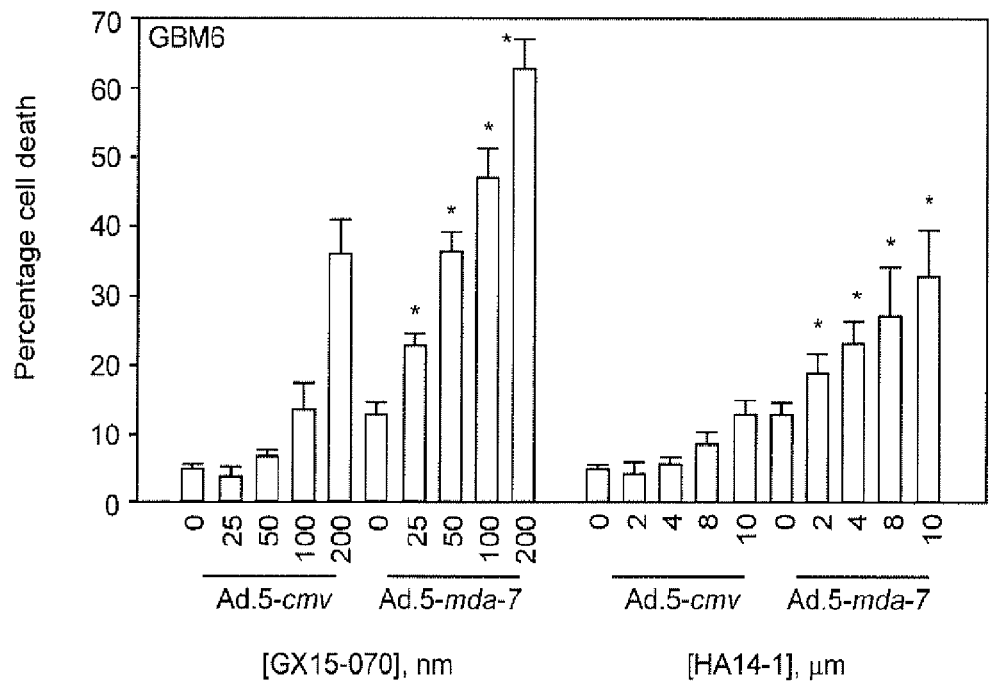

IL-24 plus SBHA toxicity. We determined whether inhibitors of protective BCL-2 family proteins enhanced killing by MDA-7/IL-24. Treatment of GBM cells with either the BCL-2/BCL-XL/MCL-1 inhibitor obatoclax or the BCL-2/BCL-XL inhibitor HA14-1 enhanced the lethality of Ad.5-mda-7 (FIG. 23B). These data are similar to prior studies in prostate cancer cells using the BCL-2 family inhibitor sabutoclax (Azab et al, 2012; Dash et al, 2011).

We developed a tropism modified recombinant adenovirus to express MDA-7/IL-24 that comprises the tail and shaft domains of a serotype 5 adenovirus and the knob domain of a serotype 3 virus (Dash et al, 2010, Hamed et al, 2010). We have published that Ad.5/3-mda-7 prolonged the survival of animals carrying GBM tumors to a greater extent than did Ad.5-mda-7 (Hamed et al, 2010). GBM cells were implanted into the brains of athymic mice and tumors infused with virus. In agreement with our prior publications, infusion of tumors with Ad.5/3-mda-7 prolonged animal survival (FIG. 24). Treatment of animals with SAHA did not significantly enhance animal survival. Combined treatment with Ad.5/3-mda-7 and SAHA prolonged survival to a significantly greater extent than Ad.5.3-mda-7 alone. Collectively our data argue that HDACIs and MDA-7/IL-24 interact to kill GBM cells in vitro and in vivo.

Figure 25A:
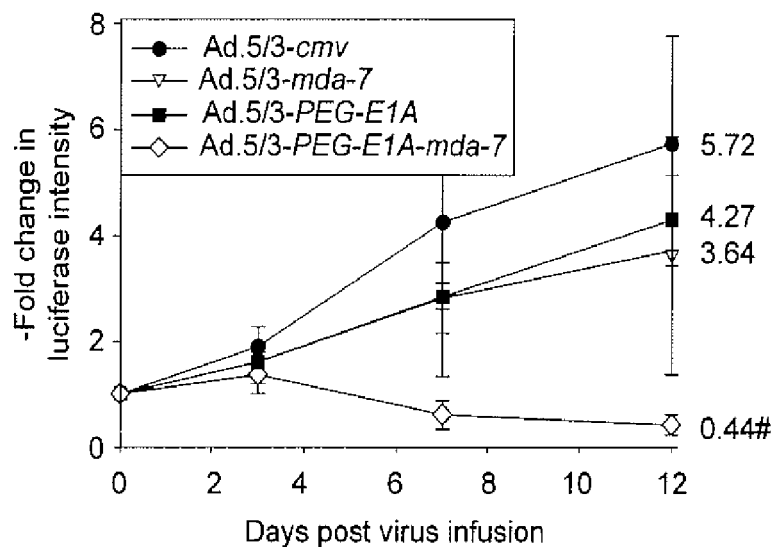

In parallel studies we generated a serotype 5/serotype 3 recombinant adenovirus to express MDA-7/IL-24 that also conditionally replicates only in tumor cells (Ad.5/3-PEG-E1A-mda-7; also termed in the Figures as Ad.5/3-CTV; Ad.5/3-CTV-M7) (see also Sarkar et al, 2007; Sarkar et al, 2008). We compared the growth suppressive effects of Ad.5/3-mda-7 and Ad.5/3-PEG-E1A-mda-7 (Ad.5/3-CTV; Ad.5/3-CTV-M7) following infection of orthotopic GBM tumors. GBM6 cells stably transfected to express luciferase were implanted into athymic nude mouse brains. Seven days after implantation mice received a single low dose intra-tumor infusion of recombinant adenovirus. The viruses infused were: Ad.5/3-cmv (empty vector control, non-replicative); Ad.5/3-PEG-E1A (empty vector control, tumor selective replication); Ad.5/3-mda-7 (MDA-7/IL-24 expression, non-replicative); Ad.5/3-PEG-E1A-mda-7 (Ad.5/3-CTV; Ad.5/3-CTV-M7; MDA-7/IL-24 expression, tumor selective replication). Although a trend was evident, at the low doses of virus used in this study neither Ad.5/3-PEG-E1A nor Ad.5/3-mda-7 caused a significant decrease in tumor luminosity using a Xenogen IVIS system, i.e., tumor growth (FIG. 25A). However, infusion of Ad.5/3-PEG-E1A-mda-7 (Ad.5/3-CTV; Ad.5/3-CTV-M7) resulted in a significant suppression of tumor mass below the initial value.

Figure 25B:
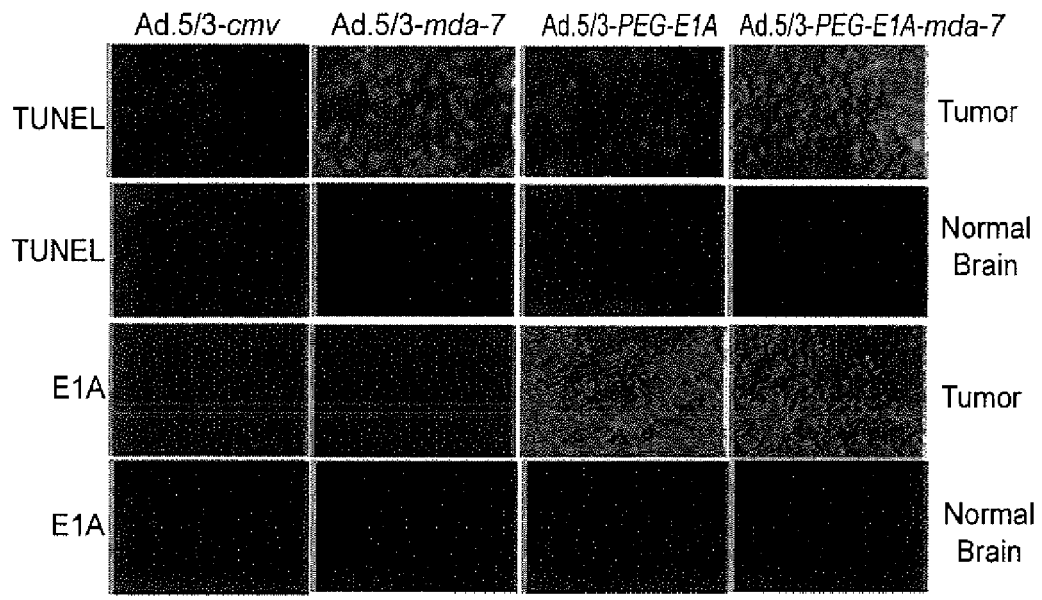

Animals carrying GBM6-luc tumors were sacrificed, their brains isolated, and immuno-histochemistry performed on the GBM6 tumors within brain sections. Ad.5/3-PEG-E1A caused a modest enhancement in apoptosis/TUNEL positivity in the tumor, an effect which was considerably greater in Ad.5/3-mda-7 infected tumors (FIG. 25B). Ad.5/3-PEG-E1A-mda-7 (Ad.5/3-CTV-M7)-infected tumors had greater levels of TUNEL positivity than Ad.5/3-mda-7 infected tumors. In sections of normal brain no TUNEL staining was evident. Infection of tumors with Ad.5/3-PEG-E1A or Ad.5/3-PEG-E1A-mda-7 (Ad.5/3-CTV-M7) increased E1A immunoreactivity in tumor sections but not in sections of normal brain. This would suggest viral replication and cell killing by Ad.5/3-PEG-E1A-mda-7 (Ad.5/3-CTV-M7) is restricted to tumor tissue.

Figure 25C:
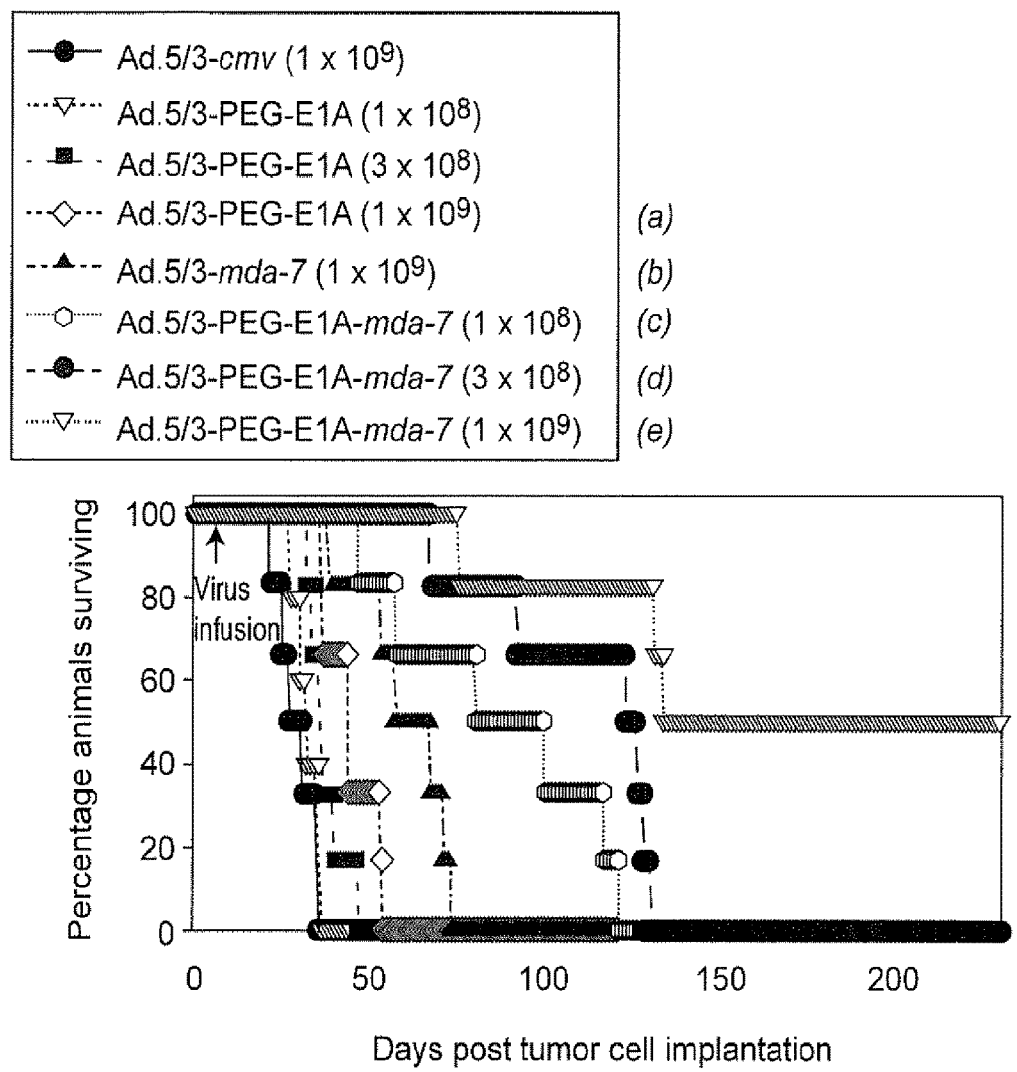
Figure 25D:
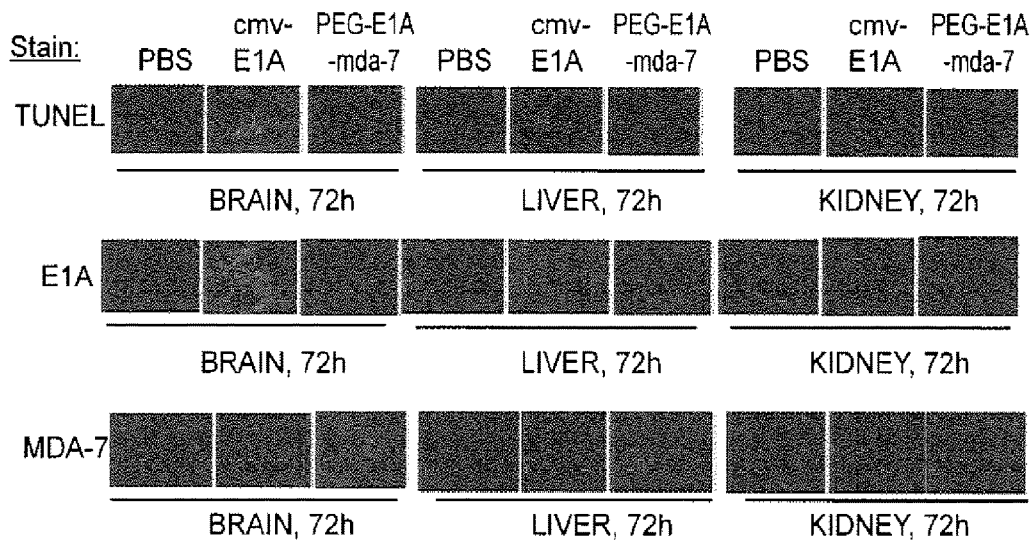
Figure 25E:
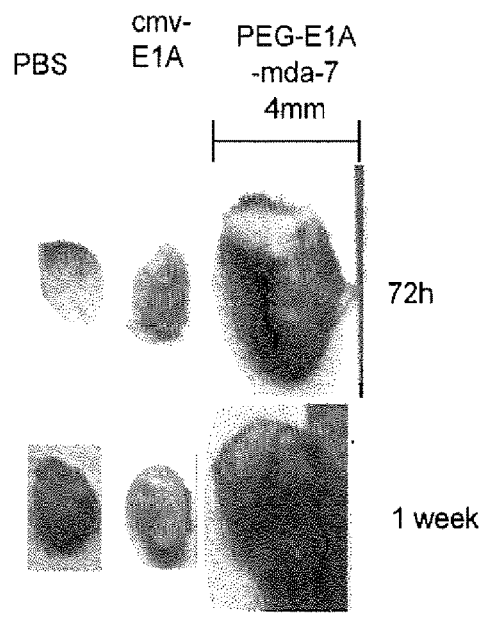

We next determined using different doses of adenovirus whether Ad.5/3-PEG-E1A-mda-7 (Ad.5/3-CTV-M7) was a more efficacious virus at prolonging animal survival when compared to Ad.5/3-PEG-E1A or Ad.5/3-mda-7. At the lowest dose of Ad.5/3-PEG-E1A-mda-7 (Ad.5/3-CTV-M7) tested ($1\times10^8$ plaque forming units (pfu)), the virus prolonged survival to a greater extent than did infusion of $1\times10^9$ pfu of Ad.5/3-mda-7 (FIG. 25C). The intermediate dose of Ad.5/3-PEG-E1A-mda-7 (Ad.5/3-CTV-M7) tested ($3\times10^8$ pfu) prolonged survival to a greater extent than did infusion of $1\times10^8$ pfu of the same virus. Accordingly, infusion of $1\times10^9$ pfu of Ad.5/3-PEG-E1A-mda-7 (Ad.5/3-CTV-M7) prolonged survival to a greater extent than did infusion of $3\times10^8$ pfu of the same virus, with some animals living for >250 days. As Ad.5/3-PEG-E1A-mda-7 (Ad.5/3-CTV-M7) prolonged animal survival we performed preliminary toxicology testing of this virus in preparation for its translation into the clinic. Syrian hamsters are an FDA approved model for oncolytic adenovirus toxicology testing; they are immuno-competent and they permit human adenovirus replication in normal tissues (Curiel and Fisher, 2012; Dhar et al, 2012). Hamster brains were infused with PBS, an adenovirus that constitutively replicates Ad.5/3-cmv-E1A ($3\times10^9$ pfu), or Ad.5/3-PEG-E1A-mda-7 (Ad.5/3-CTV-M7) ($3\times10^9$ pfu). Infusion of Ad.5/3-cmv-E1A strongly increased the levels of TUNEL positivity and expression of the viral protein E1A in hamster brains (FIG. 25D). Low levels of TUNEL positivity and E1A staining were also evident in the livers of animals who had been infused with Ad.5/3-cmv-E1A; no staining of the kidneys was observed. In contrast, infection of hamster brains with Ad.5/3-PEG-E1A-mda-7 (Ad.5/3-CTV-M7) did not increase TUNEL positivity or E1A levels. Staining for MDA-7/IL-24 protein was evident in Ad.5/3-PEG-E1A-mda-7 infected brains. During our studies we noted that animals infused with Ad.5/3-cmv-E1A had enlarged neck lymph nodes, indicative that this virus was generating an immune response (FIG. 25E). In contrast, the lymph nodes of animals infused with PBS or with Ad.5/3-PEG-E1A-mda-7 (Ad.5/3-CTV-M7) looked identical (and small).

Collectively our in vivo data with Ad.5/3-PEG-E1A-mda-7 (Ad.5/3-CTV-M7) indicate that the virus significantly prolongs animal survival and has an apparent safe toxicology profile in Syrian hamsters.

Discussion

The research described in this Example 3 has focused on developing novel therapies for GBM. To achieve these objectives, we utilized mda-7/IL-24, which has demonstrated tumor cell-specific killing and radiosensitization of glioma cells (Yacoub et al, 2010a; Yacoub et al, 2008a; Yacoub et al, 2008b; Yacoub et al, 2008c). Prior studies have shown that inhibition of signaling pathways can enhance MDA-7/IL-24 toxicity in GBM cells and the present analyses extended our combinatorial approaches targeting histone deacetylases (Yacoub et al, 2008b; Hamed et al, 2010). We show that HDACIs increase MDA-7/IL-24 toxicity and we also identify a means of enhancing the therapeutic delivery of MDA-7/IL-24 for GBM using a tropism-modified serotype 5/3 adenovirus that conditionally replicates in tumor cells. We are in the advanced stages of preparation of a Phase I trial dose-limiting toxicity trial using Ad.5/3-PEG-E1A-mda-7 (Ad.5/3-CTV-M7). In preferred embodiments in GBM, a combination of virotherapy and either HDAC inhibitors or, radiotherapy, may be employed.

HDACIs cause oxidative damage to cells which contributes to their lethality, and possibly to the selectivity of these compounds for tumor cells (Ruefli et al, 2001; Ungerstedt et al, 2005). Our data demonstrated using Ad.5-mda-7 or MDA-7/IL-24 protein in GBM isolates treated with several HDACIs that the combination of agents synergized to kill GBM cells. Both MDA-7/IL-24 and HDACIs increased the levels of ROS and when combined they further enhanced and prolonged ROS generation. Quenching of ROS suppressed the toxic interaction between the agents. In GBM cells, MDA-7/IL-24 toxicity has been associated with activation of PERK and the induction of autophagy (Yacoub et al, 2010a, Yacoub et al, 2008a; Hamed et al, 2010). HDACIs enhanced both MDA-7/IL-24-induced activation of PERK and the increase in autophagy levels. HDACIs as single agents are known to cause an ER stress response that has been linked to acetylation of GRP78/BiP (Kahali et al, 2010): one portion of the mechanism by which MDA-7/IL-24 induces ER stress is through binding to GRP78/BiP (Gupta et al, 2006). Expression of dominant negative PERK or knock down of Beclin1 blocked the increase in autophagy levels and the toxic interaction between MDA-7/IL-24 and HDACIs. HDACIs down-regulate c-FLIP-s levels and to increase the levels of death receptors (Emanuele et al, 2007). Inhibition of the extrinsic pathway did not block MDA-7/IL-24 toxicity however inhibition of this pathway blunted the interaction between MDA-7/IL-24 and HDACIs. We have previously shown in renal and ovarian cancer cells that MDA-7/IL-24 lethality is dependent on death receptor signaling (Park et al, 2009; Yacoub et al, 2010b). Inhibition of the intrinsic pathway blocked both MDA-7/IL-24 and HDACI lethality.

Several HDACIs can cross the blood-brain barrier including sodium valproate and vorinostat (Friday et al, 2012). In vivo we noted in mice carrying GBM tumors that Ad.5/3-mda-7 prolonged animal survival and that this effect was augmented by HDACI treatment. There have been multiple Phase I and Phase II trials of HDACIs in glioma patients (Friday et al, 2012; Lee et al, 2012; Galanis et al, 2009; Chinnaiyan et al, 2012). Alone, although well tolerated by patients vorinostat has modest single agent activity in GBM, which is in agreement with our findings. Vorinostat has been combined with ionizing radiation, temozolomide, bortezomib and bevacizumab and CPT-11 in GBM patients, with some partial responses evident (Friday et al, 2012; Lee et al, 2012; Galanis et al, 2009; Chinnaiyan et al, 2012).

GBM was one of the earliest malignancies considered amenable to viral delivery of genetic-based therapeutics (Curiel and Fisher, 2012). Serotype 5 adenoviruses infect through the CAR, a protein whose expression is reduced in GBM cells (Curiel and Fisher, 2012; Paul et al, 2008; Dash et al, 2010; Hamed et al, 2010). This has resulted in groups using targeting strategies to enhance viral infectivity via CAR-independent pathways. Several laboratories have modified the infective viral capsid "knob" to bind surface integrin proteins (an RGD modification) or by insertion into the knob of multiple lysine residues (a pK7 modification) that permit virus attachment to cells through an electrostatic interactions (Curiel and Fisher, 2012). We have taken the infective capsid knob from a serotype 3 adenovirus and incorporated it into the adenovirus type 5 knob; we demonstrated that modified serotype 5/3 knob adenoviruses were able to achieve enhanced gene transduction into low- and high-CAR containing human GBM tumor cells (Curiel and Fisher, 2012; Paul et al, 2008; Hamed et al, 2010). We noted that a serotype 5/3 virus was more efficient at transducing genes into GBM cells than either an RGD/double RGD modification or a pK7 modification (Curiel and Fisher, 2012; Hamed et al, 2010).

GBM is a highly invasive and diffuse tumor, which will make infection of every tumor cell a difficult and probably an impossible proposition when using a non-replicative adenovirus. Many prior studies in GBM have used serotype 5 viruses, which as mentioned previously, have reduced infectivity in CAR low GBM cells in situ. In addition to these limitations, prior gene therapy studies in GBM have also frequently expressed intracellular proteins, e.g. p53, which will result in only those cells that have been virally infected being subjected to the actions of the therapeutic gene, i.e., these infections lack a "bystander" secreted protein effect on uninfected tumor cells (Fisher, 2005; Dash et al, 2010; Curiel and Fisher, 2012; Hamed et al, 2010; Sauane et al, 2008). In GBM tumors growing on the flanks of mice Ad.5/3-mda-7 therapy suppressed the growth not only of the tumor into which it was injected but also suppressed growth of the tumor on the opposite flank (i.e., the un-infected tumor). Thus, consistent with other cancer indications, Ad.5/3-mda-7 generates a "bystander effect" in the contralateral uninfused GBM tumor (Hamed, Fisher and Dent, unpublished observations) (Sauane et al, 2008; Park et al, 2009). Collectively these constraints may explain the relative lack of efficacy of previous gene therapy approaches in GBM.

The use of Ad.5/3-PEG-E1A-mda-7 (Ad.5/3-CTV; Ad.5/3-CTV-M7) is one approach to overcome the issues of infectivity and the diffuse nature of GBM. Ad.5/3-PEG-E1A-mda-7 (Ad.5/3-CTV-M7) efficiently infects low CAR GBM cells and enhances infectivity even in CAR high GBM cells (Hamed et al, 2010). Ad.5/3-PEG-E1A-mda-7 replicates selectively in tumor cells which can result in virus dissemination within the brain to infect tumor cells centimeters away from the site of virus administration. MDA-7/IL-24 protein is secreted from infected GBM cells and astrocytes and as we have recently demonstrated in both GBM, renal and prostate cancer cells media containing secreted MDA-7/IL-24 can induce apoptosis in uninfected tumor cells (Yacoub et al, 2010a; Curiel and Fisher, 2012; Sauane et al, 2008; Park et al, 2009). MDA-7/IL-24 can induce its own synthesis in tumor cells, amplifying the initial effect of viral infection/the initial MDA-7/IL-24 secretion (Curiel and Fisher, 2012; Sauane et al, 2008; Park et al, 2009). Thus, the expression of MDA-7/IL-24 overcomes the problems associated with a lack of a "bystander" effect following gene therapeutic intervention.

In a dose-dependent fashion Ad.5/3-PEG-E1A-mda-7 (Ad.5/3-CTV-M7) increased animal survival when compared to Ad.5/3-mda-7. At the highest virus dose tested Ad.5/3-PEG-E1A-mda-7 (Ad.5/3-CTV-M7) prolonged the survival of some animals to >250 days. No change in animal behavior or body mass was noted with these interventions. This data argues that Ad.5/3-PEG-E1A-mda-7 (Ad.5/3-CTV-M7) is a safe and efficacious virus for the treatment of animal GBM models. Based on these findings, as suggested to us by the FDA, we performed preliminary toxicology testing using an approved rodent model for human adenovirus replication, the Syrian hamster (Curiel and Fisher, 2012; Dhar et al, 2012). Infusion into the hamster brain of a constitutively replicating adenovirus Ad.5/3-cmv-E1A resulted in significant levels of apoptosis and expression of the viral protein E1A; thus viral replication had occurred. The liver is a major site of adenovirus clearance from the blood, and following infusion of this virus into the brain we noted low levels of apoptosis and E1A expression in the liver. The kidneys did not exhibit any virus uptake. Infusion into the brain of Ad.5/3-PEG-E1A-mda-7 (Ad.5/3-CTV-M7) did not result in apoptosis or expression of the viral E1A protein. This argues that control of virus replication by the PEG-3 promoter was tumor cell specific. Syrian hamsters are an immune-competent model and would be expected to immunologically respond to virus replication (Curiel and Fisher, 2012; Dhar et al, 2012). In agreement with this hypothesis we found that neck lymph nodes were enlarged in Ad.5/3-cmv-E1A infected animals, whereas infusion of Ad.5/3-PEG-E1A-mda-7 had no obvious effect on lymph node size. These findings further demonstrate that Ad.5/3-PEG-E1A-mda-7 (Ad.5/3-CTV-M7) is a safe and efficacious virus in vivo.

Our data demonstrate that HDACIs increase MDA-7/IL-24 lethality through mechanisms involving ER stress and activation of the extrinsic apoptosis pathway. Adenoviral delivery of mda-7/IL-24 to GBM cells and tumors can be enhanced by a serotype 3 tropism modification and by engineering of the virus to conditionally replicate in tumor cells.

References For Example 3

Azab B, Dash R, Das S K, Bhutia S K, Shen X N, Quinn B A, et al. (2012) Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells. *J Cell Physiol*. 227: 2145-2153.

Bhutia S K, Das S K, Azab B, Dash R, Su Z Z, Lee S G, et al. (2011) Autophagy switches to apoptosis in prostate cancer cells infected with melanoma differentiation associated gene-7/interleukin-24 (mda-7/IL-24). *Autophagy*. 7: 1076-1077.

Chinnaiyan P, Chowdhary S, Potthast L, Prabhu A, Tsai Y Y, Sarcar B, et al. (2012) Phase I trial of vorinostat combined with bevacizumab and CPT-11 in recurrent glioblastoma. *Neuro Oncol*. 14: 93-100.

Cunningham C C, Chada S, Merritt J A, Tong A, Senzer N, Zhang Y, et al. (2005) Clinical and local biological effects of an intratumoral injection of mda-7 (IL24; INGN 241) in patients with advanced carcinoma: a phase I study. *Mol Ther* 11: 149-159.

Curiel D T, Fisher P B. (Eds.) (2012) Applications of Viruses for Cancer Therapy. *Adv Cancer Res*. 115: 1-334.

Dai Y, Rahmani M, Dent P, Grant S. (2005) Blockade of histone deacetylase inhibitor-induced RelA/p65 acetylation and NF-kappaB activation potentiates apoptosis in leukemia cells through a process mediated by oxidative damage, XIAP downregulation, and c-Jun N-terminal kinase 1 activation. *Mol Cell Biol*. 25: 5429-5444.

Dash R, Bhutia S K, Azab B, Su Z Z, Quinn B A, Kegelmen T P, et al. (2010) mda-7/IL-24: a unique member of the IL-10 gene family promoting cancer-targeted toxicity. *Cytokine Growth Factor Rev*. 21: 381-391.

Dash R, Azab B, Quinn B A, Shen X, Wang X Y, Das S K, et al. (2011) Apogossypol derivative BI-97C1 (Sabutoclax) targeting Mcl-1 sensitizes prostate cancer cells to mda-7/IL-24-mediated toxicity. *Proc Natl Acad Sci USA*. 108: 8785-8790.

Dash R, Dmitriev I, Su Z Z, Bhutia S K, Azab B, Vozhilla N, et al. (2010) Enhanced delivery of mda-7/IL-24 using a serotype chimeric adenovirus (Ad.5/3) improves therapeutic efficacy in low CAR prostate cancer cells. *Cancer Gene Ther*. 17: 447-456.

Dhar D, Toth K, Wold W S. (2012) Syrian hamster tumor model to study oncolytic Ad5-based vectors. *Methods Mol Biol*. 797:53-63.

Dent P, Yacoub A, Hamed H A, Park M A, Dash R, Bhutia S K, et al. (2010a) The development of MDA-7/IL-24 as a cancer therapeutic. *Pharmacol Ther*. 128: 375-384.

Dent P, Yacoub A, Hamed H A, Park M A, Dash R, Bhutia S K, et al. (2010b) MDA-7/IL-24 as a cancer therapeutic: from bench to bedside. *Anticancer Drugs*. 21: 725-731.

Ekmekcioglu S, Ellerhorst J, Mhashilkar A M, Sahin A A, Read C M, Prieto V G, et al. (2001) Down-regulated melanoma differentiation associated gene (mda-7) expression in human melanomas. *Int J Cancer* 94: 54-59.

Ellerhorst J A, Prieto V G, Ekmekcioglu S, Broemeling L, Yekell S, Chada S, et al. (2002) Loss of MDA-7 expression with progression of melanoma. *J Clin Oncol* 20: 1069-1074.

Ellis L, Pili R. (2010) Histone Deacetylase Inhibitors: Advancing Therapeutic Strategies in Hematological and Solid Malignancies. *Pharmaceuticals (Basel)* 3: 2411-69.

Emanuele S, Lauricella M, Carlisi D, Vassallo B, D'Anneo A, Di Fazio P, et al. (2007) SAHA induces apoptosis in hepatoma cells and synergistically interacts with the proteasome inhibitor Bortezomib. *Apoptosis*. 12: 1327-1338.

Emdad L, Lebedeva I V, Su Z Z, Gupta P, Sauane M, Dash R, et al. (2009) Historical perspective and recent insights into our understanding of the molecular and biochemical basis of the antitumor properties of mda-7/IL-24. *Cancer Biol Ther*. 8: 391-400.

Fisher P B, Gopalkrishnan R V, Chada S, Chada S, Ramesh R, Grimm E A, et al. (2003) mda-7/IL-24, a novel cancer selective apoptosis inducing cytokine gene: from the laboratory into the clinic. *Cancer Biol Ther* 2: S23-37.

Fisher P B. (2005) Is mda-7/IL-24 a "magic bullet" for cancer? *Cancer Res* 65: 10128-10138.

Frew A J, Johnstone R W, Bolden J E. (2009) Enhancing the apoptotic and therapeutic effects of HDAC inhibitors. *Cancer Lett* 280: 125-33.

Friday B B, Anderson S K, Buckner J, Yu C, Giannini C, Geoffroy F, et al. (2012) Phase II trial of vorinostat in combination with bortezomib in recurrent glioblastoma: a north central cancer treatment group study. *Neuro Oncol*. 14:215-221.

Galanis E, Jaeckle K A, Maurer M J, Reid J M, Ames M M, Hardwick J S, et al. (2009) Phase II trial of vorinostat in recurrent glioblastoma multiforme: a north central cancer treatment group study. *J Clin Oncol*. 27: 2052-2058.

Gupta P, Su Z Z, Lebedeva I V, Sarkar D, Sauane M, Emdad L, et al. (2006) mda-7/IL-24: multifunctional cancer-specific apoptosis-inducing cytokine. *Pharmacol Ther* 111: 596-628.

Gupta P, Walter M R, Su Z Z, Lebedeva I V, Emdad L, Randolph A, et al. (2006) BiP/GRP78 is an intracellular target for MDA-7/IL-24 induction of cancer-specific apoptosis. *Cancer Res*. 66: 8182-8191.

Hamed H A, Yacoub A, Park M A, Eulitt P J, Dash R, Sarkar D, et al. (2010) Inhibition of multiple protective signaling pathways and Ad.5/3 delivery enhances mda-7/IL-24 therapy of malignant glioma. *Mol Ther*. 18: 1130-1142.

Jiang H, Lin J J, Su Z Z, Goldstein, N I, Fisher, P B. (1995) Subtraction hybridization identifies a novel melanoma differentiation associated gene, mda-7, modulated during human melanoma differentiation, growth and progression. *Oncogene* 11: 2477-2486.

Kahali S, Sarcar B, Fang B, Williams E S, Koomen J M, Tofilon P J, et al. (2010) Activation of the unfolded protein response contributes toward the antitumor activity of vorinostat. *Neoplasia*. 12: 80-86.

Lebedeva I V, Sauane M, Gopalkrishnan R V, Sarkar D, Su Z Z, Gupta P, et al. (2005) mda-7/IL-24: exploiting cancer's Achilles' heel. *Mol Ther* 11: 4-18.

Lee E Q, Puduvalli V K, Reid J M, Kuhn J G, Lamborn K R, Cloughesy T F, et al. (2012) Phase I study of vorinostat in combination with temozolomide in patients with high-grade gliomas: North American Brain Tumor Consortium Study 04-03. *Clin Cancer Res*. 18: 6032-6039.

Park M A, Walker T, Martin A P, Allegood J, Vozhilla N, Emdad L, et al. (2009) MDA-7/IL-24-induced cell killing in malignant renal carcinoma cells occurs by a ceramide/CD95/PERK-dependent mechanism. Mol Cancer Ther. 8: 1280-1291.

Paul C P, Everts M, Glasgow J N, Dent P, Fisher P B, Ulasov I V, et al. (2008) Characterization of infectivity of knob-modified adenoviral vectors in glioma. Cancer Biol Ther. 7: 786-793.

Robins H I, Chang S, Butowski N, Mehta M. (2007) Therapeutic advances for glioblastoma multiforme: current status and future prospects. Curr Oncol Rep 9: 66-70.

Rosato R R and Grant S. (2004) Histone deacetylase inhibitors in clinical development. Expert Opin Investig Drugs 13: 21-38.

Ruefli A A, Ausserlechner M J, Bernhard D, Sutton V R, Tainton K M, Kofler R, et al. (2001) The histone deacetylase inhibitor and chemotherapeutic agent suberoylanilide hydroxamic acid (SAHA) induces a cell-death pathway characterized by cleavage of Bid and production of reactive oxygen species. Proc Natl Acad Sci USA. 98: 10833-10838.

Sarkar D, Lebedeva I V, Su Z Z, Park E S, Chatman L, Vozhilla N, et al. (2007) Eradication of therapy-resistant human prostate tumors using a cancer terminator virus. Cancer Res. 67: 5434-5442.

Sarkar D, Su Z Z, Park E S, Vozhilla N, Dent P, Curiel D T, et al. (2008) A cancer terminator virus eradicates both primary and distant human melanomas. Cancer Gene Ther. 15: 293-302.

Sarkar D, Su Z-z, Vozhilla N, Park E S, Gupta P, Fisher P B. (2005) Dual cancer-specific targeting strategy cures primary and distant breast carcinomas in nude mice. Proc Natl Acad Sci USA. 102: 14034-14039.

Sauane M, Su Z Z, Dash R, Liu X, Norris J S, Sarkar D, et al. (2010) Ceramide plays a prominent role in MDA-7/IL-24-induced cancer-specific apoptosis. J Cell Physiol. 222: 546-555.

Sauane M, Su Z Z, Gupta P, Lebedeva I V, Dent P, Sarkar D, et al. (2008) Autocrine regulation of mda-7/IL-24 mediates cancer-specific apoptosis. Proc Natl Acad Sci USA. 105: 9763-9768.

Spiegel S, Milstien S, Grant S. (2012) Endogenous modulators and pharmacological inhibitors of histone deacetylases in cancer therapy. Oncogene. 31: 537-551.

Su Z, Lebedeva I V, Gopalkrishnan R V, Goldstein N I, Stein C A, Reed J C, et al. (2001) A combinatorial approach for selectively inducing programmed cell death in human pancreatic cancer cells. Proc Natl Acad Sci USA 98: 10332-10337.

Su Z Z, Madireddi M T, Lin J J, Young C S, Kitada S, Reed J C, et al. (1998) The cancer growth suppressor gene mda-7 selectively induces apoptosis in human breast cancer cells and inhibits tumor growth in nude mice. Proc Natl Acad Sci USA 95: 14400-14405.

Su Z Z, Sarkar D, Emdad L, Duigou G J, Young C S, Ware J, et al. (2005) Targeting gene expression selectively in cancer cells by using the progression-elevated gene-3 promoter. Proc Natl Acad Sci USA. 102: 1059-1064.

Tang Y, Yacoub A, Hamed H A, Poklepovic A, Tye G, Grant S, et al. (2012) Sorafenib and HDAC inhibitors synergize to kill CNS tumor cells. Cancer Biol Ther. 13: 567-574.

Ungerstedt J S, Sowa Y, Xu W S, Shao Y, Dokmanovic M, Perez G, et al. (2005) Role of thioredoxin in the response of normal and transformed cells to histone deacetylase inhibitors. Proc Natl Acad Sci USA. 102: 673-678.

Yacoub A, Hamed H A, Allegood J, Mitchell C, Spiegel S, Lesniak M S, et al. (2010a) PERK-dependent regulation of ceramide synthase 6 and thioredoxin play a key role in mda-7/IL-24-induced killing of primary human glioblastoma multiforme cells. Cancer Res. 70: 1120-1129.

Yacoub A, Park M A, Gupta P, Rahmani M, Zhang G, Hamed H, et al. (2008a) Caspase, cathepsin-, and PERK-dependent regulation of MDA-7/IL-24-induced cell killing in primary human glioma cells. Mol Cancer Ther. 7: 297-313.

Yacoub A, Gupta P, Park M A, Rhamani M, Hamed H, Hanna D, et al. (2008b) Regulation of GST-MDA-7 toxicity in human glioblastoma cells by ERBB1, ERK1/2, PI3K, and JNK1-3 pathway signaling. Mol Cancer Ther. 7: 314-329.

Yacoub A, Hamed H, Emdad L, Dos Santos W, Gupta P, Broaddus W C, et al. (2008c) MDA-7/IL-24 plus radiation enhance survival in animals with intracranial primary human GBM tumors. Cancer Biol Ther. 7: 917-933.

Yacoub A, Liu R, Park M A, Hamed H A, Dash R, Schramm D N, et al. (2010b) Cisplatin enhances protein kinase R-like endoplasmic reticulum kinase- and CD95-dependent melanoma differentiation-associated gene-7/interleukin-24-induced killing in ovarian carcinoma cells. Mol Pharmacol. 77: 298-310.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

We claim:

1. A method of treating cancer in a subject in need thereof, comprising administering to the subject a therapeutically effective amount of composition comprising a cancer terminator virus (CTV) comprising an adenovirus serotype 5/serotype 3 chimera (Ad.5/3), wherein (i) the virus expresses melanoma differentiation associated gene-7/interleukin-24 (mda-7/IL-24); (ii) viral replication is under control of the Progression Elevated Gene (PEG)-3 promoter; and (iii) the cancer is a prostate cancer, a pancreatic cancer, or a glioblastoma.

2. The method of claim 1 wherein said administering is performed systemically.

3. The method of claim 2 wherein said virus is encapsulated in microbubbles in a physiologically acceptable carrier.

4. The method of claim 1, further comprising administering to the patient at least one additional therapeutic agent.

5. The method of claim 4 wherein said at least one additional therapeutic agent is selected from the group consisting of agents that augment reactive oxygen (ROS) production, HDAC inhibitors, MCL-1 inhibitors, and Bcl-2/Bcl-xL inhibitors.

6. The method of claim 1 wherein said cancer is a low-Coxsackie-Adeno virus Receptor (CAR) cancer.

7. The method of claim 1, wherein the cancer is a pancreatic cancer.

8. The method of claim 7, further comprising administering perillyl alcohol to the subject.

9. The method of claim 1, wherein the cancer is a glioblastoma.

10. The method of claim 9, further comprising administering an HDAC inhibitor to the subject.

11. The method of claim 1, wherein said cancer is a prostate cancer.

12. The method of claim 11, further comprising administering an MCL-1 inhibitor to the subject.

13. The method of claim 1, wherein said cancer is a high-Coxsackie-Adeno virus Receptor (CAR) cancer.

14. The method of claim 4, wherein said at least one additional therapeutic agent is selected from the group consisting of perillyl alcohol, an HDAC inhibitor, and an MCL-1 inhibitor.

* * * * *

SEQUENCE LISTING

<160> NUMBER OF SEQ ID NOS: 6

<210> SEQ ID NO 1
<211> LENGTH: 961
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120

```
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tatttgtcta gggagatctc      360
agagaggaga gagaaagaga aagagaatgg gacagcatgt gactgcctga tgaagttggc      420
gtgcttgctc aaaagttctg cgagattgac ggctctctgg atttgagcca aggacacgcc      480
tgggaagcca cggtgacctc acaaggcccg gaatctccgc gagaatttca gtgttgtttt      540
cctctctcca cctttctcag ggacttccga aactccgcct ctccggtgac gtcagcatag      600
cgctgcgtcg gtacccacga gtggccatcg attcgacgtg tatttatacc cggtgagttc      660
ctcaagaggc cactcttgag tgccagcgag tagagttttc tcctccgagc cgctccgaca      720
ccgggactga aaatgagaca tattatctgc cacggaggtg ttattaccga agaaatggcc      780
gccagtcttt tggaccagct gatcgaagag gtactggctg ataatcttcc acctcctagc      840
cattttgaac cacctaccct tcacgaactg tatgatttag acgtgacggc ccccgaagat      900
cccaacgagg aggcggtttc gcagattttt cccgactctg taatgttggc ggtgcaggaa      960
g                                                                      961

<210> SEQ ID NO 2
<211> LENGTH: 2156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ccacatggtg gcagatgctg cattcgaaaa cgtttgaatt gataattatt atcatttgcg       60 ggtccttttcc ggcgatccgc cttgttacgg ggcggcgacc tcgcgggttt tcgctattta     120 tgaaaattt ccggtttaag gcgtttccgt tcttcttcgt cataacttaa tgttttatt        180 taaaataccc tctgaaaaga aaggaaacga caggatcttc tagacccggg agcggccgct      240
gtcgacattg attattgact agttattaat agtaatcaat tacggggtca ttagttcata     300
gcccatatat ggagttccgc gttacataac ttacggtaaa tggcccgcct ggctgaccgc      360
ccaacgaccc ccgcccattg acgtcaataa tgacgtatgt tcccatagta acgccaatag      420
ggactttcca ttgacgtcaa tgggtggagt atttacggta aactgcccac ttggcagtac      480
atcaagtgta tcatatgcca gtacgcccc tattgacgt caatgacggt aaatggcccg       540
cctggcatta tgcccagtac atgaccttat gggactttcc tacttggcag tacatctacg      600
tattagtcat cgctattacc atggtgatgc ggttttggca gtacatcaat gggcgtggat      660
agcggtttga ctcacgggga tttccaagtc tccaccccat tgacgtcaat gggagtttgt      720
tttggcacca aaatcaacgg gactttccaa aatgtcgtaa caactccgcc ccattgacgc     780
aaatgggcgg taggcgtgta cggtgggagg tctatataag cagagctctc tggctaacta      840
gagaacccac tgcttactgg cttatccaaa ttaatacgac tcactatagg gagacccaag      900
ctggctagcg tttaaactta agcttggtac cgagctcgga tccactagta acggccgcca      960
gtgtgctgga actcggctta caagacatga ctgtgatgag gagctgcttt cgccaattta     1020
acaccaagaa gaattgaggc tgcttgggag gaaggccagg aggaacacga gactgagaga     1080 tgaatttca acagaggctg caaagcctgt ggactttagc cagacccttc tgccctcctt     1140
```

-continued

```
tgctggcgac agcctctcaa atgcagatgg ttgtgctccc ttgcctgggt tttaccctgc    1200
ttctctggag ccaggtatca ggggcccagg gccaagaatt ccactttggg ccctgccaag    1260
tgaaggaggt tgttccccag aaactgtggg aagccttctg ggctgtgaaa gacactatgc    1320
aagctcagga taacatcacg agtgcccggc tgctgcagca ggaggttctg cagaacgtct    1380
cggatgctga gagctgttac cttgtccaca ccctgctgga gttctacttg aaaactgttt    1440
tcaaaaacta ccacaataga acagttgaag tcaggactct gaagtcattc tctactctgg    1500
ccaacaactt tgttctcatc gtgtcacaac tgcaacccag tcaagaaaat gagatgtttt    1560
ccatcagaga cagtgcacac aggcggttcc tgctattccg gagagcattt aaacagttgg    1620
acgtagaagc agctctgacc aaagcccttg gggaagtgga cattcttctg acctggatgc    1680
agaaactcta caagctctga atgtctagac caggacctcc ctcccctgg cactggtttg    1740 ttccctgtgt catttcaaac agtctaagcc gaattctgca gatatccatc acactggcgg    1800
ccgctcgagt ctagagggcc cgtttaaacc cgctgatcag cctcgactgt gccttctagt    1860
tgccagccat ctgttgtttg cccctccccc gtgccttcct tgaccctgga aggtgccact    1920
cccactgtcc tttcctaata aaatgaggaa attgcatcgc attgtctgag taggtgtcat    1980
tctattctgg ggggtgggt ggggcaggac agcaagggg aggattggga agacaatagc     2040
aggcatgctg gggatgcggt gggctctatg gcttcgcggc cgcaatcact agtgaattcg    2100
cggccgcctg caggtcggat ccgaattcga tatcactagt ggtacccacc cagtgg       2156
```

<210> SEQ ID NO 3
<211> LENGTH: 2356
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 3

```
tggaatgtca gtttcctcct gttcctgtcc atccgcaccc actatcttca tgttgttgca      60
gatgaagcgc gcaagaccgt ctgaagatac cttcaacccc gtgtatccat atgacacgga    120
aaccggtcct ccaactgtgc ctttttcttac tcctccctt gtatcccca atgggtttca     180 agagagtccc cctggggtac tctctttgcg cctatccgaa cctctagtta cctccaatgg    240
catgcttgcg ctcaaaatgg gcaacggcct ctctctggac gaggccggca accttacctc    300
ccaaaatgta accactgtga gcccacctct caaaaaaacc aagtcaaaca taaacctgga    360
aatatctgca cccctcacag ttacctcaga agccctaact gtggctgccg ccgcacctct    420
aatggtcgcg ggcaacacac tcaccatgca atcacaggcc ccgctaaccg tgcacgactc    480
caaacttagc attgccaccc aaggacccct cacagtgtca gaaggaaagc tagccctgca    540
aacatcaggc cccctcacca ccaccgatag cagtaccctt actatcactg cctcaccccc    600
tctaactact gccactggta gcttgggcat tgacttgaaa gagcccattt atacacaaaa    660
tggaaaacta ggactaaagt acgggggctcc tttgcatgta acagacgacc taaacacttt    720
gaccgtagca actggtccag gtgtgactat taataatact tccttgcaaa ctaaagttac    780
tggagccttg gcttttgatt cacaaggcaa tatgcaactt aatgtagcag gaggactaag    840
gattgattct caaaacagac gccttatact tgatgttagt tatccgtttg atgctcaaaa    900
ccaactaaat ctaagactag acagggccc tctttttata aactcagccc acaacttgga    960
tattaactac aacaaggcc tttacttgtt tacagcttca aacaattcca aaaagcttga    1020
```

-continued

```
ggttaaccta agcactgcca aggggttgat gtttgacgct acagccatag ccattaatgc    1080
aggagatggg cttgaatttg gttcacctaa tgcaccaaac acaaatcccc tcaaaacaaa    1140
aattggccat ggcctagaat ttgattcaaa caaggctatg gttcctaaac taggaactgg    1200
ccttagtttt gacagcacag gtgccattac agtaggaaac aaaaataatg ataagctaac    1260
cctatggaca gctccaaaac cagaagccaa ctgcataatt gaatacggga aacaaaaccc    1320
agatagcaaa ctaactttaa tccttgtaaa aaatggagga attgttaatg gatatgtaac    1380
gctaatggga gcctcagact acgttaacac cttatttaaa aacaaaaatg tctccattaa    1440
tgtagaacta tactttgatg ccactggtca tatattacca gactcatctt ctcttaaaac    1500
agatctagaa ctaaaataca agcaaaccgc tgactttagt gcaagaggtt ttatgccaag    1560
tactacagcg tatccatttg tccttcctaa tgcgggaaca cataatgaaa attatatttt    1620
tggtcaatgc tactacaaag caagcgatgg tgccctttt ccgttggaag ttactgttat    1680
gcttaataaa cgcctgccag atagtcgcac atcctatgtt atgactttt tattggtcct    1740 tgaatgctgg tctagctcca gaaactactc aggcaaccct cataacctcc ccatttacct    1800
tttcctatat tagagaagat gactaataaa ctctaaagaa tcgtttgtgt tatgtttcaa    1860
cgtgtttatt tttcaattgc agaaaatttc aagtcatttt tcattcagta gtatagcccc    1920
accaccacat agcttataca gatcaccgta ccttaatcaa actcacagaa ccctagtatt    1980
caacctgcca cctccctccc aacacacaga gtacacagtc ctttctcccc ggctggcctt    2040
aaaaagcatc atatcatggg taacagacat attcttaggt gttatattcc acacggtttc    2100
ctgtcgagcc aaacgctcat cagtgatatt aataaactcc ccgggcagct cacttaagtt    2160
catgtcgctg tccagctgct gagccacagg ctgctgtcca acttgcggtt gcttaacggg    2220
cggcgaagga gaagtccacg cctacatggg ggtagagtca taatcgtgca tcaggatagg    2280
ggtggtgctg cagcagcgcg cgaataaact gcttgcggcc gcggctccgt cctgcaggaa    2340
tacaacatgg cagtgg                                                    2356
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaacatgatg actaccaagc ttggc                                           25

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgatagcat cttgttctta gtctttttct taataggg                             38

<210> SEQ ID NO 6
<211> LENGTH: 587
<212> TYPE: PRT
<213> ORGANISM: Artificial Sequence
<220> FEATURE:
<223> OTHER INFORMATION: Description of Artificial Sequence: Synthetic

```
                      polypeptide
<220> FEATURE:
<221> NAME/KEY: MOD_RES
<222> LOCATION: (66)..(66)
<223> OTHER INFORMATION: Any amino acid

<400> SEQUENCE: 6

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
50                  55                  60

Lys Xaa Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
290                 295                 300

Lys Gly Leu Tyr Leu Phe Thr Ala Ser Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Arg Phe Asp
        355                 360                 365

Ser Asn Lys Ala Met Val Pro Lys Leu Gly Thr Gly Leu Ser Phe Asp
370                 375                 380
```

-continued

```
Ser Thr Gly Ala Ile Thr Val Gly Asn Lys Asn Asn Asp Lys Leu Thr
385                 390                 395                 400

Leu Trp Thr Gly Pro Lys Pro Glu Ala Asn Cys Ile Ile Glu Tyr Gly
            405                 410                 415

Lys Gln Asn Pro Asp Ser Lys Leu Thr Leu Ile Leu Val Lys Asn Gly
            420                 425                 430

Gly Ile Val Asn Gly Tyr Val Thr Leu Met Gly Ala Ser Asp Tyr Val
        435                 440                 445

Asn Thr Leu Phe Lys Asn Lys Asn Val Ser Thr Asn Val Glu Leu Tyr
    450                 455                 460

Phe Asp Ala Thr Gly His Ile Leu Pro Asp Ser Ser Ser Leu Lys Thr
465                 470                 475                 480

Asp Leu Glu Leu Lys Tyr Lys Gln Thr Ala Asp Phe Ser Ala Arg Gly
            485                 490                 495

Phe Met Pro Ser Thr Thr Ala Tyr Pro Phe Val Leu Pro Asn Ala Gly
            500                 505                 510

Thr His Asn Glu Asn Tyr Ile Phe Gly Gln Cys Tyr Tyr Lys Ala Ser
            515                 520                 525

Asp Gly Ala Leu Phe Pro Leu Glu Val Thr Leu Met Leu Asn Lys Arg
    530                 535                 540

Leu Pro Asp Ser Arg Thr Ser Tyr Val Met Thr Phe Leu Trp Ser Leu
545                 550                 555                 560

Asn Ala Gly Leu Ala Pro Glu Thr Thr Gln Ala Thr Leu Ile Thr Ser
            565                 570                 575

Pro Phe Thr Phe Ser Tyr Ile Arg Glu Asp Asp
            580                 585
```